(12) United States Patent
Benson et al.

(10) Patent No.: US 9,353,181 B2
(45) Date of Patent: *May 31, 2016

(54) HUMAN ANTI-IL-23 ANTIBODIES, COMPOSITIONS, METHODS AND USES

(75) Inventors: Jacqueline Benson, Malvern, PA (US); Jill Carton, Malvern, PA (US); Mark Cunningham, Kennett Square, PA (US); Yevgeniya I. Orlovsky, Chadds Ford, PA (US); Robert Rauchenberger, Farchant (DE); Raymond Sweet, Bryn Mawr, PA (US)

(73) Assignee: Janssen Biotech, Inc., Horsham, PA (US)

( * ) Notice: Subject to any disclaimer, the term of this patent is extended or adjusted under 35 U.S.C. 154(b) by 800 days.

This patent is subject to a terminal disclaimer.

(21) Appl. No.: 13/524,122

(22) Filed: Jun. 15, 2012

(65) Prior Publication Data

US 2012/0251454 A1    Oct. 4, 2012

Related U.S. Application Data

(62) Division of application No. 13/173,090, filed on Jun. 30, 2011, now Pat. No. 8,221,760, which is a division of application No. 12/855,354, filed on Aug. 12, 2010, now Pat. No. 7,993,645, which is a division of application No. 11/617,503, filed on Dec. 28, 2006, now Pat. No. 7,935,344.

(60) Provisional application No. 60/754,889, filed on Dec. 29, 2005.

(51) Int. Cl.
*A61K 39/395* (2006.01)
*C07K 16/24* (2006.01)
*A61K 39/00* (2006.01)

(52) U.S. Cl.
CPC ......... *C07K 16/244* (2013.01); *A61K 2039/505* (2013.01); *C07K 2316/96* (2013.01); *C07K 2317/21* (2013.01); *C07K 2317/34* (2013.01); *C07K 2317/52* (2013.01); *C07K 2317/55* (2013.01); *C07K 2317/565* (2013.01); *C07K 2317/73* (2013.01); *C07K 2317/76* (2013.01); *C07K 2317/92* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,859,205 A | 1/1999 | Adair et al. | |
| 6,060,284 A | 5/2000 | Bazan | |
| 6,479,634 B1 | 11/2002 | Bazan | |
| 6,495,667 B1 | 12/2002 | Bazan | |
| 6,610,285 B1 | 8/2003 | Hirata | |
| 6,756,481 B2 | 6/2004 | Chirica et al. | |
| 6,800,460 B1 | 10/2004 | Oppmann et al. | |
| 6,835,825 B1 | 12/2004 | Bazan | |
| RE39,015 E | 3/2006 | Bazan et al. | |
| 7,090,847 B1 | 8/2006 | Oppmann et al. | |
| 7,183,382 B2 | 2/2007 | Oppmann et al. | |
| 7,247,711 B2 | 7/2007 | Benson et al. | |
| 7,252,971 B2 | 8/2007 | Benson et al. | |
| 7,282,204 B2 | 10/2007 | Oft et al. | |
| 7,491,391 B2 | 2/2009 | Benson et al. | |
| 7,935,344 B2 * | 5/2011 | Benson et al. | 424/145.1 |
| 7,993,645 B2 * | 8/2011 | Benson et al. | 424/145.1 |
| 8,106,177 B2 | 1/2012 | Benson et al. | |
| 2002/0042386 A1 | 4/2002 | Rosen et al. | |
| 2003/0124617 A1 | 7/2003 | Gram et al. | |
| 2003/0162261 A1 | 8/2003 | Oppmann et al. | |
| 2004/0185506 A1 | 9/2004 | Heavner | |
| 2004/0258686 A1 | 12/2004 | Chirica et al. | |
| 2005/0049402 A1 | 3/2005 | Babcook et al. | |
| 2005/0208052 A1 | 9/2005 | Katsikis et al. | |
| 2005/0244874 A1 | 11/2005 | Kastelein et al. | |
| 2007/0048315 A1 | 3/2007 | Presta | |

FOREIGN PATENT DOCUMENTS

| | | |
|---|---|---|
| WO | WO 99/05280 A1 | 2/1999 |
| WO | WO 99/40195 A1 | 8/1999 |
| WO | WO 00/09552 A1 | 2/2000 |
| WO | WO 00/53631 A1 | 9/2000 |
| WO | WO 00/70049 A2 | 11/2000 |
| WO | WO 01/18051 A2 | 3/2001 |
| WO | WO 01/85790 A2 | 11/2001 |
| WO | WO 2004/042009 A2 | 5/2004 |
| WO | WO 2004/058178 A2 | 7/2004 |
| WO | WO 2004/071517 A2 | 8/2004 |
| WO | WO 2004/081190 A2 | 9/2004 |
| WO | WO 2004/101750 A2 | 11/2004 |
| WO | WO 2005/103083 A2 | 11/2005 |
| WO | WO 2005/108425 A1 | 11/2005 |
| WO | WO 2007/024846 A2 | 3/2007 |

OTHER PUBLICATIONS

Oppmann, et al., "Novel p19 Protein Engages IL-12p40 to Form a Cytokine, IL-23, with Biological Activities Similar as Well as Distinct from IL-12," Immunity, 13: 715-725 (2000).

Peter J. Barnes, "Cytokine-directed therapies for the treatment of chronic airway diseases," Cytokine & Growth Factor Reviews 14 (2003): 511-522 (2003).

Trinchieri, et al., "The IL-12 Family of Heterodimeric Cytokines: New Players in the Regulation of T Cell Responses," Immunity, 19: 641-644 (2003).

Maguire van Seventer, et al., "Interferon-β differentially regulates expression of the IL-12 family members p35, p40, p19 and EB13 in activated human dendritic cells," Journal of Neuroimmunology, 133: 60-71 (2002).

Yadav, et al., "Cytokines and autoimmunity: redundancy defines their complex nature," Current Opinion in Immunology, 15: 697-703 (2003).

Murphy, et al., "Divergent Pro- and Antiinflammatory Roles for IL-23 and IL-12 in Joint Autoimmune Inflammation," Journal of Experimental Medicine, 198(12): 1951-1957 (2003).

(Continued)

*Primary Examiner* — Zachary Skelding
(74) *Attorney, Agent, or Firm* — Eric Dichter

(57) ABSTRACT

A human anti-IL-23p19 antibody, including isolated nucleic acids that encode at least one anti-IL-23p19 antibody, vectors, host cells, and methods of making and using thereof have applications in diagnostic and/or therapeutic compositions, methods and devices.

9 Claims, 25 Drawing Sheets

(56) References Cited

OTHER PUBLICATIONS

David M. Frucht, "IL-23: A Cytokine That Acts on Memory T Cells," Science STKE, 114: 1-3 (2002).
Wiekowski, et al., "Ubiquitous Transgenic Expression of the IL-23 Subunit p19 Induces Multiorgan Inflammation, Runting, Infertility, and Premature Death," Journal of Immunology, 166: 7563-7570 (2001).
Belladonna, et al., "IL-23 and IL-12 Have Overlapping, but Distinct, Effects on Murine Dendritic Cells," The Journal of Immunology, 168: 5448-5454 (2002).
Parham, et al., "A Receptor for the Heterodimeric Cytokine IL-23 is Composed of IL-12Rβ1 and a Novel Cytokine Receptor Subunit, IL-23R," The Journal of Immunology, 168: 5699-5708 (2002).
Cua, et al., "Interleukin-23 rather than interleukin-12 is the critical cytokine for autoimmune inflammation of the brain," Nature, 421: 744-748 (2003).
GenBank Accession No. AF301620, Oppmann, et al., Dec. 4, 2000.
GenBank Accession No. AA418955, Hillier, et al., May 12, 1997.
GenBank Accession No. C06368, J. Takeda, Aug. 9, 1996.
GenBank Accession No. AA418747, Hillier, et al., May 12, 1997.
Wiendl, et al., "Therapeutic Approaches in Multiple Sclerosis: Lessons from Failed and Interrupted Treatment Trials," BioDrugs, 16(3): 183-200 (2002).
Eduardo Padlan, "Anatomy of the Antibody Molecule," Molecular Immunology, 31(3): 169-217 (1994).
Portolano, et al., "Lack of Promiscuity in Autoantigen-Specific H and L Chain Combinations as Revealed by Human H and L Chain 'Roulette'," Journal of Immunology, 150(3): 880-887 (1993).
Knappik, et al., "Tully Synthetic Human Combinatorial Antibody Libraries (HuCAL) Based on Modular Consensus Frameworks and CDRs Randomized with Trinucleotides," Journal of Molecular Biology, 296(1): 57-86 (2000).
Vajdos, et al., "Comprehensive Functional Maps of the Antigen-Binding Site of an Anti-ErbB2 Antibody Obtained with Shotgun Scanning Mutagenesis," Journal of Molecular Biology, 320(2): 415-428 (2002).
Barrie, et al., "The interleukin-12 family of cytokines: Therapeutic targets for inflammatory disease mediation," Clinical and Applied Immunology Reviews, 5: 225-240 (1995).
Kretzschmar, et al., "Antibody discovery: phage display," Current Opinion in Biotechnology, 13: 598-602 (2002).
Hu, et al., "Information contributed by meta-analysis in exposure-response modeling: application to phase 2 dose selection of guselkumab in patients with moderate-to-severe psoriasis," Journal of Pharmacokinetics and Pharmacodynamics (2014).
Sofen, et al., "Guselkumab (an IL-23-specific mAb) demonstrates clinical and molecular response in patients with moderate-to-severe psoriasis," Journal of Allergy and Clinical Immunology, 133(4): 1032-1040 (2014).
Sofen, et al., "Results of a single ascending dose study to assess the safety and tolerability of CNTO1959 following intravenous or subcutaneous administration in healthy subjects and in subjects with moderate to severe psoriasis," British Journal of Dermatology, Abstract FC-21 (2011). Abstract only.
Krnjevic-Pezic, et al., "Our experience using ustekinumab in patients with plaque psoriasis," British Journal of Dermatology, Abstract P-24 (2011). Abstract only.
Fan, et al., "Mixed treatment comparison of infliximab with ustekinumab in patients with moderate to severe psoriasis," British Journal of Dermatology, Abstract P-64 (2011). Abstract only.
Aggarwal, et al., "Interleukin-23 Promotes a Distinct CD4 T Cell Activation State characterized by the Production of Interleukin-17," The Journal of Biological Chemistry, 278(3): 1910-1914 (2003).
Harlow, et al., Antibodies A Laboratory Manual, Cold Spring Harbor Laboratory, pp. 567-569 (1988).
Lee, et al., "Increased Expression of Interleukin 23 p19 and p40 in Lesional Skin of Patients with Psoriasis Vulgaris," Journal of Experimental Medicine, 199(1): 125-130 (2004).
Mendez, et al., "Functional transplant of megabase human immunoglobulin loci recapitulates human antibody response in mice," Nature Genetics, 15(2): 146-156 (1997).
Schmidt, et al., Expression of Interleukin-12-Related Cytokine Transcripts in Inflammatory Bowel Disease: Elevated Interleukin-23p19 and Interneukin-27p28 in Crohn's Disease But Not in Ulcerative Colitis, 11: 16-23 (2005).

* cited by examiner

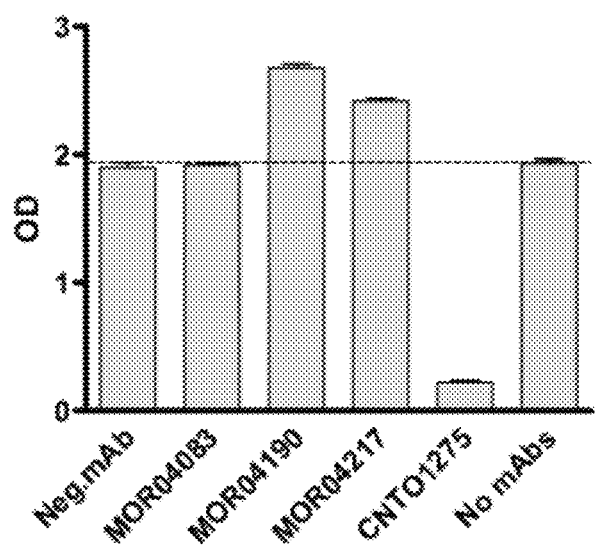

US 9,353,181 B2

HUMAN ANTI-IL-23 ANTIBODIES, COMPOSITIONS, METHODS AND USES

CROSS REFERENCE TO RELATED APPLICATION

This application is a divisional of U.S. application Ser. No. 13/173,090, filed 30 Jun. 2011, now U.S. Pat. No. 8,221,760, which is a divisional of U.S. application Ser. No. 12/855,354, filed 12 Aug. 2010, now U.S. Pat. No. 7,993,645, which is a divisional of U.S. application Ser. No. 11/617,503, filed 28 Dec. 2006, now U.S. Pat. No. 7,935,344, which claims the benefit of U.S. Provisional Application Ser. No. 60/754,889, filed 29 Dec. 2005. The entire contents of each of the aforementioned applications are incorporated herein by reference in their entireties.

FIELD OF THE INVENTION

The present invention relates to antibodies, including specified portions or variants, specific for at least one IL-23 protein or fragment thereof, as well as anti-idiotype antibodies, and nucleic acids encoding anti-IL-23p19 antibodies, complementary nucleic acids, vectors, host cells, and methods of making and using thereof, including therapeutic formulations, administration and devices.

BACKGROUND OF THE INVENTION

Interleukin (IL)-12 is a secreted heterodimeric cytokine comprised of 2 disulfide-linked glycosylated protein subunits, designated p35 and p40 for their approximate molecular weights. IL-12 is produced primarily by antigen-presenting cells and drives cell-mediated immunity by binding to a two-chain receptor complex that is expressed on the surface of T cells or natural killer (NK) cells. The IL-12 receptor beta-1 (IL-12Rβ1) chain binds to the p40 subunit of IL-12, providing the primary interaction between IL-12 and its receptor. However, it is the IL-12p35 ligation of the second receptor chain, IL-12Rβ2, that confers intracellular signaling (e.g. STAT4 phosphorylation) and activation of the receptor-bearing cell (Presky et al, 1996). IL-12 signaling concurrent with antigen presentation is thought to invoke T cell differentiation towards the T helper 1 (Th1) phenotype, characterized by interferon gamma (IFNγ) production (Trinchieri, 2003). Th1 cells are believed to promote immunity to some intracellular pathogens, generate complement-fixing antibody isotypes, and contribute to tumor immunosurveillance. Thus, IL-12 is thought to be a significant component to host defense immune mechanisms.

It was discovered that the p40 protein subunit of IL-12 can also associate with a separate protein subunit, designated p19, to form a novel cytokine, IL-23 (Oppman et al, 2000). IL-23 also signals through a two-chain receptor complex. Since the p40 subunit is shared between IL-12 and IL-23, it follows that the IL-12Rβ1 chain is also shared between IL-12 and IL-23. However, it is the IL-23p19 ligation of the second component of the IL-23 receptor complex, IL-23R, that confers IL-23 specific intracellular signaling (e.g., STAT3 phosphorylation) and subsequent IL-17 production by T cells (Parham et al, 2002; Aggarwal et al. 2003). Recent studies have demonstrated that the biological functions of IL-23 are distinct from those of IL-12, despite the structural similarity between the two cytokines (Langrish et al, 2005).

Abnormal regulation of IL-12 and Th1 cell populations has been associated with many immune-mediated diseases since neutralization of IL-12 by antibodies is effective in treating animal models of psoriasis, multiple sclerosis (MS), rheumatoid arthritis, inflammatory bowel disease, insulin-dependent (type 1) diabetes mellitus, and uveitis (Leonard et al, 1995; Hong et al, 1999; Malfait et al, 1998; Davidson et al, 1998). However, since these studies targeted the shared p40 subunit, both IL-12 and IL-23 were neutralized in vivo. Therefore, it was unclear whether IL-12 or IL-23 was mediating disease, or if both cytokines needed to be inhibited to achieve disease suppression. Recent studies have confirmed through IL-23p19 deficient mice or specific antibody neutralization of IL-23 that IL-23 inhibition can provide equivalent benefit as anti-IL-12p40 strategies (Cua et al, 2003, Murphy et al, 2003, Benson et al 2004). Therefore, there is increasing evidence for the specific role of IL-23 in immune-mediated disease. Neutralization of IL-23 without inhibition of IL-12 pathways could then provide effective therapy of immune-mediated disease with limited impact on important host defense immune mechanism. This would represent a significant improvement over current therapeutic options.

SUMMARY OF THE INVENTION

The present invention provides isolated mammalian, including, without limitation, human, antibodies that bind to the p19 subunit of IL-23, anti-IL-23p19 antibodies (also referred to as IL-23p19 antibodies), immunoglobulins, fragments, cleavage products and other specified portions and variants thereof, as well as anti-IL-23p19 antibody compositions, IL-23p19 anti-idiotype antibodies, encoding or complementary nucleic acids, vectors, host cells, compositions, combinations, formulations, devices, transgenic animals, transgenic plants, and methods of making and using them.

The present invention provides, in one aspect, isolated nucleic acid molecules comprising, complementary, or hybridizing to, a polynucleotide encoding specific anti-IL-23p19 antibodies or anti-idiotype antibodies, comprising at least one specified sequence, domain, portion or variant thereof. The present invention further provides recombinant vectors comprising said anti-IL-23p19 antibody nucleic acid molecules, host cells containing such nucleic acids and/or recombinant vectors, as well as methods of making and/or using such antibody nucleic acids, vectors and/or host cells.

The present invention also provides at least one method for expressing at least one anti-IL-23p19 antibody, or IL-23p19 anti-idiotype antibody, in a host cell, comprising culturing a host cell as described herein under conditions wherein at least one anti-IL-23p19 antibody is expressed in detectable and/or recoverable amounts.

The present invention also provides at least one composition comprising (a) an isolated anti-IL-23p19 antibody encoding nucleic acid and/or antibody as described herein; and (b) a suitable and/or pharmaceutically acceptable carrier or diluent.

The present invention further provides at least one anti-IL-23p19 antibody method or composition, for administering a therapeutically effective amount to modulate or treat at least one IL-23p19 related condition in a cell, tissue, organ, animal or patient and/or, prior to, subsequent to, or during a related condition, as known in the art and/or as described herein.

The present invention also provides at least one composition, device and/or method of delivery of a therapeutically or prophylactically effective amount of at least one anti-IL-23p19 antibody, according to the present invention.

The present invention further provides at least one anti-IL-23p19 antibody method or composition, for diagnosing at least one IL-23 related condition in a cell, tissue, organ, animal or patient and/or, prior to, subsequent to, or during a related condition, as known in the art and/or as described herein.

The present invention also provides at least one composition, device and/or method of delivery for diagnosing of at least one anti-IL-23p19 antibody, according to the present invention.

Also provided is a medical device, comprising at least one isolated mammalian anti-IL-23p19 antibody of the invention, wherein the device is suitable for contacting or administering the at least one anti-IL-23p19 antibody, IL-23p19 anti-idiotypic antibody, nucleic acid molecule, compound, protein, and/or composition.

Also provided is an article of manufacture for human pharmaceutical or diagnostic use, comprising packaging material, and a container comprising a solution or a lyophilized form of at least one isolated anti-IL-23p19 antibody of the present invention. The article of manufacture can optionally have the container as a component of a delivery device or system.

The present invention further provides any invention described herein.

DESCRIPTION OF THE FIGURES

FIG. 3C shows that antibodies MOR04083, MOR04190, and MOR04217 do not inhibit IL-12 binding to IL-12Rβ1-Fc binding.

DESCRIPTION OF THE INVENTION

Figure 1A:
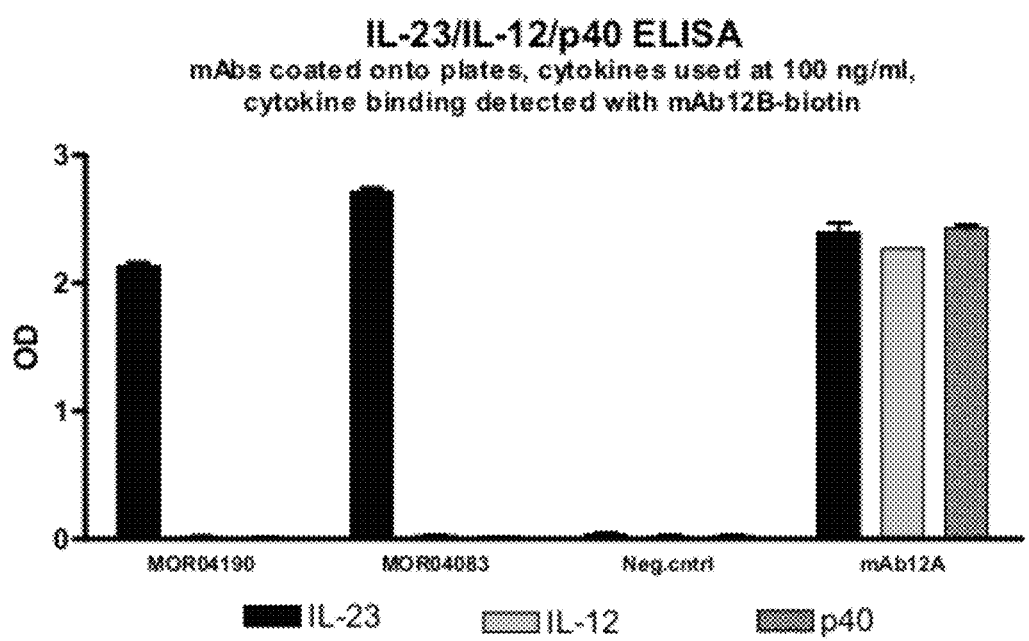
FIG. 1A shows that human IL-23p19 antibodies bind specifically to hrIL-23 and not hrIL-12 or hrp40 monomer. An anti-IL-12/IL-23 p40 antibody is shown to bind IL-23, IL-12 and the p40 monomer.

The present invention provides isolated, recombinant and/or synthetic anti-IL-23p19 antibodies, including, without limitation, mammalian (e.g., human antibodies) and IL-23p19 anti-idiotype antibodies thereto, as well as compositions and encoding nucleic acid molecules comprising at least one polynucleotide encoding at least one anti-IL-23p19 antibody or anti-idiotype antibody. The present invention further includes, but is not limited to, methods of making and using such nucleic acids and antibodies and anti-idiotype antibodies, including diagnostic and therapeutic compositions, methods and devices.

As used herein, an "anti-IL-23p19 antibody," "IL-23p19 antibody," "anti-IL-23p19 antibody portion," or "anti-IL-23p19 antibody fragment" and/or "anti-IL-23p19 antibody variant" and the like include any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of an IL-23 receptor or binding protein, which can be incorporated into an antibody of the present invention. Such antibody optionally further affects a specific ligand, such as but not limited to, where such antibody modulates, decreases, increases, antagonizes, agonizes, mitigates, alleviates, blocks, inhibits, abrogates and/or interferes with at least one IL-23 activity or binding, or with IL-23 receptor activity or binding, in vitro, in situ and/or in vivo. As a non-limiting example, a suitable anti-IL-23p19 antibody, specified portion or variant of the present invention can bind at least one IL-23 molecule, or specified portions, variants or domains thereof. A suitable anti-IL-23p19 antibody, specified portion, or variant can also optionally affect at least one of IL-23p19 activity or function, such as but not limited to, RNA, DNA or protein synthesis, IL-23 release, IL-23 receptor signaling, membrane IL-23 cleavage, IL-23 activity, IL-23 production and/or synthesis.

The term "antibody" is further intended to encompass antibodies, digestion fragments, specified portions and variants thereof, including, without limitation, antibody mimetics or comprising portions of antibodies that mimic the structure and/or function of an antibody or specified fragment or portion thereof, including, without limitation, single chain antibodies, single domain antibodies, and fragments thereof. Functional fragments include antigen-binding fragments that bind to a human IL-23p19. For example, antibody fragments capable of binding to IL-23p19 or portions thereof, including, but not limited to, Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the $C_H1$ domain and/or hinge region of the heavy chain. The various portions of antibodies can be joined together chemically by conventional techniques, or can be prepared as a contiguous protein using genetic engineering techniques.

The term "human antibody," as used herein, is intended to include antibodies having variable and constant regions derived from or closely matching human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). Thus, as used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially similar to a human germline antibody. Human antibodies have been classified into groupings based on their amino acid sequence similarities, see e.g. http://people.cryst.bbk.ac.uk/~ubcg07s/. Thus, using a sequence similarity search, an antibody with similar linear sequence can be chosen as a template to create "humanized antibodies."

"Humanization" (also called Reshaping or CDR-grafting) is now a well-established technique for reducing the immunogenicity of monoclonal antibodies (mAbs) from xenogeneic sources (commonly rodent) and for improving the effector functions (ADCC, complement activation, C1q binding). The engineered mAb is engineered using the techniques of molecular biology, however simple CDR-grafting of the rodent complementarity-determining regions (CDRs) into human frameworks often results in loss of binding affinity and/or specificity of the original mAb. In order to humanize an antibody, the design of the humanized antibody includes variations such as conservative amino acid substitutions in residues of the CDRs, and back substitution of residues from the rodent mAb into the human framework regions (backmutations). The positions can be discerned or identified by sequence comparison for structural analysis or by analysis of a homology model of the variable regions' 3D structure. The process of affinity maturation has most recently used phage libraries to vary the amino acids at chosen positions. Similarly, many approaches have been used to choose the most appropriate human frameworks in which to graft the rodent CDRs. As the datasets of known parameters for antibody structures increases, so does the sophistication and refinement of these techniques. Consensus or germline sequences from a single antibody or fragments of the framework sequences within each light or heavy chain variable region from several different human mAbs can be used. Another approach to humanization is to modify only surface residues of the rodent sequence with the most common residues found in human mAbs and has been termed "resurfacing" or "veneering." Known human Ig sequences are disclosed, e.g., www.ncbi.nlm.nih.gov/entrez/query.fcgi; www.ncbi.nih.gov/igblast; www.atcc.org/phage/hdb.html; www.kabatdatabase.com/top.html; www.antibodyresource.com/onlinecomp.html; www.appliedbiosystems.com; www.biodesign.com; antibody.bath.ac.uk; www.unizh.ch; www.cryst.bbk.ac.uk/~ubcg07s; Kabat et al., Sequences of Proteins of Immunological Interest, U.S. Dept. Health (1983), each entirely incorporated herein by reference. Often, the human or humanized antibody is substantially non-immunogenic in humans.

Similarly, antibodies designated primate (monkey, baboon, chimpanzee, etc.), rodent (mouse, rat, rabbit, guinea pig, hamster, and the like) and other mammals designate such species, sub-genus, genus, sub-family, and family specific antibodies. Further, chimeric antibodies can include any combination of the above. Such changes or variations optionally and preferably retain or reduce the immunogenicity in humans or other species relative to non-modified antibodies. Thus, a human antibody is distinct from a chimeric or humanized antibody.

It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain or single domain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably, human or humanized, antibodies that have binding specificities for at least two different antigens. In the present case, one of the binding specificities is for at least one IL-23p19 protein subunit, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule is usually done by affinity chromatography steps. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

Anti-IL-23p19 antibodies useful in the methods and compositions of the present invention can optionally be characterized by high affinity binding to IL-23p19 and, optionally and preferably, as having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as the incidence of titrable levels of antibodies to the anti-IL-23p19 antibody in patients treated with anti-IL-23p19 antibody as occurring in less than 25% of patients treated, preferably, in less than 10% of patients treated with the recommended dose for the recommended course of therapy during the treatment period.

The isolated nucleic acids of the present invention can be used for production of at least one anti-IL-23p19 antibody or specified variant thereof, which can be used to measure or effect in an cell, tissue, organ or animal (including mammals and humans), to diagnose, monitor, modulate, treat, alleviate, help prevent the incidence of, or reduce the symptoms of, at least one IL-23 related condition, selected from, but not limited to, at least one of an immune disorder or disease, a cardiovascular disorder or disease, an infectious, malignant, and/or neurologic disorder or disease, or other known or specified IL-23 related condition.

Such a method can comprise administering an effective amount of a composition or a pharmaceutical composition comprising at least one anti-IL-23p19 antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 µg/ml serum concentration per single, multiple, or continuous administration, or any effective range or value therein, as done and determined using known methods, as described herein or known in the relevant arts.

Antibodies of the Present Invention—Production and Generation

At least one anti-IL-23p19 antibody of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2" Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

Antibodies that are specific for human IL-23p19 proteins or fragments thereof can be obtained from recombinant human antibody libraries using an appropriate antigen, such as an isolated IL-23p19 protein and/or a portion thereof (including synthetic molecules, such as synthetic peptides). Other specific or general antibodies, including, without limitation, mammalian antibodies, can be similarly raised. Preparation of antigens, and isolation of antibodies from human libraries can be performed using any suitable technique.

In one approach, a recombinant antibody is obtained by phage display using antibody libraries (Hoogenboom H R. Overview of antibody phage-display technology and its applications. *Methods in Molecular Biology*. 178:1-37, 2002). In a preferred approach, a recombinant human Fab is isolated from the HuCal Gold Library developed by MorphoSys, AG (Kretzschmar, 2002) and subsequently improved in its activity by CDR cassette diversification (Knappik et al., 2000; Krebs et al., 2001).

Recombinant human antibodies recovered from phage display libraries may be engineered to replace certain residues with specific amino acids corresponding to consensus or specific human antibody sequences. These sequences are identified by comparisons to databases of known human germline or rearranged antibodies.

Known human Ig sequences are disclosed, e.g., www.ncbi.nlm.nih.gov/entrez/query.fcgi; www.ncbi.nih.gov/igblast; www.atcc.org/phage/hdb.html; www.mrc-cpe.cam.ac.uk/ALIGNMENTS.php; www.kabatdatabase.com/top.html; ftp.ncbi.nih.gov/repository/kabat; www.imgt.cines.fr.8104/; www.biochem.unizh.ch/antibody/index.html; www.sciquest.com; www.abcam.com; www.antibodyresource.com/onlinecomp.html; www.public.iastate.edu/~pedro/research_tools.html; www.whfreeman.com/immunology/CH05/kuby05.htm; www.hhmi.org/grants/lectures/1996/vlab; www.path.cam.ac.uk/~mrc7/mikeimages.html; mcb.harvard.edu/BioLinks/Immunology.html; www.immunologylink.com; pathbox.wustl.edu/~hcenter/index.html; www.appliedbiosystems.com; www.nal.usda.gov/awic/pubs/antibody; www.m.ehime-u.ac.jp/~yasuhito/Elisa.html; www.biodesign.com; www.cancerresearchuk.org; www.biotech.ufl.edu; www.isac-net.org; baserv.uci.kun.nl/~jraats/links1.html; www.recab.uni-hd.de/immuno.bme.nwu.edu; www.mrc-cpe.cam.ac.uk; www.ibt.unam.mx/vir/V_mice.html; http://www.bioinforg.uk/abs; antibody.bath.ac.uk; www.unizh.ch; www.cryst.bbk.ac.uk/~ubcg07s; www.nimr.mrc.ac.uk/CC/ccaewg/ccaewg.html; www.path.cam.ac.uk/~mrc7/humanisation/TAHHP.html; www.ibt.unam.mx/vir/structure/stat_aim.html; www.biosci.missouri.edu/smithgp/index.html; www.jerini.de; Kabat et al., Sequences of Proteins of Immunological Interest, U.S. Dept. Health (1983), each entirely incorporated herein by reference.

Such replaced amino acids can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing antigen binding.

Optionally, human antibodies can be engineered with retention of high affinity for the antigen and other favorable biological properties. To achieve this goal, the human antibodies can be optionally prepared by a process of analysis of the parental sequences and various conceptual engineered products using three-dimensional models of the parental, engineered, and human sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, residues can be selected and combined from the parent and reference human sequences so that the desired antibody characteristic, such as affinity for the target antigen(s), is achieved. Alternatively, or in addition to, the above procedures, engineering can be accomplished empirically by CDR cassette diversification and selection for the desired activity, such as described for the MorphoSys HuCAL system (Knappik et al., 2000; Krebs et al., 2001).

In addition, the IL-23p19 antibody of the present invention may comprise a human germline light chain framework. In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain embodiments, this light chain human germline framework is selected from V1-11, V1-13, V1-16, V1-17, V1-18, V1-19, V1-2, V1-20, V1-22, V1-3, V1-4, V1-5, V1-7, V1- 9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6. See PCT WO 2005/005604 for a description of the different germline sequences.

In other embodiments, the IL-23 antibody of the present invention may comprise a human germline heavy chain framework. In particular embodiments, this heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81. See PCT WO 2005/005604 for a description of the different germline sequences.

In particular embodiments, the light chain variable region and/or heavy chain variable region comprises a framework region or at least a portion of a framework region (e.g., containing 2 or 3 subregions, such as FR2 and FR3). In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g., human germline) or comprises human consensus sequences for the particular framework (readily available at the sources of known human Ig sequences described above). In other embodiments, at least FRH1, FRH2, FRH3, or FRH4 is a germline sequence (e.g., human germline) or comprises human consensus sequences for the particular framework. In preferred embodiments, the framework region is a human framework region.

Engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

In certain embodiments, the antibody comprises an altered (e.g., mutated) Fc region. For example, in some embodiments, the Fc region has been altered to reduce or enhance the effector functions of the antibody. In some embodiments, the Fc region is an isotype selected from IgM, IgA, IgG, IgE, or other isotype.

Alternatively or additionally, it may be useful to combine amino acid modifications with one or more further amino acid modifications that alter C1q binding and/or the complement dependent cytotoxicity (CDC) function of the Fc region of an IL-23p19 binding molecule. The binding polypeptide of particular interest may be one that binds to C1q and displays complement dependent cytotoxicity. Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO/0042072, which is hereby incorporated by reference.

As disclosed above, one can design an Fc region of the IL-23p19 antibody of the present invention with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of the IL-23p19 antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

Fc mutations can also be introduced and engineered to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, (J. Biol. Chem. 276:6591-6604).

Another type of amino acid substitution serves to alter the glycosylation pattern of the Fc region of the IL-23p19 antibody. Glycosylation of an Fc region is typically either N-linked or O-linked. N-linked refers to the attachment of the carbohydrate moiety to the side chain of an asparagine residue. O-linked glycosylation refers to the attachment of one of the sugars N-aceylgalactosamine, galactose, or xylose to a hydroxyamino acid, most commonly serine orthreonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an IL-23p19 antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the IL-23p19 antibody of the present invention is expressed in cells that express beta (1,4)—N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999.

Screening antibodies for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278.

Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge Antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, U.S. Pat. Nos. 5,427,908, 5,580,717, assigned to Affymax; U.S. Pat. No. 5,885,793, assigned to Cambridge Antibody Technologies; U.S. Pat. No. 5,750,373, assigned to Genentech, U.S. Pat. Nos. 5,618,920, 5,595,898, 5,576,195, 5,698,435, 5,693,493, 5,698,417, assigned to Xoma, Colligan, supra; Ausubel, supra; or Sambrook, supra.

Antibodies of the present invention can also be prepared using at least one anti-IL-23p19 antibody encoding nucleic acid to provide transgenic animals or mammals, such as goats, cows, horses, sheep, rabbits and the like, that produce such antibodies in their milk. Such animals can be provided using known methods. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference.

Antibodies of the present invention can additionally be prepared using at least one anti-IL-23p19 antibody encoding nucleic acid to provide transgenic plants and cultured plant cells (e.g., but not limited to, tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and references cited therein. Thus, antibodies of the present invention can also be produced using transgenic plants, according to known methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein.

The antibodies of the invention can bind human IL-23p19 with a wide range of affinities ($K_D$). In a preferred embodiment, at least one mAb of the present invention can optionally bind human IL-23p19 with high affinity. For example, a human or other mAb can bind human IL-23p19 with a $K_D$ equal to or less than about $10^{-7}$ M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$, $10^{-14}$, $10^{-15}$ or any range or value therein, as determined by surface plasmon resonance or the Kinexa method, as practiced by those of skill in the art. In one embodiment, the antibodies of the invention bind human IL-23p19 with a $K_D$ between about 4 and about 4400 pM.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_{on}$, $K_{off}$) are preferably made with standardized solutions of antibody and antigen, and a standardized buffer, such as the buffer described herein.

Competitive assays can be performed with the antibody of the present invention in order to determine what proteins, antibodies, and other antagonists compete for binding to IL-23p19 with the antibody of the present invention and/or share the epitope region. These assays as readily known to those of ordinary skill in the art evaluate competition between antagonists or ligands for a limited number of binding sites on a protein, e.g., p19. The protein and/or antibody is immobilized or insolubilized before or after the competition and the sample bound to the p19 subunit is separated from the unbound sample, for example, by decanting (where the protein/antibody was preinsolubilized) or by centrifuging (where the protein/antibody was precipitated after the competitive reaction). Also, the competitive binding may be determined by whether function is altered by the binding or lack of binding of the antibody to the protein, e.g., whether the antibody molecule inhibits or potentiates the enzymatic activity of, for example, a label. ELISA and other functional assays may be used, as well known in the art.

Certain embodiments of the anti-IL-23p19 antibodies of the invention have the sequences shown in the Sequence Tables below. For example, an anti-IL-23p19 antibody of the invention has one of the light chain CDR1 sequences of SEQ ID NOS:46-51; one of the light chain CDR2 sequences of SEQ ID NOS:52-57; one of the light chain CDR3 sequences of SEQ ID NOS:58-79; one of the heavy chain CDR1 sequences SEQ ID NOS:1-6; one of the heavy chain CDR2 sequences SEQ ID NOS:7-39 and 146; and/or one of the heavy chain CDR3 sequences SEQ ID NOS:40-45.

Nucleic Acid Molecules

Using the information provided herein, for example, the nucleotide sequences encoding at least 70-100% of the contiguous amino acids of at least one of the light chain variable regions of the antibodies of the invention (e.g., SEQ ID NOS: 136-138 and 142-144) and at least one of the heavy chain variable regions of the antibodies of the invention (e.g., SEQ ID NOS:133-135 and 139-141), specified fragments, variants or consensus sequences thereof, or a deposited vector comprising at least one of these sequences, a nucleic acid molecule of the present invention encoding at least one anti-IL-23p19 antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally, with one or more introns, e.g., but not limited to, at least one specified portion of at least one CDR, such as CDR1, CDR2 and/or CDR3 of at least light chain (SEQ ID NOS: 46-51, 52-57, or 58-79) or at least one heavy chain (SEQ ID NOS: 1-6, 7-39, or 40-45); nucleic acid molecules comprising the coding sequence for an anti-IL-23p19 antibody or variable region (e.g., light chain variable regions of SEQ ID NOS: 82-85, 93-98, 100, 102, 113-116, and 128-132 and heavy chain variable regions of SEQ ID NOS: 80, 81, 86-92, 99, 101, 103-112, 117-127, and 147); and nucleic acid molecules which comprise a nucleotide sequence substantially different from those described above but which, due to the degeneracy of the genetic code, still encode at least one anti-IL-23p19 antibody as described herein and/or as known in the art. Of course, the genetic code is well known in the art. Thus, it would be routine for one skilled in the art to generate such degenerate nucleic acid variants that code for specific anti-IL-23p19 antibodies of the present invention. See, e.g., Ausubel, et al., supra, and such nucleic acid variants are included in the present invention.

As indicated herein, nucleic acid molecules of the present invention which comprise a nucleic acid encoding an anti-IL-23p19 antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides Selectively Hybridizing to a Polynucleotide as Described Herein

The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids

The isolated nucleic acids of the present invention can be made using
(a) recombinant methods, (b) synthetic techniques, (c) purification techniques, and/or (d) combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, are well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention further provides recombinant expression cassettes comprising a nucleic acid of the present invention. A nucleic acid sequence of the present invention, for example, a cDNA or a genomic sequence encoding an antibody of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in the intron) of a non-heterologous form of a polynucleotide of the present invention so as to up or down regulate expression of a polynucleotide of the present invention. For example, endogenous promoters can be altered in vivo or in vitro by mutation, deletion and/or substitution.

Vectors and Host Cells

The present invention also relates to vectors that include isolated nucleic acid molecules of the present invention, host cells that are genetically engineered with the recombinant vectors, and the production of at least one anti-IL-23p19 antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the present invention. Alternatively, nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of an Antibody

An anti-IL-23p19 antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Anti-IL-23p19 Antibodies

An anti-IL-23p19 antibody according to the present invention includes any protein or peptide containing molecule that comprises at least a portion of an immunoglobulin molecule, such as but not limited to, at least one ligand binding portion (LBP), such as but not limited to, a complementarity determining region (CDR) of a heavy or light chain or a ligand binding portion thereof, a heavy chain or light chain variable region, a framework region (e.g., FR1, FR2, FR3, FR4 or fragment thereof, further optionally comprising at least one substitution, insertion or deletion), a heavy chain or light chain constant region, (e.g., comprising at least one CH1, hinge1, hinge2, hinge3, hinge4, CH2, or CH3 or fragment thereof, further optionally comprising at least one substitution, insertion or deletion), or any portion thereof, that can be incorporated into an antibody of the present invention. An antibody of the invention can include or be derived from any mammal, such as but not limited to, a human, a mouse, a rabbit, a rat, a rodent, a primate, or any combination thereof, and the like.

The isolated antibodies of the present invention comprise the antibody amino acid sequences disclosed herein encoded by any suitable polynucleotide, or any isolated or prepared antibody. Preferably, the human antibody or antigen-binding fragment binds human IL-23p19 and, thereby, partially or substantially neutralizes at least one biological activity of the protein. An antibody, or specified portion or variant thereof, that partially or preferably substantially neutralizes at least one biological activity of at least one IL-23 protein or fragment can bind the protein or fragment and thereby inhibit activities mediated through the binding of IL-23 to the IL-23 receptor or through other IL-23-dependent or mediated mechanisms. As used herein, the term "neutralizing antibody" refers to an antibody that can inhibit an IL-23-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-IL-23p19 antibody to inhibit an IL-23-dependent activity is preferably assessed by at least one suitable IL-23 protein or receptor assay, as described herein and/or as known in the art. A human antibody of the invention can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4 (e.g., γ1, γ2, γ3, or γ4). Antibodies of this type can be prepared by employing a transgenic mouse or other trangenic non-human mammal comprising at least one human light chain (e.g., IgG, IgA, and IgM) transgenes as described herein and/or as known in the art. In another embodiment, the anti-human IL-23p19 antibody comprises an IgG1 heavy chain and an IgG1 light chain.

At least one antibody of the invention binds at least one specified epitope specific to at least one IL-23p19 protein, subunit, fragment, portion or any combination thereof. The at least one epitope can comprise at least one antibody binding region that comprises at least one portion of the protein, which epitope is preferably comprised of at least one extracellular, soluble, hydrophillic, external or cytoplasmic portion of the protein. The at least one specified epitope can comprise any combination of at least one amino acid sequence of at least 1-3 amino acids to the entire specified portion of contiguous amino acids of amino acid residues 93-105 of SEQ ID NO:145 (that contains the initial 19 amino acid signal sequence for the p19 protein subunit) (or amino acid residues 74-86 of the p19 sequence without inclusion of the signal sequence), for example, amino acid residues 93, 93-94, 93-95, 93-96, 97-99, 100-102 of SEQ ID NO:145, etc. that include any portions or combinations of these sequences.

Generally, the antibody or antigen-binding fragment of the present invention will comprise an antigen-binding region that comprises at least one complementarity determining region (CDR1, CDR2 and CDR3) or variant of at least one heavy chain variable region and at least one complementarity determining region (CDR1, CDR2 and CDR3) or variant of at least one light chain variable region. Optionally, the CDR sequences may be derived from human germline sequences or closely match the germline sequences. For example, the CDRs from a synthetic library derived from the original mouse CDRs can be used. As a non-limiting example, the antibody or antigen-binding portion or variant can comprise at least one of the heavy chain CDR3, e.g., selected from SEQ ID NOS: 1-6, 7-39 and 146, or 40-45, and/or a light chain CDR3, e.g., selected from SEQ ID NOS: SEQ ID NOS: 46-51, 52-57, or 58-79. In a particular embodiment, the antibody or antigen-binding fragment can have an antigen-binding region that comprises at least a portion of at least one heavy chain CDR (i.e., CDR1, CDR2 and/or CDR3) (e.g., those disclosed herein). In another particular embodiment, the antibody or antigen-binding portion or variant can have an antigen-binding region that comprises at least a portion of at least one light chain CDR (i.e., CDR1, CDR2 and/or CDR3) (e.g., those disclosed herein).

In a preferred embodiment, the three heavy chain CDRs and the three light chain CDRs of the antibody or antigen-binding fragment can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-IL-23p19 antibody can comprise at least one of a heavy or light chain variable region having a defined amino acid sequence. For example, in a preferred embodiment, the anti-IL-23p19 antibody comprises at least one of at least one heavy chain variable region optionally selected from SEQ ID NOS: 80, 81, 86-92, 99, 101, 103-112, 117-127, and 147 and/or at least one light chain variable region optionally selected from SEQ ID NOS: 82-85, 93-98, 100, 102, 113-116, and 128-132. Antibodies that bind to human IL-23p19 and that comprise a defined heavy or light chain variable region can be prepared using suitable methods. The antibody, specified portion or variant can be expressed using the encoding nucleic acid or portion thereof in a suitable host cell.

Amino Acid Codes

The amino acids that make up anti-IL-23p19 antibodies of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994). An anti-IL-23p19 antibody of the present invention can include one or more amino acid substitutions, deletions or additions, either from natural mutations or human manipulation, as specified herein. Amino acids in an anti-IL-23p19 antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085

(1989)). The latter procedure introduces single alanine mutations at every residue in the molecule. The resulting mutant molecules are then tested for biological activity, such as, but not limited to, at least one IL-23 neutralizing activity. Sites that are critical for antibody binding can also be identified by structural analysis, such as crystallization, nuclear magnetic resonance or photoaffinity labeling (Smith, et al., J. Mol. Biol. 224:899-904 (1992) and de Vos, et al., Science 255:306-312 (1992)).

Anti-IL-23p19 antibodies of the present invention can include, but are not limited to, at least one portion, sequence or combination selected from 5 to all of the contiguous amino acids of the variable region sequences of SEQ ID NOS: 82-85, 93-98, 100, 102, 113-116, and 128-132 and SEQ ID NOS: 80, 81, 86-92, 99, 101, 103-112, 117-127, and 147.

Non-limiting variants that can enhance or maintain at least one of the listed activities include, but are not limited to, any of the above polypeptides, further comprising at least one mutation corresponding to at least one substitution in the residues varied among the disclosed variant amino acid sequences.

An anti-IL-23p19 antibody can further optionally comprise a polypeptide with an amino acid sequence that varies from the sequences disclosed herein (e.g., one or more conservative substitutions from the sequences provided herein). Also, more specifically, the present invention comprises variants of the amino acid sequence of a light chain variable region of SEQ ID NOS: 82-85, 93-98, 100, 102, 113-116, and 128-132 or the amino acid sequence of a heavy chain variable region of SEQ ID NOS: 80, 81, 86-92, 99, 101, 103-112, 117-127, and 147.

As those of skill will appreciate, the present invention includes at least one biologically active antibody of the present invention. Biologically active antibodies have a specific activity at least 20%, 30%, or 40%, and, preferably, at least 50%, 60%, or 70%, and, most preferably, at least 80%, 90%, or 95%-1000% or more of that of the native (non-synthetic), endogenous or related and known antibody. Methods of assaying and quantifying measures of enzymatic activity and substrate specificity are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example, $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-Δ9-octadecanoate ($C_{18}$, oleate), all cis-Δ5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably, one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NHS), and the like. Activating groups that can react with thiols include, for example, maleimide, iodoacetyl, acryloyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example, a divalent $C_1$-$C_{12}$ group wherein one or more carbon atoms can be replaced by a heteroatom, such as oxygen, nitrogen or sulfur. Suitable linker moieties include, for example, tetraethylene glycol, —(CH$_2$)$_3$—, —NH—(CH$_2$)$_6$—NH—, —(CH$_2$)$_2$—NH— and —CH$_2$—O—CH$_2$—CH$_2$—O—CH$_2$—CH$_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl)carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate, as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147-153 (1992); Werlen et al., *Bioconjugate Chem.*, 5:411-417 (1994); Kumaran et al., *Protein Sci.* 6(10):2233-2241 (1997); Itoh et al., *Bioorg. Chem.*, 24(1): 59-68 (1996); Capellas et al., *Biotechnol. Bioeng.*, 56(4):456-463 (1997)), and the methods described in Hermanson, G. T., *Bioconjugate Techniques*, Academic Press: San Diego, Calif. (1996).

Anti-Idiotype Antibodies to Anti-IL-23p19 Antibody Compositions

In addition to monoclonal anti-IL-23p19 antibodies, the present invention is also directed to an anti-idiotypic (anti-Id) antibody specific for such antibodies of the invention. An anti-Id antibody is an antibody which recognizes unique determinants generally associated with the antigen-binding region of another antibody. The anti-Id can be prepared by immunizing an animal of the same species and genetic type (e.g., mouse strain) as the source of the Id antibody with the antibody or a CDR containing region thereof. The immunized animal will recognize and respond to the idiotypic determinants of the immunizing antibody and produce an anti-Id antibody. The anti-Id antibody may also be used as an "immunogen" to induce an immune response in yet another animal, producing a so-called anti-anti-Id antibody.

The present invention also provides at least one anti-IL-23p19 antibody composition comprising at least one, at least two, at least three, at least four, at least five, at least six or more anti-IL-23p19 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-IL-23p19 antibody amino acid sequence selected from the group consisting of 70-100% of the contiguous amino acids of SEQ ID NOS:1-132, 146, and 147, or specified fragments, domains or variants thereof. Preferred anti-IL-23p19 antibody compositions include at least one or two full length, fragments, domains or variants of at least one CDR or LBP containing portions of the anti-IL-23p19 antibody sequence described herein, for example, 70-100% of SEQ ID NOS:1-132, 146, and 147, or specified fragments, domains or variants thereof. Further preferred compositions comprise, for example, 40-99% of at least one of 70-100% of SEQ ID NOS:1-132, 146, and 147, or specified fragments, domains or variants thereof. Such composition percentages are by weight, volume, concentration, molarity, or molality as liquid or dry solutions, mixtures, suspension, emulsions, particles, powder, or colloids, as known in the art or as described herein.

Antibody Compositions Comprising Further Therapeutically Active Ingredients

The antibody compositions of the invention can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see, e.g., Nursing 2001 Handbook of Drugs, 21$^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

The anti-infective drug can be at least one selected from amebicides or at least one of antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, and miscellaneous anti-infectives. The CV drug can be at least one selected from inotropics, antiarrhythmics, antianginals, antihypertensives, antilipemics, and miscellaneous cardiovascular drugs. The CNS drug can be at least one selected from normarcotic analgesics or at least one selected from antipyretics, nonsteroidal anti-inflammatory drugs, narcotic or at least one opiod analgesics, sedative-hypnotics, anticonvulsants, antidepressants, antianxiety drugs, antipsychotics, central nervous system stimulants, antiparkinsonians, and miscellaneous central nervous system drugs. The ANS drug can be at least one selected from cholinergics (parasympathomimetics), anticholinergics, adrenergics (sympathomimetics), adrenergic blockers (sympatholytics), skeletal muscle relaxants, and neuromuscular blockers. The respiratory tract drug can be at least one selected from antihistamines, bronchodilators, expectorants or at least one antitussive, and miscellaneous respiratory drugs. The GI tract drug can be at least one selected from antacids or at least one adsorbent or at least one antiflatulent, digestive enzyme or at least one gallstone solubilizer, antidiarrheals, laxatives, antiemetics, and antiulcer drugs. The hormonal drug can be at least one selected from corticosteroids, androgens or at least one anabolic steroid, estrogen or at least one progestin, gonadotropin, antidiabetic drug or at least one glucagon, thyroid hormone, thyroid hormone antagonist, pituitary hormone, and parathyroid-like drug. The drug for fluid and electrolyte balance can be at least one selected from diuretics, electrolytes or at least one replacement solution, acidifier or at least one alkalinizer. The hematologic drug can be at least one selected from hematinics, anticoagulants, blood derivatives, and thrombolytic enzymes. The antineoplastics can be at least one selected from alkylating drugs, antimetabolites, antibiotic antineoplastics, antineoplastics that alter hormone balance, and miscellaneous antineoplastics. The immunomodulation drug can be at least one selected from immunosuppressants, vaccines or at least one toxoid, antitoxin or at least one antivenin, immune serum, and biological response modifier. The ophthalmic, otic, and nasal drugs can be at least one selected from ophthalmic anti-infectives, ophthalmic anti-inflammatories, miotics, mydriatics, ophthalmic vasoconstrictors, miscellaneous ophthalmics, otics, and nasal drugs. The topical drug can be at least one selected from local anti-infectives, scabicides or at least one pediculicide or topical corticosteroid. The nutritional drug can be at least one selected from vitamins, minerals, or calorics. See, e.g., contents of Nursing 2001 Drug Handbook, supra.

The at least one amebicide or antiprotozoal can be at least one selected from atovaquone, chloroquine hydrochloride, chloroquine phosphate, metronidazole, metronidazole hydrochloride, and pentamidine isethionate. The at least one anthelmintic can be at least one selected from mebendazole, pyrantel pamoate, and thiabendazole. The at least one antifungal can be at least one selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin, and terbinafine hydrochloride. The at least one antimalarial can be at least one selected from chloroquine hydrochloride, chloroquine phosphate, doxycycline, hydroxychloroquine sulfate, mefloquine hydrochloride, primaquine phosphate, pyrimethamine, and pyrimethamine with sulfadoxine. The at least one antitubercolotic or antileprotic can be at least one selected from clofazimine, cycloserine, dapsone, ethambutol hydrochloride, isoniazid, pyrazinamide, rifabutin, rifampin, rifapentine, and streptomycin sulfate. The at least one aminoglycoside can be at least one selected from amikacin sulfate, gentamicin sulfate, neomycin sulfate, streptomycin sulfate, and tobramycin sulfate. The at least one penicillin can be at least one selected from amoxcillin/clavulanate potassium, amoxicillin trihydrate, ampicillin, ampicillin sodium, ampicillin trihydrate, ampicillin sodium/sulbactam sodium, cloxacillin sodium, dicloxacillin sodium, mezlocillin sodium, nafcillin sodium, oxacillin sodium, penicillin G benzathine, penicillin G potassium, penicillin G procaine, penicillin G sodium, penicillin V potassium, piperacillin sodium, piperacillin sodium/tazobactam sodium, ticarcillin disodium, and ticarcillin disodium/clavulanate potassium. The at least one cephalosporin can be at least one selected from cefaclor, cefadroxil, cefazolin sodium, cefdinir, cefepime hydrochloride, cefixime, cefinetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, and loracarbef. The at least one tetracycline can, be at least one selected from demeclocycline hydrochloride, doxycycline calcium, doxycycline hyclate, doxycycline hydrochloride, doxycycline monohydrate, minocycline hydrochloride, and tetracycline hydrochloride. The at least one sulfonamide can be at least one selected from co-trimoxazole, sulfadiazine, sulfamethoxazole, sulfisoxazole, and sulfisoxazole acetyl. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, and trovafloxacin mesylate. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, and trovafloxacin mesylate. The at least one antiviral can be at least one selected from abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir, and zidovudine. The at least one macroline anti-infective can be at least one selected from azithromycin, clarithromycin, dirithromycin, erythromycin base, erythromycin estolate, erythromycin ethylsuccinate, erythromycin lactobionate, and erythromycin stearate. The at least one miscellaneous anti-infective can be at least one selected from aztreonam, bacitracin, chloramphenicol sodium sucinate, clindamycin hydrochloride, clindamycin palmitate hydrochloride, clindamycin phosphate, imipenem and cilastatin sodium, meropenem, nitrofurantoin macrocrystals, nitrofurantoin microcrystals, quinupristin/dalfopristin, spectinomycin hydrochloride, trimethoprim, and vancomycin hydrochloride. (See, e.g., pp. 24-214 of Nursing 2001 Drug Handbook.)

The at least one inotropic can be at least one selected from aminone lactate, digoxin, and milrinone lactate. The at least one antiarrhythmic can be at least one selected from adenosine, amiodarone hydrochloride, atropine sulfate, bretylium tosylate, diltiazem hydrochloride, disopyramide, disopyramide phosphate, esmolol hydrochloride, flecamide acetate, ibutilide fumarate, lidocaine hydrochloride, mexiletine hydrochloride, moricizine hydrochloride, phenyloin, phenyloin sodium, procainamide hydrochloride, propafenone hydrochloride, propranolol hydrochloride, quinidine bisulfate, quinidine gluconate, quinidine polygalacturonate, quinidine sulfate, sotalol, tocamide hydrochloride, and verapamil hydrochloride. The at least one antianginal can be at least one selected from amlodipidine besylate, amyl nitrite, bepridil hydrochloride, diltiazem hydrochloride, isosorbide dinitrate, isosorbide mononitrate, nadolol, nicardipine hydrochloride, nifedipine, nitroglycerin, propranolol hydrochloride, verapamil, and verapamil hydrochloride. The at least one antihypertensive can be at least one selected from acebutolol hydrochloride, amlodipine besylate, atenolol, benazepril hydrochloride, betaxolol hydrochloride, bisoprolol fumarate, candesartan cilexetil, captopril, carteolol hydrochloride, carvedilol, clonidine, clonidine hydrochloride, diazoxide, diltiazem hydrochloride, doxazosin mesylate, enalaprilat, enalapril maleate, eprosartan mesylate, felodipine, fenoldopam mesylate, fosinopril sodium, guanabenz acetate, guanadrel sulfate, guanfacine hydrochloride, hydralazine hydrochloride, irbesartan, isradipine, labetalol hydrchloride, lisinopril, losartan potassium, methyldopa, methyldopate hydrochloride, metoprolol succinate, metoprolol tartrate, minoxidil, moexipril hydrochloride, nadolol, nicardipine hydrochloride, nifedipine, nisoldipine, nitroprusside sodium, penbutolol sulfate, perindopril erbumine, phentolamine mesylate, pindolol, prazosin hydrochloride, propranolol hydrochloride, quinapril hydrochloride, ramipril, telmisartan, terazosin hydrochloride, timolol maleate, trandolapril, valsartan, and verapamil hydrochloride. The at least one antilipemic can be at least one selected from atorvastatin calcium, cerivastatin sodium, cholestyramine, colestipol hydrochloride, fenofibrate (micronized), fluvastatin sodium, gemfibrozil, lovastatin, niacin, pravastatin sodium, and simvastatin. The at least one miscellaneous CV drug can be at least one selected from abciximab, alprostadil, arbutamine hydrochloride, cilostazol, clopidogrel bisulfate, dipyridamole, eptifibatide, midodrine hydrochloride, pentoxifylline, ticlopidine hydrochloride, and tirofiban hydrochloride. (See, e.g., pp. 215-336 of Nursing 2001 Drug Handbook.)

The at least one normarcotic analgesic or antipyretic can be at least one selected from acetaminophen, aspirin, choline magnesium trisalicylate, diflunisal, and magnesium salicylate. The at least one nonsteroidal anti-inflammatory drug can be at least one selected from celecoxib, diclofenac potassium, diclofenac sodium, etodolac, fenoprofen calcium, flurbiprofen, ibuprofen, indomethacin, indomethacin sodium trihydrate, ketoprofen, ketorolac tromethamine, nabumetone, naproxen, naproxen sodium, oxaprozin, piroxicam, rofecoxib, and sulindac. The at least one narcotic or opiod analgesic can be at least one selected from alfentanil hydrochloride, buprenorphine hydrochloride, butorphanol tartrate, codeine phosphate, codeine sulfate, fentanyl citrate, fentanyl transdermal system, fentanyl transmucosal, hydromorphone hydrochloride, meperidine hydrochloride, methadone hydrochloride, morphine hydrochloride, morphine sulfate, morphine tartrate, nalbuphine hydrochloride, oxycodone hydrochloride, oxycodone pectinate, oxymorphone hydrochloride, pentazocine hydrochloride, pentazocine hydrochloride and naloxone hydrochloride, pentazocine lactate, propoxyphene hydrochloride, propoxyphene napsylate, remifentanil hydrochloride, sufentanil citrate, and tramadol hydrochloride. The at least one sedative-hypnotic can be at least one selected from chloral hydrate, estazolam, flurazepam hydrochloride, pentobarbital, pentobarbital sodium, phenobarbital sodium, secobarbital sodium, temazepam, triazolam, zaleplon, and zolpidem tartrate. The at least one anticonvulsant can be at least one selected from acetazolamide sodium, carbamazepine, clonazepam, clorazepate dipotassium, diazepam, divalproex sodium, ethosuximde, fosphenyloin sodium, gabapentin, lamotrigine, magnesium sulfate, phenobarbital, phenobarbital sodium, phenyloin, phenyloin sodium, phenyloin sodium (extended), primidone, tiagabine hydrochloride, topiramate, valproate sodium, and valproic acid. The at least one antidepressant can be at least one selected from amitriptyline hydrochloride, amitriptyline pamoate, amoxapine, bupropion hydrochloride, citalopram hydrobromide, clomipramine hydrochloride, desipramine hydrochloride, doxepin hydrochloride, fluoxetine hydrochloride, imipramine hydrochloride, imipramine pamoate, mirtazapine, nefazodone hydrochloride, nortriptyline hydrochloride, paroxetine hydrochloride, phenelzine sulfate, sertraline hydrochloride, tranylcypromine sulfate, trimipramine maleate, and venlafaxine hydrochloride. The at least one antianxiety drug can be at least one selected from alprazolam, buspirone hydrochloride, chlordiazepoxide, chlordiazepoxide hydrochloride, clorazepate dipotassium, diazepam, doxepin hydrochloride, hydroxyzine embonate, hydroxyzine hydrochloride, hydroxyzine pamoate, lorazepam, mephrobamate, midazolam hydrochloride, and oxazepam. The at least one antipsychotic drug can be at least one selected from chlorpromazine hydrochloride, clozapine, fluphenazine decanoate, fluephenazine enanthate, fluphenazine hydrochloride, haloperidol, haloperidol decanoate, haloperidol lactate, loxapine hydrochloride, loxapine succinate, mesoridazine besylate, molindone hydrochloride, olanzapine, perphenazine, pimozide, prochlorperazine, quetiapine fumarate, risperidone, thioridazine hydrochloride, thiothixene, thiothixene hydrochloride, and trifluoperazine hydrochloride. The at least one central nervous system stimulant can be at least one selected from amphetamine sulfate, caffeine, dextroamphetamine sulfate, doxapram hydrochloride, methamphetamine hydrochloride, methylphenidate hydrochloride, modafinil, pemoline, and phentermine hydrochloride. The at least one antiparkinsonian can be at least one selected from amantadine hydrochloride, benztropine mesylate, biperiden hydrochloride, biperiden lactate, bromocriptine mesylate, carbidopa-levodopa, entacapone, levodopa, pergolide mesylate, pramipexole dihydrochloride, ropinirole hydrochloride, selegiline hydrochloride, tolcapone, and trihexyphenidyl hydrochloride. The at least one miscellaneous central nervous system drug can be at least one selected from bupropion hydrochloride, donepezil hydrochloride, droperidol, fluvoxamine maleate, lithium carbonate, lithium citrate, naratriptan hydrochloride, nicotine polacrilex, nicotine transdermal system, propofol, rizatriptan benzoate, sibutramine hydrochloride monohydrate, sumatriptan succinate, tacrine hydrochloride, and zolmitriptan. (See, e.g., pp. 337-530 of Nursing 2001 Drug Handbook.)

The at least one cholinergic (e.g., parasymathomimetic) can be at least one selected from bethanechol chloride, edrophonium chloride, neostigmine bromide, neostigmine methylsulfate, physostigmine salicylate, and pyridostigmine bromide. The at least one anticholinergic can be at least one selected from atropine sulfate, dicyclomine hydrochloride, glycopyrrolate, hyoscyamine, hyoscyamine sulfate, propantheline bromide, scopolamine, scopolamine butylbromide, and scopolamine hydrobromide. The at least one adrenergic (sympathomimetics) can be at least one selected from dobutamine hydrochloride, dopamine hydrochloride, metaraminol bitartrate, norepinephrine bitartrate, phenylephrine hydrochloride, pseudoephedrine hydrochloride, and pseudoephedrine sulfate. The at least one adrenergic blocker (sympatholytic) can be at least one selected from dihydroergotamine mesylate, ergotamine tartrate, methysergide maleate, and propranolol hydrochloride. The at least one skeletal muscle relaxant can be at least one selected from baclofen, carisoprodol, chlorzoxazone, cyclobenzaprine hydrochloride, dantrolene sodium, methocarbamol, and tizanidine hydrochloride. The at least one neuromuscular blocker,can be at least one selected from atracurium besylate, cisatracurium besylate, doxacurium chloride, mivacurium chloride, pancuronium bromide, pipecuronium bromide, rapacuronium bromide, rocuronium bromide, succinylcholine chloride, tubocurarine chloride, and vecuronium bromide. (See, e.g., pp. 531-84 of Nursing 2001 Drug Handbook.)

The at least one antihistamine can be at least one selected from brompheniramine maleate, cetirizine hydrochloride, chlorpheniramine maleate, clemastine fumarate, cyproheptadine hydrochloride, diphenhydramine hydrochloride, fexofenadine hydrochloride, loratadine, promethazine hydrochloride, promethazine theoclate, and triprolidine hydrochloride. The at least one bronchodilator can be at least one selected from albuterol, albuterol sulfate, aminophylline, atropine sulfate, ephedrine sulfate, epinephrine, epinephrine bitartrate, epinephrine hydrochloride, ipratropium bromide, isoproterenol, isoproterenol hydrochloride, isoproterenol sulfate, levalbuterol hydrochloride, metaproterenol sulfate, oxtriphylline, pirbuterol acetate, salmeterol xinafoate, terbutaline sulfate, and theophylline. The at least one expectorant or antitussive can be at least one selected from benzonatate, codeine phosphate, codeine sulfate, dextramethorphan hydrobromide, diphenhydramine hydrochloride, guaifenesin, and hydromorphone hydrochloride. The at least one miscellaneous respiratory drug can be at least one selected from acetylcysteine, beclomethasone dipropionate, beractant, budesonide, calfactant, cromolyn sodium, dornase alfa, epoprostenol sodium, flunisolide, fluticasone propionate, montelukast sodium, nedocromil sodium, palivizumab, triamcinolone acetonide, zafirlukast, and zileuton. (See, e.g., pp. 585-642 of Nursing 2001 Drug Handbook.)

The at least one antacid, adsorbent, or antiflatulent can be at least one selected from aluminum carbonate, aluminum hydroxide, calcium carbonate, magaldrate, magnesium hydroxide, magnesium oxide, simethicone, and sodium bicarbonate. The at least one digestive enzyme or gallstone solubilizer can be at least one selected from pancreatin, pancrelipase, and ursodiol. The at least one antidiarrheal can be at least one selected from attapulgite, bismuth subsalicylate, calcium polycarbophil, diphenoxylate hydrochloride and atropine sulfate, loperamide, octreotide acetate, opium tincture, and opium tincure (camphorated). The at least one laxative can be at least one selected from bisocodyl, calcium polycarbophil, cascara sagrada, cascara sagrada aromatic fluidextract, cascara sagrada fluidextract, castor oil, docusate calcium, docusate sodium, glycerin, lactulose, magnesium citrate, magnesium hydroxide, magnesium sulfate, methylcellulose, mineral oil, polyethylene glycol or electrolyte solution, psyllium, senna, and sodium phosphates. The at least one antiemetic can be at least one selected from chlorpromazine hydrochloride, dimenhydrinate, dolasetron mesylate, dronabinol, granisetron hydrochloride, meclizine hydrochloride, metocloproamide hydrochloride, ondansetron hydrochloride, perphenazine, prochlorperazine, prochlorperazine edisylate, prochlorperazine maleate, promethazine hydrochloride, scopolamine, thiethylperazine maleate, and trimethobenzamide hydrochloride. The at least one antiulcer drug can be at least one selected from cimetidine, cimetidine hydrochloride, famotidine, lansoprazole, misoprostol, nizatidine, omeprazole, rabeprozole sodium, rantidine bismuth citrate, ranitidine hydrochloride, and sucralfate. (See, e.g., pp. 643-95 of Nursing 2001 Drug Handbook.)

The at least one corticosteroid can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, and triamcinolone diacetate. The at least one androgen or anabolic steroid can be at least one selected from danazol, fluoxymesterone, methyltestosterone, nandrolone decanoate, nandrolone phenpropionate, testosterone, testosterone cypionate, testosterone enanthate, testosterone propionate, and testosterone transdermal system. The at least one estrogen or progestin can be at least one selected from esterified estrogens, estradiol, estradiol cypionate, estradiol/norethindrone acetate transdermal system, estradiol valerate, estrogens (conjugated), estropipate, ethinyl estradiol, ethinyl estradiol and desogestrel, ethinyl estradiol and ethynodiol diacetate, ethinyl estradiol and desogestrel, ethinyl estradiol and ethynodiol diacetate, ethinyl estradiol and levonorgestrel, ethinyl estradiol and norethindrone, ethinyl estradiol and norethindrone acetate, ethinyl estradiol and norgestimate, ethinyl estradiol and norgestrel, ethinyl estradiol and norethindrone and acetate and ferrous fumarate, levonorgestrel, medroxyprogesterone acetate, mestranol and norethindron, norethindrone, norethindrone acetate, norgestrel, and progesterone. The at least one gonadroptropin can be at least one selected from ganirelix acetate, gonadoreline acetate, histrelin acetate, and menotropins. The at least one antidiabetic or glucaon can be at least one selected from acarbose, chlorpropamide, glimepiride, glipizide, glucagon, glyburide, insulins, metformin hydrochloride, miglitol, pioglitazone hydrochloride, repaglinide, rosiglitazone maleate, and troglitazone. The at least one thyroid hormone can be at least one selected from levothyroxine sodium, liothyronine sodium, liotrix, and thyroid. The at least one thyroid hormone antagonist can be at least one selected from methimazole, potassium iodide, potassium iodide (saturated solution), propylthiouracil, radioactive iodine (sodium iodide $^{131}$I, and strong iodine solution. The at least one pituitary hormone can be at least one selected from corticotropin, cosyntropin, desmophressin acetate, leuprolide acetate, repository corticotropin, somatrem, somatropin, and vasopressin. The at least one parathyroid-like drug can be at least one selected from calcifediol, calcitonin (human), calcitonin (salmon), calcitriol, dihydrotachysterol, and etidronate disodium. (See, e.g., pp. 696-796 of Nursing 2001 Drug Handbook.)

The at least one diuretic can be at least one selected from acetazolamide, acetazolamide sodium, amiloride hydrochloride, bumetanide, chlorthalidone, ethacrynate sodium, ethacrynic acid, furosemide, hydrochlorothiazide, indapamide, mannitol, metolazone, spironolactone, torsemide, triamterene, and urea. The at least one electrolyte or replacement solution can be at least one selected from calcium acetate, calcium carbonate, calcium chloride, calcium citrate, calcium glubionate, calcium gluceptate, calcium gluconate, calcium lactate, calcium phosphate (dibasic), calcium phosphate (tribasic), dextran (high-molecular-weight), dextran (low-molecular-weight), hetastarch, magnesium chloride, magnesium sulfate, potassium acetate, potassium bicarbonate, potassium chloride, potassium gluconate, Ringer's injection, Ringer's injection (lactated), and sodium chloride. The at least one acidifier or alkalinizer can be at least one selected from sodium bicarbonate, sodium lactate, and tromethamine. (See, e.g., pp. 797-833 of Nursing 2001 Drug Handbook.)

The at least one hematinic can be at least one selected from ferrous fumarate, ferrous gluconate, ferrous sulfate, ferrous sulfate (dried), iron dextran, iron sorbitol, polysaccharide-iron complex, and sodium ferric gluconate complex. The at least one anticoagulant can be at least one selected from ardeparin sodium, dalteparin sodium, danaparoid sodium, enoxaparin sodium, heparin calcium, heparin sodium, and warfarin sodium. The at least one blood derivative can be at least one selected from albumin 5%, albumin 25%, antihemophilic factor, anti-inhibitor coagulant complex, antithrombin III (human), factor IX (human), factor IX complex, and plasma protein fractions. The at least one thrombolytic enzyme can be at least one selected from alteplase, anistreplase, reteplase (recombinant), streptokinase, and urokinase. (See, e.g., pp. 834-66 of Nursing 2001 Drug Handbook.)

The at least one alkylating drug can be at least one selected from busulfan, carboplatin, carmustine, chlorambucil, cisplatin, cyclophosphamide, ifosfamide, lomustine, mechlorethamine hydrochloride, melphalan, melphalan hydrochloride, streptozocin, temozolomide, and thiotepa. The at least one antimetabolite can be at least one selected from capecitabine, cladribine, cytarabine, floxuridine, fludarabine phosphate, fluorouracil, hydroxyurea, mercaptopurine, methotrexate, methotrexate sodium, and thioguanine. The at least one antibiotic antineoplastic can be at least one selected from bleomycin sulfate, dactinomycin, daunorubicin citrate liposomal, daunorubicin hydrochloride, doxorubicin hydrochloride, doxorubicin hydrochloride liposomal, epirubicin hydrochloride, idarubicin hydrochloride, mitomycin, pentostatin, plicamycin, and valrubicin. The at least one antineoplastic that alters hormone balance can be at least one selected from anastrozole, bicalutamide, estramustine phosphate sodium, exemestane, flutamide, goserelin acetate, letrozole, leuprolide acetate, megestrol acetate, nilutamide, tamoxifen citrate, testolactone, and toremifene citrate. The at least one miscellaneous antineoplastic can be at least one selected from asparaginase, *bacillus* Calmette-Guerin (BCG) (live intravesical), dacarbazine, docetaxel, etoposide, etoposide phosphate, gemcitabine hydrochloride, irinotecan hydrochloride, mitotane, mitoxantrone hydrochloride, paclitaxel, pegaspargase, porfimer sodium, procarbazine hydrochloride, rituximab, teniposide, topotecan hydrochloride, trastuzumab, tretinoin, vinblastine sulfate, vincristine sulfate, and vinorelbine tartrate. (See, e.g., pp. 867-963 of *Nursing* 2001 *Drug Handbook.*)

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, and tacrolimus. The at least one vaccine or toxoid can be at least one selected from BCG vaccine, cholera vaccine, diphtheria and tetanus toxoids (adsorbed), diphtheria and tetanus toxoids and acellular pertussis vaccine adsorbed, diphtheria and tetanus toxoids and whole-cell pertussis vaccine, *Haemophilus* b conjugate vaccines, hepatitis A vaccine (inactivated), hepatisis B vaccine (recombinant), influenza virus vaccine 1999-2000 trivalent types A & B (purified surface antigen), influenza virus vaccine 1999-2000 trivalent types A & B (subvirion or purified subvirion), influenza virus vaccine 1999-2000 trivalent types A & B (whole virion), Japanese encephalitis virus vaccine (inactivated), Lyme disease vaccine (recombinant OspA), measles and mumps and rubella virus vaccine (live), measles and mumps and rubella virus vaccine (live attenuated), measles virus vaccine (live attenuated), meningococcal polysaccharide vaccine, mumps virus vaccine (live), plague vaccine, pneumococcal vaccine (polyvalent), poliovirus vaccine (inactivated), poliovirus vaccine (live, oral, trivalent), rabies vaccine (adsorbed), rabies vaccine (human diploid cell), rubella and mumps virus vaccine (live), rubella virus vaccine (live, attenuated), tetanus toxoid (adsorbed), tetanus toxoid (fluid), typhoid vaccine (oral), typhoid vaccine (parenteral), typhoid Vi polysaccharide vaccine, varicella virus vaccine, and yellow fever vaccine. The at least one antitoxin or antivenin can be at least one selected from black widow spider antivenin, Crotalidae antivenom (polyvalent), diphtheria antitoxin (equine), and *Micrurus fulvius* antivenin. The at least one immune serum can be at least one selected from cytomegalovirus immune globulin (intraveneous), hepatitis B immune globulin (human), immune globulin intramuscular, immune globulin intravenous, rabies immune globulin (human), respiratory syncytial virus immune globulin intravenous (human), Rh$_O$(D) immune globulin (human), Rh$_O$(D) immune globulin intravenous (human), tetanus immune globulin (human), and varicella-zoster immune globulin. The at least one biological response modifier can be at least one selected from aldesleukin, epoetin alfa, filgrastim, glatiramer acetate for injection, interferon alfacon-1, interferon alfa-2a (recombinant), interferon alfa-2b (recombinant), interferon beta-1a, interferon beta-1b (recombinant), interferon gamma-1b, levamisole hydrochloride, oprelvekin, and sargramostim. (See, e.g., pp. 964-1040 of *Nursing* 2001 *Drug Handbook.*)

The at least one ophthalmic anti-infective can be selected form bacitracin, chloramphenicol, ciprofloxacin hydrochloride, erythromycin, gentamicin sulfate, ofloxacin 0.3%, polymyxin B sulfate, sulfacetamide sodium 10%, sulfacetamide sodium 15%, sulfacetamide sodium 30%, tobramycin, and vidarabine. The at least one ophthalmic anti-inflammatory can be at least one selected from dexamethasone, dexamethasone sodium phosphate, diclofenac sodium 0.1%, fluorometholone, flurbiprofen sodium, ketorolac tromethamine, prednisolone acetate (suspension) and prednisolone sodium phosphate (solution). The at least one miotic can be at least one selected from acetylocholine chloride, carbachol (intraocular), carbachol (topical), echothiophate iodide, pilocarpine, pilocarpine hydrochloride, and pilocarpine nitrate. The at least one mydriatic can be at least one selected from atropine sulfate, cyclopentolate hydrochloride, epinephrine hydrochloride, epinephryl borate, homatropine hydrobromide, phenylephrine hydrochloride, scopolamine hydrobromide, and tropicamide. The at least one ophthalmic vasoconstrictor can be at least one selected from naphazoline hydrochloride, oxymetazoline hydrochloride, and tetrahydrozoline hydrochloride. The at least one miscellaneous ophthalmic can be at least one selected from apraclonidine hydrochloride, betaxolol hydrochloride, brimonidine tartrate, carteolol hydrochloride, dipivefrin hydrochloride, dorzolamide hydrochloride, emedastine difumarate, fluorescein sodium, ketotifen fumarate, latanoprost, levobunolol hydrochloride, metipranolol hydrochloride, sodium chloride (hypertonic), and timolol maleate. The at least one otic can be at least one selected from boric acid, carbamide peroxide, chloramphenicol, and triethanolamine polypeptide oleate-condensate. The at least one nasal drug can be at least one selected from beclomethasone dipropionate, budesonide, ephedrine sulfate, epinephrine hydrochloride, flunisolide, fluticasone propionate, naphazoline hydrochloride, oxymetazoline hydrochloride, phenylephrine hydrochloride, tetrahydrozoline hydrochloride, triamcinolone acetonide, and xylometazoline hydrochloride. (See, e.g., pp. 1041-97 of *Nursing* 2001 *Drug Handbook.*)

The at least one local anti-infective can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, and tolnaftate. The at least one scabicide or pediculicide can be at least one selected from crotamiton, lindane, permethrin, and pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocorisone valerate, mometasone furoate, and triamcinolone acetonide. (See, e.g., pp. 1098-1136 of *Nursing* 2001 *Drug Handbook.*)

The at least one vitamin or mineral can be at least one selected from vitamin A, vitamin B complex, cyanocobalamin, folic acid, hydroxocobalamin, leucovorin calcium, niacin, niacinamide, pyridoxine hydrochloride, riboflavin, thiamine hydrochloride, vitamin C, vitamin D, cholecalciferol, ergocalciferol, vitamin D analogue, doxercalciferol, paricalcitol, vitamin E, vitamin K analogue, phytonadione, sodium fluoride, sodium fluoride (topical), trace elements, chromium, copper, iodine, manganese, selenium, and zinc. The at least one caloric can be at least one selected from amino acid infusions (crystalline), amino acid infusions in dextrose, amino acid infusions with electrolytes, amino acid infusions with electrolytes in dextrose, amino acid infusions for hepatic failure, amino acid infusions for high metabolic stress, amino acid infusions for renal failure, dextrose, fat emulsions, and medium-chain triglycerides. (See, e.g., pp. 1137-63 of *Nursing* 2001 *Drug Handbook*.)

Anti-IL-23p19 antibody compositions of the present invention can further comprise at least one of any suitable and effective amount of a composition or pharmaceutical composition comprising at least one anti-IL-23p19 antibody contacted or administered to a cell, tissue, organ, animal or patient in need of such modulation, treatment or therapy, optionally further comprising at least one selected from at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, etanercept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobul in, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Non-limiting examples of such cytokines include, but are not limited to, any of IL-1 to IL-28 (e.g., IL-1, IL-2, etc.). Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii,* and *Shigella sonnei*), *Salmonella* species (e.g., *Salmonella typhi, Salmonella cholerasuis, Salmonella enteritidis*), *Clostridium* species (e.g., *Clostridium perfringens, Clostridium difficile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa,* and *Streptococci.* See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, New York (1990); Berkow et al, eds., *The Merck Manual,* 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

Anti-IL-23p19 antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences,* $18^{th}$ Edition, Mack Publishing Co. (Easton, Pa.) 1990. Pharmaceutically acceptable carriers can be routinely selected that are suitable for the mode of administration, solubility and/or stability of the anti-IL-23p19 antibody, fragment or variant composition as well known in the art or as described herein.

Pharmaceutical excipients and additives useful in the present composition include, but are not limited to, proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Exemplary protein excipients include serum albumin, such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-IL-23p19 antibody compositions can also include a buffer or a pH-adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts, such as citrate.

Additionally, anti-IL-23p19 antibody compositions of the invention can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates, such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-IL-23p19 antibody, portion or variant compositions according to the invention are known in the art, e.g., as listed in "Remington: The Science & Practice of Pharmacy", $19^{th}$ ed., Williams & Williams, (1995), and in the "Physician's Desk Reference", $52^{nd}$ ed., a Medical Economics, Montvale, N.J. (1998), the Disclosures of which are entirely incorporated herein by reference. Preferred carrier or excipient materials are carbohydrates (e.g., saccharides and alditols) and buffers (e.g., citrate) or polymeric agents. An exemplary carrier molecule is the mucopolysaccharide, hyaluronic acid, which may be useful for intraarticular delivery.

Formulations

As noted above, the invention provides for stable formulations, which preferably comprise a phosphate buffer with saline or a chosen salt, as well as preserved solutions and formulations containing a preservative as well as multi-use preserved formulations suitable for pharmaceutical or veterinary use, comprising at least one anti-IL-23p19 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, polymers, or mixtures thereof in an aqueous diluent. Any suitable concentration or mixture can be used as known in the art, such as about 0.0015%, or any range, value, or fraction therein. Non-limiting examples include, no preservative, about 0.1-2% m-cresol (e.g., 0.2, 0.3. 0.4, 0.5, 0.9, 1.0%), about 0.1-3% benzyl alcohol (e.g., 0.5, 0.9, 1.1, 1.5, 1.9, 2.0, 2.5%), about 0.001-0.5% thimerosal (e.g., 0.005, 0.01), about 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one anti-IL-23p19 antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one anti-IL-23p19 antibody, and a second vial comprising an aqueous diluent of prescribed buffer or preservative, wherein said packaging material comprises a label that instructs a patient to reconstitute the at least one anti-IL-23p19 antibody in the aqueous diluent to form a solution that can be held over a period of twenty-four hours or greater.

The at least one anti-IL-23p19 antibody used in accordance with the present invention can be produced by recombinant means, including from mammalian cell or transgenic preparations, or can be purified from other biological sources, as described herein or as known in the art.

The range of at least one anti-IL-23p19 antibody in the product of the present invention includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g., isotonicity agents, buffers, antioxidants, and preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably, the formulations of the present invention have a pH between about 6.8 and about 7.8. Preferred buffers include phosphate buffers, most preferably, sodium phosphate, particularly, phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants, such as polysorbate 20 or 80 or poloxamer 184 or 188, Pluronic® polyls, other block co-polymers, and chelators, such as EDTA and EGTA, can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one anti-IL- 23p19 antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-IL-23p19 antibody and preservative in an aqueous diluent is carried out using conventional dissolution and mixing procedures. To prepare a suitable formulation, for example, a measured amount of at least one anti-IL-23p19 antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized at least one anti-IL-23p19 antibody that is reconstituted with a second vial containing water, a preservative and/or excipients, preferably, a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period ranging from immediate to twenty-four hours or greater. Accordingly, the presently claimed articles of manufacture offer significant advantages to the patient. Formulations of the invention can optionally be safely stored at temperatures of from about 2° C. to about 40° C. and retain the biological activity of the protein for extended periods of time, thus allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of at least one anti-IL-23p19 antibody of the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and, optionally, a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-IL-23p19 antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-IL-23p19 antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising single vial systems include pen-injector devices for delivery of a solution, such as BD Pens, BD Autojector®, Humaject®, NovoPen®, B-D®Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, e.g., as made or developed by Becton Dickensen (Franklin Lakes, N.J., www.bectondickenson.com), Disetronic (Burgdorf, Switzerland, www.disetronic.com; Bioject, Portland, Oreg. (www.bioject.com); National Medical Products, Weston Medical (Peterborough, UK, www.weston-medical.com), Medi-Ject Corp (Minneapolis, Minn., www.mediject.com), and similary suitable devices. Recognized devices comprising a dual vial system include those pen-injector systems for reconstituting a lyophilized drug in a cartridge for delivery of the reconstituted solution, such as the HumatroPen®. Examples of other devices suitable include pre-filled syringes, auto-injectors, needle free injectors and needle free IV infusion sets.

The products presently claimed include packaging material. The packaging material provides, in addition to the information required by the regulatory agencies, the conditions under which the product can be used. The packaging material of the present invention provides instructions to the patient to reconstitute the at least one anti-IL-23p19 antibody in the aqueous diluent to form a solution and to use the solution over a period of 2-24 hours or greater for the two vial, wet/dry, product. For the single vial, solution product, the label indicates that such solution can be used over a period of 2-24 hours or greater. The presently claimed products are useful for human pharmaceutical product use.

The formulations of the present invention can be prepared by a process that comprises mixing at least one anti-IL-23p19 antibody and a selected buffer, preferably, a phosphate buffer containing saline or a chosen salt. Mixing the at least one anti-IL-23p19 antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one anti-IL-23p19 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

Other formulations or methods of stabilizing the anti-IL-23p19 antibody may result in other than a clear solution of lyophilized powder comprising the antibody. Among non-clear solutions are formulations comprising particulate suspensions, said particulates being a composition containing the anti-IL-23p19 antibody in a structure of variable dimension and known variously as a microsphere, microparticle, nanoparticle, nanosphere, or liposome. Such relatively homogenous, essentially spherical, particulate formulations containing an active agent can be formed by contacting an aqueous phase containing the active agent and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active agent and a polymer dispersed in a continuous solvent and removing said solvent from the suspension by freeze-drying or dilution-extraction-precipitation as taught in U.S. Pat. No. 4,818,542. Preferred polymers for such preparations are natural or synthetic copolymers or polymers selected from the group consisting of gleatin agar, starch, arabinogalactan, albumin, collagen, polyglycolic acid, polylactic aced, glycolide-L(-) lactide poly(episilon-caprolactone, poly(epsilon-caprolactone-CO-lactic acid), poly(epsilon-caprolactone-CO-glycolic acid), poly(B-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic aced, glycolide-L(-) lactide poly(episilon-caprolactone, poly(epsilon-caprolactone-CO-lactic acid), and poly(epsilon-caprolactone-CO-glycolic acid. Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase may include pressure forcing said first phase through an orifice in a nozzle to affect droplet formation.

Dry powder formulations may result from processes other than lyophilization, such as by spray drying or solvent extraction by evaporation or by precipitation of a crystalline composition followed by one or more steps to remove aqueous or nonaqueous solvent. Preparation of a spray-dried antibody preparation is taught in U.S. Pat. No. 6,019,968. The antibody-based dry powder compositions may be produced by spray drying solutions or slurries of the antibody and, optionally, excipients, in a solvent under conditions to provide a respirable dry powder. Solvents may include polar compounds, such as water and ethanol, which may be readily dried. Antibody stability may be enhanced by performing the spray drying procedures in the absence of oxygen, such as under a nitrogen blanket or by using nitrogen as the drying gas. Another relatively dry formulation is a dispersion of a plurality of perforated microstructures dispersed in a suspension medium that typically comprises a hydrofluoroalkane propellant as taught in WO 9916419. The stabilized dispersions may be administered to the lung of a patient using a metered dose inhaler. Equipment useful in the commercial manufacture of spray dried medicaments are manufactured by Buchi Ltd. or Niro Corp.

At least one anti-IL-23p19 antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

The present invention also provides a method for modulating or treating at least one IL-23 related disease, in a cell, tissue, organ, animal, or patient, as known in the art or as described herein, using at least one IL-23p19 antibody of the present invention, e.g., administering or contacting the cell, tissue, organ, animal, or patient with a therapeutic effective amount of IL-23p19 antibody. The present invention also provides a method for modulating or treating at least one IL-23 related disease, in a cell, tissue, organ, animal, or patient including, but not limited to, at least one of obesity, an immune related disease, a cardiovascular disease, an infectious disease, a malignant disease or a neurologic disease.

The present invention also provides a method for modulating or treating at least one IL-23 related immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, osteolysis, aseptic loosening of orthopedic implants, inflammatory bowel disease, ulcerative colitis, systemic lupus erythematosus, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitivity reactions, allergic rhinitis, hay fever, perennial rhinitis, conjunctivitis, endometriosis, asthma, urticaria, systemic anaphylaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynaud's disease, type B insulin-resistant diabetes, asthma, myasthenia gravis, antibody-meditated cytotoxicity, type III hypersensitivity reactions, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited to, asthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The present invention also provides a method for modulating or treating at least one cardiovascular disease in a cell, tissue, organ, animal, or patient, including, but not limited to, at least one of cardiac stun syndrome, myocardial infarction, congestive heart failure, stroke, ischemic stroke, hemorrhage, acute coronary syndrome, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occlusion of the abdominal aorta and its branches, peripheral vascular disorders, occlusive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like. Such a method can optionally comprise administering an effective amount of a composition or pharmaceutical composition comprising at least one anti-IL-23p19 antibody to a cell, tissue, organ, animal or patient in need of such modulation, treatment or therapy.

The present invention also provides a method for modulating or treating at least one IL-23 related infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (e.g., A, B or C, or the like), septic arthritis, peritonitis, pneumonia, epiglottitis, *E. coli* 0157:h7, hemolytic uremic syndrome/thrombolytic-thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium intracellulare, pneumocystis carinii* pneumonia, pelvic inflammatory disease, orchitis/epidydimitis, *legionella*, lyme disease, influenza a, epstein-barr virus, viral-associated hemaphagocytic syndrome, viral encephalitis/aseptic meningitis, and the like.

The present invention also provides a method for modulating or treating at least one IL-23 related malignant disease in a cell, tissue, organ, animal or patient, including, but not limited to, at least one of: leukemia, acute leukemia, acute lymphoblastic leukemia (ALL), acute lymphocytic leukemia, B-cell, T-cell or FAB ALL, acute myeloid leukemia (AML), acute myelogenous leukemia, chromic myelocytic leukemia (CML), chronic lymphocytic leukemia (CLL), hairy cell leukemia, myelodyplastic syndrome (MDS), a lymphoma, Hodgkin's disease, a malignamt lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, bladder cancer, breast cancer, colorectal cancer, endometiral cancer, head cancer, neck cancer, hereditary non-polyposis cancer, Hodgkin's lymphoma, liver cancer, lung cancer, non-small cell lung cancer, ovarian cancer, pancreatic cancer, prostate cancer, renal cell carcinoma, testicular cancer, adenocarcinomas, sarcomas, malignant melanoma, hemangioma, metastatic disease, cancer related bone resorption, cancer related bone pain, and the like.

The present invention also provides a method for modulating or treating at least one IL-23 related neurologic disease in a cell, tissue, organ, animal or patient, including, but not limited to, at least one of: neurodegenerative diseases, multiple sclerosis, migraine headache, AIDS dementia complex, demyelinating diseases, such as multiple sclerosis and acute transverse myelitis; extrapyramidal and cerebellar disorders, such as lesions of the corticospinal system; disorders of the basal ganglia; hyperkinetic movement disorders, such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi-system disorder); demyelinating core disorders, such as multiple sclerosis, acute transverse myelitis; and disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; Dementia pugilistica; neurotraumatic injury (e.g., spinal cord injury, brain injury, concussion, repetitive concussion); pain; inflammatory pain; autism; depression; stroke; cognitive disorders; epilepsy; and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, 16$^{th}$ Edition, Merck & Company, Rahway, N.J. (1992).

The present invention also provides a method for modulating or treating at least one IL-23 related wound, trauma or tissue injury or related chronic condition, in a cell, tissue, organ, animal or patient, including, but not limited to, at least one of: bodily injury or a trauma associated with oral surgery including periodontal surgery, tooth extraction(s), endodontic treatment, insertion of tooth implants, application and use of tooth prosthesis; or wherein the wound is selected from the group consisting of aseptic wounds, contused wounds, incised wounds, lacerated wounds, non-penetrating wounds, open wounds, penetrating wounds, perforating wounds, puncture wounds, septic wounds, infarctions and subcutaneous wounds; or wherein the wound is selected from the group consisting of ischemic ulcers, pressure sores, fistulae, severe bites, thermal burns and donor site wounds; or wherein the wound is anaphthous wound, a traumatic wound or a herpes associated wound.

Wounds and/or ulcers are normally found protruding from the skin or on a mucosal surface or as a result of an infarction in an organ ("stroke"). A wound may be a result of a soft tissue defect or a lesion or of an underlying condition. In the present context, the term "skin" relates to the outermost surface of the body of an animal, including a human, and embraces intact or almost intact skin as well as an injured skin surface. The term "mucosa" relates to undamaged or damaged mucosa of an animal, such as a human, and may be the oral, buccal, aural, nasal, lung, eye, gastrointestinal, vaginal, or rectal mucosa.

In the present context the term "wound" denotes a bodily injury with disruption of the normal integrity of tissue structures. The term is also intended to encompass the terms "sore," "lesion," "necrosis," and "ulcer." Normally, the term "sore" is a popular term for almost any lesion of the skin or mucous membranes and the term "ulcer" is a local defect, or excavation, of the surface of an organ or tissue, which is produced by the sloughing of necrotic tissue. Lesion generally relates to any tissue defect. Necrosis is related to dead tissue resulting from infection, injury, inflammation or infarctions.

The term "wound" used in the present context denotes any wound (see below for a classification of wounds) and at any particular stage in the healing process, including the stage before any healing has initiated or even before a specific wound like a surgical incision is made (prophylactic treatment). Examples of wounds which can be prevented and/or treated in accordance with the present invention are, e.g., aseptic wounds, contused wounds, incised wounds, lacerated wounds, non-penetrating wounds (i.e., wounds in which there is no disruption of the skin but there is injury to underlying structures), open wounds, penetrating wounds, perforating wounds, puncture wounds, septic wounds, subcutaneous wounds, etc. Examples of sores are bed sores, canker sores, chrome sores, cold sores, pressure sores, etc. Examples of ulcers are, e.g., a peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous ulcer, symptomatic ulcer, trophic ulcer, tropical ulcer, and veneral ulcer, e.g., caused by gonorrhoea (including urethritis, endocervicitis and proctitis). Conditions related to wounds or sores which may be successfully treated according to the invention are burns, anthrax, tetanus, gas gangrene, scarlatina, erysipelas, sycosis barbae, folliculitis, impetigo contagiosa, or impetigo bullosa, etc. There is often a certain overlap between the use of the terms "wound" and "ulcer" and "wound" and "sore" and, furthermore, the terms are often used at random. Therefore, as mentioned above, in the present context the term "wound" encompasses the terms "ulcer," "lesion," "sore" and "infarction," and the terms are indiscriminately used unless otherwise indicated.

The kinds of wounds to be treated according to the invention include also (i) general wounds, such as, e.g., surgical, traumatic, infectious, ischemic, thermal, chemical and bullous wounds; (ii) wounds specific for the oral cavity, such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and (iii) wounds on the skin, such as, e.g., neoplasm, burns (e.g. chemical, thermal), lesions (bacterial, viral, autoimmunological), bites and surgical incisions. Another way of classifying wounds is as (i) small tissue loss due to surgical incisions, minor abrasions and minor bites, or as (ii) significant tissue loss. The latter group includes ischemic ulcers, pressure sores, fistulae, lacerations, severe bites, thermal burns and donor site wounds (in soft and hard tissues) and infarctions.

Other wounds that are of importance in connection with the present invention are wounds like ischemic ulcers, pressure sores, fistulae, severe bites, thermal burns and donor site wounds. Ischemic ulcers and pressure sores are wounds which normally only heal very slowly and especially in such cases, an improved and more rapid healing process is of course of great importance for the patient. Furthermore, the costs involved in the treatment of patients suffering from such wounds are markedly reduced when the healing is improved and takes place more rapidly.

Donor site wounds are wounds which, e.g., occur in connection with removal of hard tissue from one part of the body to another part of the body, e.g., in connection with transplantation. The wounds resulting from such operations are very painful and an improved healing is therefore most valuable. The term "skin" is used in a very broad sense embracing the epidermal layer of the skin and—in those cases where the skin surface is more or less injured—also the dermal layer of the skin. Apart from the stratum corneum, the epidermal layer of the skin is the outer (epithelial) layer and the deeper connective tissue layer of the skin is called the dermis.

The present invention also provides a method for modulating or treating psoriasis, psoriatic arthritis, Crohn's disease, multiple sclerosis, and optic neuritis, among the other diseases listed above as IL-23 related, in a cell, tissue, organ, animal, or patient including, but not limited to, at least one of immune related disease, cardiovascular disease, infectious, malignant and/or neurologic disease. Such a method can optionally comprise administering an effective amount of at least one composition or pharmaceutical composition comprising at least one anti-IL-23p19 antibody to a cell, tissue, organ, animal or patient in need of such modulation, treatment or therapy.

Any method of the present invention can comprise administering an effective amount of a composition or pharmaceutical composition comprising at least one anti-IL-23p19 antibody to a cell, tissue, organ, animal or patient in need of such modulation, treatment or therapy. Such a method can optionally further comprise co-administration or combination therapy for treating such diseases or disorders, wherein the administering of said at least one anti-IL-23p19 antibody, specified portion or variant thereof, further comprises administering, before concurrently, and/or after, at least one selected from at least one TNF antagonist (e.g., but not limited to, a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-I or TBP-II), nerelimonmab, infliximab, etanercept (Enbrel™), adalimulab (Humira™), CDP-571, CDP-870, afelimomab, lenercept, and the like), an antirheumatic (e.g., methotrexate, auranofin, aurothioglucose, azathioprine, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000); Nursing 2001 Handbook of Drugs, $21^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J. each of which references are entirely incorporated herein by reference.

TNF antagonists suitable for compositions, combination therapy, co-administration, devices and/or methods of the present invention (further comprising at least one antibody, specified portion and variant thereof, of the present invention), include, but are not limited to, anti-TNF antibodies (e.g., at least one TNF antagonist as defined above), antigen-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g, pentoxifylline and rolipram), A2b adenosine receptor agonists and A2b. adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

As used herein, a "tumor necrosis factor antibody," "TNF antibody," "TNFα antibody," or fragment and the like decreases, blocks, inhibits, abrogates or interferes with TNFα activity in vitro, in situ and/or, preferably, in vivo. For example, a suitable TNF human antibody of the present invention can bind TNFα and includes anti-TNF antibodies, antigen-binding fragments thereof, and specified mutants or domains thereof that bind specifically to TNFα. A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

An example of a TNF antibody or antagonist is the chimeric antibody cA2. Additional examples of monoclonal anti-TNF antibodies that can be used in the present invention are described in the art (see, e.g., U.S. Pat. No. 5,231,024; Möller, A. et al., *Cytokine* 2(3):162-169 (1990); U.S. application Ser. No. 07/943,852 (filed Sep. 11, 1992); Rathjen et al., International Publication No. WO 91/02078 (published Feb. 21, 1991); Rubin et al., EPO Patent Publication No. 0 218 868 (published Apr. 22, 1987); Yone et al., EPO Patent Publication No. 0 288 088 (Oct. 26, 1988); Liang, et al., *Biochem. Biophys. Res. Comm.* 137:847-854 (1986); Meager, et al., *Hybridoma* 6:305-311 (1987); Fendly et al., *Hybridoma* 6:359-369 (1987); Bringman, et al., *Hybridoma* 6:489-507 (1987); and Hirai, et al., *J. Immunol. Meth.* 96:57-62 (1987).

TNF Receptor Molecules

Preferred TNF receptor molecules useful in the present invention are those that bind TNFα with high affinity (see, e.g., Feldmann et al., International Publication No. WO 92/07076 (published Apr. 30, 1992); Schall et al., *Cell* 61:361-370 (1990); and Loetscher et al., *Cell* 61:351-359 (1990), which references are entirely incorporated herein by reference) and optionally possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof (see, e.g., Corcoran et al., *Eur. J. Biochem.* 223:831-840 (1994)), are also useful in the present invention. Truncated forms of the TNF receptors, comprising the ECD, have been detected in urine and serum as 30 kDa and 40 kDa TNFα inhibitory binding proteins (Engelmann, H. et al., *J. Biol. Chem.* 265:1531-1536 (1990)). TNF receptor multimeric molecules and TNF immunoreceptor fusion molecules, and derivatives and fragments or portions thereof, are additional examples of TNF receptor molecules which are useful in the methods and compositions of the present invention.

TNF receptor multimeric molecules useful in the present invention comprise all or a functional portion of the ECD of two or more TNF receptors linked via one or more polypeptide linkers or other nonpeptide linkers, such as polyethylene glycol (PEG). An example of such a TNF immunoreceptor fusion molecule is TNF receptor/IgG fusion protein. TNF immunoreceptor fusion molecules and methods for their production have been described in the art (Lesslauer et al., *Eur. J. Immunol.* 21:2883-2886 (1991); Ashkenazi et al., *Proc. Natl. Acad. Sci. USA* 88:10535-10539 (1991); Peppel et al., *J. Exp. Med.* 174:1483-1489 (1991); Kolls et al., *Proc. Natl. Acad. Sci. USA* 91:215-219 (1994); Butler et al., *Cytokine* 6(6):616-623 (1994); Baker et al., *Eur. J. Immunol.* 24:2040-2048 (1994); Beutler et al., U.S. Pat. No. 5,447,851; and U.S. application Ser. No. 08/442,133 (filed May 16, 1995), each of which references are entirely incorporated herein by reference). Methods for producing immunoreceptor fusion molecules can also be found in Capon et al., U.S. Pat. No. 5,116, 964; Capon et al., U.S. Pat. No. 5,225,538; and Capon et al., *Nature* 337:525-531 (1989), which references are entirely incorporated herein by reference.

Cytokines include any known cytokine. See, e.g., CopewithCytokines.com. Cytokine antagonists include, but are not limited to, any antibody, fragment or mimetic, any soluble receptor, fragment or mimetic, any small molecule antagonist, or any combination thereof.

Therapeutic Treatments

Any method of the present invention can comprise a method for treating an IL-23 mediated disorder, comprising administering an effective amount of a composition or pharmaceutical composition comprising at least one anti-IL-23p19 antibody to a cell, tissue, organ, animal or patient in need of such modulation, treatment or therapy. Such a method can optionally further comprise co-administration or combination therapy for treating such diseases or disorders, wherein the administering of said at least one anti-IL-23p19 antibody, specified portion or variant thereof, further comprises administering before, concurrently, and/or after, at least one selected from an anti-infective drug, a cardiovascular (CV) system drug, a central nervous system (CNS) drug, an autonomic nervous system (ANS) drug, a respiratory tract drug, a gastrointestinal (G1) tract drug, a hormonal drug, a drug for fluid or electrolyte balance, a hematologic drug, an antineoplastic, an immunomodulation drug, an ophthalmic, otic or nasal drug, a topical drug, a nutritional drug or the like, at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Such drugs are well known in the art, including formulations, indications, dosing and administration for each presented herein (see., e.g., Nursing 2001 Handbook of Drugs, 21$^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

Typically, treatment of pathologic conditions is effected by administering an effective amount or dosage of at least one anti-IL-23p19 antibody composition that total, on average, a range from at least about 0.01 to 500 milligrams of at least one anti-IL-23p19 antibody per kilogram of patient per dose, and, preferably, from at least about 0.1 to 100 milligrams antibody/kilogram of patient per single or multiple administration, depending upon the specific activity of the active agent contained in the composition. Alternatively, the effective serum concentration can comprise 0.1-5000 µg/ml serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include about 0.1-99 and/or 100-500 mg/kg/administration, or any range, value or fraction thereof, or to achieve a serum concentration of about 0.1-5000 µg/ml serum concentration per single or multiple administration, or any range, value or fraction thereof. A preferred dosage range for the anti-IL-23p19 antibody of the present invention is from about 1 mg/kg, up to about 3, about 6 or about 12 mg/kg of body weight of the patient.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and, preferably, 0.1 to 10 milligrams per kilogram per administration or in sustained release form is effective to obtain desired results.

As a non-limiting example, treatment of humans or animals can be provided as a one-time or periodic dosage of at least one antibody of the present invention about 0.1 to 100 mg/kg or any range, value or fraction thereof per day, on at least one of day 1-40, or, alternatively or additionally, at least one of week 1-52, or, alternatively or additionally, at least one of 1-20 years, or any combination thereof, using single, infusion or repeated doses.

Dosage forms (composition) suitable for internal administration generally contain from about 0.001 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and about 1-10% human serum albumin. Liposomes and nonaqueous vehicles, such as fixed oils, can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration

Many known and developed modes can be used according to the present invention for administering pharmaceutically effective amounts of at least one anti-IL-23p19 antibody according to the present invention. While pulmonary administration is used in the following description, other modes of administration can be used according to the present invention with suitable results. IL-23p19 antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration

Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semisynthtetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

Alternative Delivery

The invention further relates to the administration of at least one anti-IL-23p19 antibody by parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal means. At least one anti-IL-23p19 antibody composition can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways, such as electroporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

Pulmonary/Nasal Administration

For pulmonary administration, preferably, at least one anti-IL-23p19 antibody composition is delivered in a particle size effective for reaching the lower airways of the lung or sinuses. According to the invention, at least one anti-IL-23p19 antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use formulations suitable for the administration for the dispensing of antibody in an aerosol. Such aerosols can be comprised of either solutions (both aqueous and non aqueous) or solid particles.

Metered dose inhalers like the Ventolin® metered dose inhaler, typically use a propellent gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention.

Preferably, a composition comprising at least one anti-IL-23p19 antibody is delivered by a dry powder inhaler or a sprayer. There are several desirable features of an inhalation device for administering at least one antibody of the present invention. For example, delivery by the inhalation device is advantageously reliable, reproducible, and accurate. The inhalation device can optionally deliver small dry particles, e.g., less than about 10 µm, preferably about 1-5 µm, for good respirability.

Administration of IL-23p19 Antibody Compositions as a Spray

A spray including IL-23p19 antibody composition can be produced by forcing a suspension or solution of at least one anti-IL-23p19 antibody through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one anti-IL-23p19 antibody composition delivered by a sprayer have a particle size less than about 10 μm, preferably, in the range of about 1 μm to about 5 μm, and, most preferably, about 2 μm to about 3 μm.

Formulations of at least one anti-IL-23p19 antibody composition suitable for use with a sprayer typically include antibody composition in an aqueous solution at a concentration of about 0.1 mg to about 100 mg of at least one anti-IL-23p19 antibody composition per ml of solution or mg/gm, or any range, value, or fraction therein. The formulation can include agents, such as an excipient, a buffer, an isotonicity agent, a preservative, a surfactant, and, preferably, zinc. The formulation can also include an excipient or agent for stabilization of the antibody composition, such as a buffer, a reducing agent, a bulk protein, or a carbohydrate. Bulk proteins useful in formulating antibody compositions include albumin, protamine, or the like. Typical carbohydrates useful in formulating antibody compositions include sucrose, mannitol, lactose, trehalose, glucose, or the like. The antibody composition formulation can also include a surfactant, which can reduce or prevent surface-induced aggregation of the antibody composition caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein, such as IL-23p19 antibodies, or specified portions or variants, can also be included in the formulation.

Administration of IL-23p19 Antibody Compositions by a Nebulizer

Antibody compositions of the invention can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition either directly or through a coupling fluid, creating an aerosol including the antibody composition. Advantageously, particles of antibody composition delivered by a nebulizer have a particle size less than about 10 µm, preferably, in the range of about 1 µm to about 5 µm, and, most preferably, about 2 µm to about 3 µm.

Formulations of at least one anti-IL-23p19 antibody suitable for use with a nebulizer, either jet or ultrasonic, typically include a concentration of about 0.1 mg to about 100 mg of at least one anti-IL-23p19 antibody protein per ml of solution. The formulation can include agents, such as an excipient, a buffer, an isotonicity agent, a preservative, a surfactant, and, preferably, zinc. The formulation can also include an excipient or agent for stabilization of the at least one anti-IL-23p19 antibody composition, such as a buffer, a reducing agent, a bulk protein, or a carbohydrate. Bulk proteins useful in formulating at least one anti-IL-23p19 antibody compositions include albumin, protamine, or the like. Typical carbohydrates useful in formulating at least one anti-IL-23p19 antibody include sucrose, mannitol, lactose, trehalose, glucose, or the like. The at least one anti-IL-23p19 antibody formulation can also include a surfactant, which can reduce or prevent surface-induced aggregation of the at least one anti-IL-23p19 antibody caused by atomization of the solution in forming an aerosol. Various conventional surfactants can be employed, such as polyoxyethylene fatty acid esters and alcohols, and polyoxyethylene sorbital fatty acid esters. Amounts will generally range between about 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein, such as antibody protein, can also be included in the formulation.

Administration of IL-23p19 Antibody Compositions by a Metered Dose Inhaler

In a metered dose inhaler (MDI), a propellant, at least one anti-IL-23p19 antibody, and any excipients or other additives are contained in a canister as a mixture including a liquefied compressed gas. Actuation of the metering valve releases the mixture as an aerosol, preferably containing particles in the size range of less than about 10 µm, preferably, about 1 µm to about 5 µm, and, most preferably, about 2 µm to about 3 µM. The desired aerosol particle size can be obtained by employing a formulation of antibody composition produced by various methods known to those of skill in the art, including jet-milling, spray drying, critical point condensation, or the like. Preferred metered dose inhalers include those manufactured by 3M or Glaxo and employing a hydrofluorocarbon propellant. Formulations of at least one anti-IL-23p19 antibody for use with a metered-dose inhaler device will generally include a finely divided powder containing at least one anti-IL-23p19 antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluoroalkane-134a), HFA-227 (hydrofluoroalkane-227), or the like. Preferably, the propellant is a hydrofluorocarbon. The surfactant can be chosen to stabilize the at least one anti-IL-23p19 antibody as a suspension in the propellant, to protect the active agent against chemical degradation, and the like. Suitable surfactants include sorbitan trioleate, soya lecithin, oleic acid, or the like. In some cases, solution aerosols are preferred using solvents, such as ethanol. Additional agents known in the art for formulation of a protein can also be included in the formulation. One of ordinary skill in the art will recognize that the methods of the current invention can be achieved by pulmonary administration of at least one anti-IL-23p19 antibody composition via devices not described herein.

Oral Formulations and Administration

Formulations for oral administration rely on the co-administration of adjuvants (e.g., resorcinols and nonionic surfactants, such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Formulations for delivery of hydrophilic agents including proteins and antibodies and a combination of at least two surfactants intended for oral, buccal, mucosal, nasal, pulmonary, vaginal transmembrane, or rectal administration are taught in U.S. Pat. No. 6,309,663. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant, such as magnesium stearate; paraben, preserving agent, such as sorbic acid, ascorbic acid, .alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925, 673). Furthermore, carrier compounds described in U.S. Pat. No. 5,879,681 and U.S. Pat. No. 5,871,753 and used to deliver biologically active agents orally are known in the art.

Mucosal Formulations and Administration

A formulation for orally administering a bioactive agent encapsulated in one or more biocompatible polymer or copolymer excipients, preferably, a biodegradable polymer or copolymer, affording microcapsules which due to the proper size of the resultant microcapsules results in the agent reaching and being taken up by the folliculi lymphatic aggregati, otherwise known as the "Peyer's patch," or "GALT" of the animal without loss of effectiveness due to the agent having passed through the gastrointestinal tract. Similar folliculi lymphatic aggregati can be found in the bronchei tubes (BALT) and the large intestine. The above-described tissues are referred to in general as mucosally associated lymphoreticular tissues (MALT). For absorption through mucosal surfaces, compositions and methods of administering at least one anti-IL-23p19 antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g., suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration, excipients include sugars, calcium stearate, magnesium stearate, pregelinatined starch, and the like (U.S. Pat. No. 5,849,695).

Transdermal Formulations and Administration

For transdermal administration, the at least one anti-IL-23p19 antibody is encapsulated in a delivery device, such as a liposome or polymeric nanoparticles, microparticle, microcapsule, or microspheres (referred to collectively as microparticles unless otherwise stated). A number of suitable devices are known, including microparticles made of synthetic polymers, such as polyhydroxy acids, such as polylactic acid, polyglycolic acid and copolymers thereof, polyorthoesters, polyanhydrides, and polyphosphazenes, and natural polymers, such as collagen, polyamino acids, albumin and other proteins, alginate and other polysaccharides, and combinations thereof (U.S. Pat. No. 5,814,599).

Prolonged Administration and Formulations

It can be desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid, such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation, such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b), e.g., a zinc tannate salt. Additionally, the compounds of the present invention or, preferably, a relatively insoluble salt, such as those just described, can be formulated in a gel, for example, an aluminum monostearate gel with, e.g., sesame oil, suitable for injection. Particularly preferred salts are zinc salts, zinc tannate salts, pamoate salts, and the like. Another type of slow release depot formulation for injection would contain the compound or salt dispersed for encapsulation in a slow degrading, non-toxic, non-antigenic polymer, such as a polylactic acid/polyglycolic acid polymer for example as described in U.S. Pat. No. 3,773,919. The compounds or, preferably, relatively insoluble salts, such as those described above, can also be formulated in cholesterol matrix silastic pellets, particularly for use in animals. Additional slow release, depot or implant formulations, e.g., gas or liquid liposomes, are known in the literature (U.S. Pat. No. 5,770, 222 and "Sustained and Controlled Release Drug Delivery Systems", J. R. Robinson ed., Marcel Dekker, Inc., N.Y., 1978).

Having generally described the invention, the same will be more readily understood by reference to the following examples, which are provided by way of illustration and are not intended as limiting.

EXAMPLES

Example 1

Isolation of Human Anti-Human IL-23 Specific Antibodies by Phage Display

General methods have been described for selection of antigen-specific antibodies from the HuCAL™ libraries prepared at MorphoSys (Knappik et al., 2000; Krebs et al., 2001; Rauchenberger et al, 2003). Vh region specific sub-pools of the HuCAL Gold™ Fab library (Kretzschmar & von Ruden, 2002) was used for the selection of antibodies against recombinant human IL-23 (hrIL-23). Several different selection strategies were used and include:

1. Selection against recombinant hIL-23 protein that was immobilized directly on plastic, with or without preadsorption of the library on recombinant human IL-12 protein (hrIL-12) also adsorbed directly on plastic. The recombinant hIL-23 and hIL-12 proteins were produced at Centocor.

2. Selection with recombinant human IL-23 protein in solution, followed by recovery of the bound phage by capture of the hIL-23 protein on an immobilized hrIL-12p40 mAb. Selections were carried with or without preadsorption of the library on recombinant hrIL-12 protein captured with the same mAb.

3. Selection with chemically biotinylated hrIL-23 protein in solution, followed by capture of the bound phage with SA-coated magnetic beads. Selections were carried out with or without hrIL-12 protein in molar excess as a competitor.

Recovered phagemid DNA was converted en masse into a Fab expression vector and individual clones following transformation were screened for binding to hrIL-23 and not to hrIL-12. Sequencing of the positive clones identified 76 unique Fabs.

Example 2

Characterization of Fabs

Positive Fabs were produced and purified as previously described (Knappik et al., 2000; Krebs et al., 2001; Rauchenberger et al, 2003) and confirmed for binding specificity to hrIL-23 but not to hrIL-12 or to the p40 subunit of hrIL-12 (hrp40) in assays similar to those described in Example 3 below. Confirmed Fabs were tested for (1) inhibition of hrIL-23 binding to human IL-23 receptor (hIL-23R) or to human IL-12 receptor β1 (hIL-12Rβ1), (2) lack of inhibition of hrIL-12 binding to IL-12RILβ1, (3) inhibition of hrIL-23 binding to TALL-104 cells naturally expressing IL-23R and IL-12Rβ1, and (4) binding affinity to hrIL-23, hrIL-12 and hrp40 subunit. The binding specificity and affinity are summarized in Table 1 and the inhibition of hrIL-23 binding to hIL-23R is listed in Table 2. Fab12A in Table 1 is a reference standard that is derived from an IL-12p40 specific mAb. IL-23R-Fc in Table 2 is a reference standard corresponding to the extracellular domain of human IL-23R fused to a human Fc.

In general, the receptor inhibition assays were similar to those described below in Example 4 for the mAb derivatives of these Fabs. One additional assay was to measure the inhibition of rhIL-23 binding to TALL 104 cells. These cells express both the human IL-23 and IL-12 R beta 1 receptors. 10 of the 13 candidate Fabs had the desired activity profile of no reactivity with human IL-12 or p40 proteins in any assay and at least partial inhibition of hrIL-23 binding to the IL-23 receptor. The CDR sequences of six of the Fabs (4083, 4190, 4205, 4217, 4649, and 4658) are shown in Table 4 (bold font). The full V-region sequences for these Fabs are shown in Table 8.

Production of Fabs in a Human IgG1 Format

Candidate Fabs were cloned into human IgG1/kappa or lambda mAb format vectors and produced by transient transfection in HEK293 cells for further analysis as mAbs. Overall, eleven of the 13 active Fabs show a desired profile as mAbs. They are specific for IL-23 and at least partially inhibited human IL-23 binding to the human IL-23R-Fc fusion protein (Table 3). The assays and results are cited in the Examples that follow.

Example 3

Subunit Specificity of hIL-23p19 mAbs Derived from Antibody Phage Display

Purified mouse anti-hIL-23 mAbs were evaluated in cytokine capture ELISA to determine their antigen subunit specificity. Briefly, IL-23 mAbs were coated onto plates and incubated with 100 ng/ml) hrIL-23, hrIL-12, and hrp40, respectively. Following incubation with biotinylated anti-p40 mAb, the binding was detected using HRP-conjugated streptavidin. An anti-p40 mAb and an anti-IL-12 mAb (20C2, Catalog No. 555065, BD Pharmingen, San Diego, Calif.) with known specificity were used as controls.

Figure 1B:
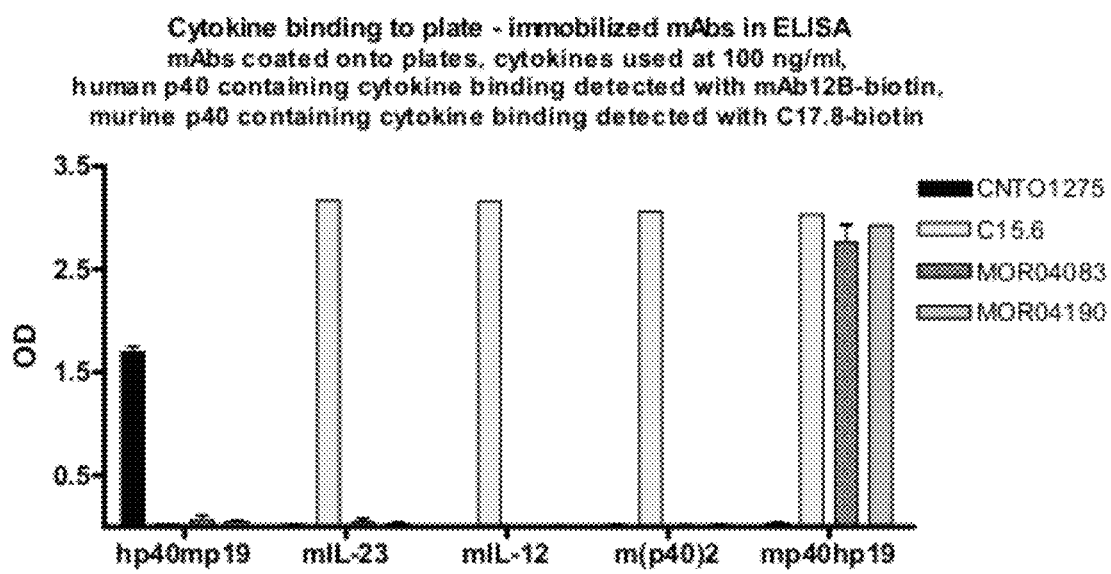
FIG. 1B shows that human IL-23p19 antibodies bind to human IL-23, but not to murine IL-23 or its subunits.
Figure 2:
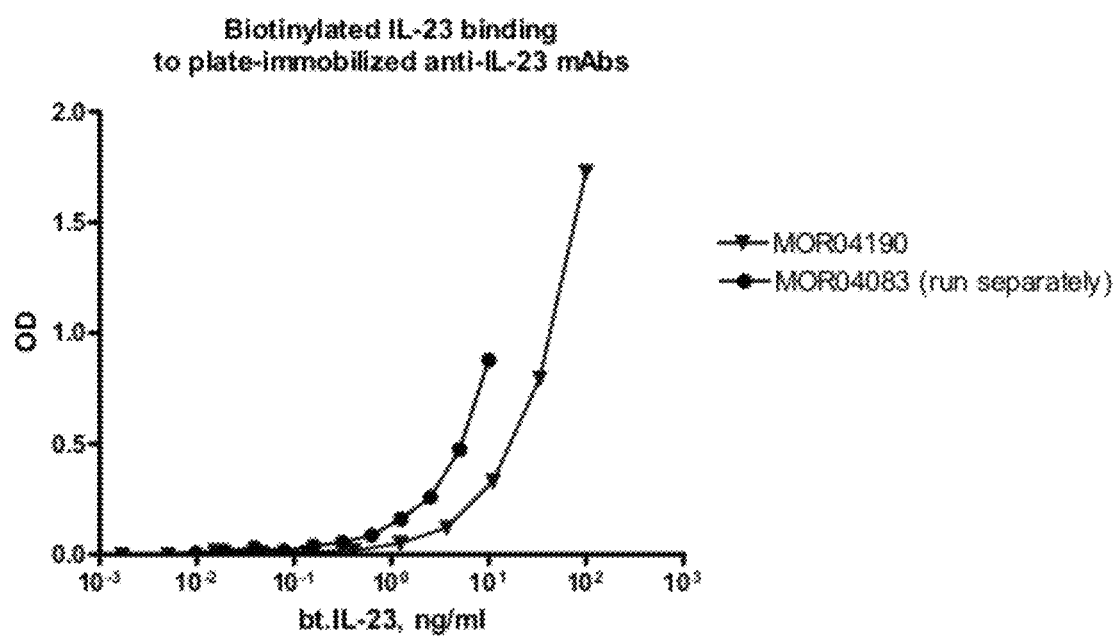
FIG. 2 shows the IL-23 binding to two of the plate-immobilized IL-23p19 antibodies of the invention.

FIGS. 1A and 1B demonstrate the binding specificity for two of these mAbs, MOR04083 (same as 4083) and MOR04190 (same as 4190). FIG. 1A shows that the mAbs bind specifically hrIL-23 and not hrIL-12 or hrp40 monomer. Because the IL-23p19 subunit must covalently associate with p40 to be secreted from mammalian cells, IL-23 mAbs that do not recognize p40 monomer must bind either the IL-23p19 subunit alone or a joint epitope of the p19-p40 heterodimer. Therefore, these IL-23 mAbs are referred to as IL-23p19 mAbs. In comparison, all 3 proteins (hrIL-23, hrIL-12 and hrp40) bind to mAb 12A, a neutralizing anti-human p40 specific antibody. FIG. 1B shows that the same mAbs do not bind to murine IL-23 or to murine p40. In a reverse format, the immobilized mAbs have similar binding curves to hrIL-23 in solution (FIG. 2), consistent with their comparable binding affinity as Fabs (Table 1). The binding specificity of these and the other candidate mAbs is summarized in Table 3.

Example 4

Inhibition of IL-23 Receptor Binding by IL-23p19 mAbs

Figure 3A:
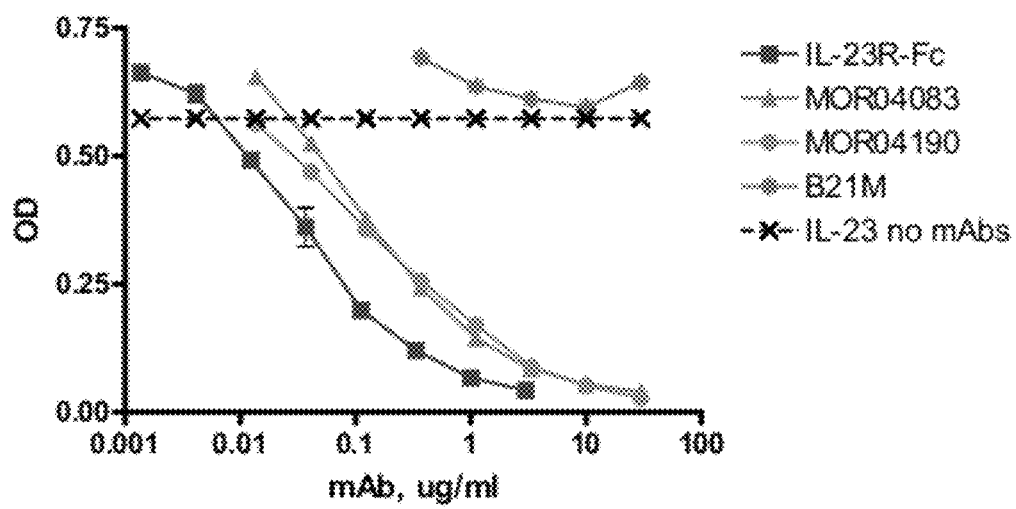
FIG. 3A shows that antibodies MOR04083 and MOR04190 block normal IL-23/IL-23R binding.
Figure 3B:
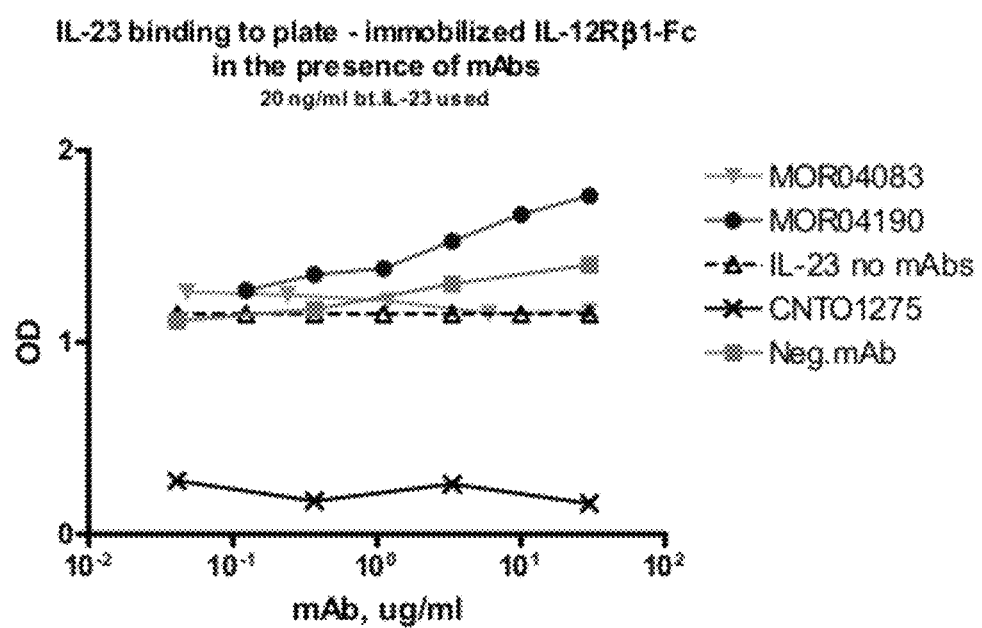
FIG. 3B shows that antibodies MOR04083 and MOR04190 do not block normal IL-23/IL-12Rβ1 binding.

To demonstrate that the IL-23p19 mAbs are neutralizing antibodies against the p19 subunit, the mAbs were tested for their inhibition of IL-23 and IL-23R binding. In this experiment, a human IL-23R-Fc fusion protein was immobilized on a plate. This fusion protein consists of the extracellular domain of human IL-23 receptor fused to a human Fc segment. Biotinylated hrIL-23 was added to the plate either alone or after preincubation with individual IL-23p19 mAbs. Soluble IL-23R (IL-23R-Fc) was used as a positive control. IL-23 binding was detected with HRP-conjugated streptavidin. As shown in FIG. 3A, the mAbs MOR04083 and MOR04190 prevent IL-23/IL-23R binding with a potency about 3-fold weaker than soluble IL-23R-Fc. There was no inhibition by B21M, a mAb with unrelated specificity. In contrast, when IL-12Rβ1 was immobilized on a plate, these mAbs did not inhibit IL-23/IL-12Rβ1 binding (FIG. 3B)). IL-23 binding was inhibited by the p40 neutralizing mAb CNTO 1275 (same as mAb 12A), as expected. Similarly, these mAbs do not block IL-12/IL-12Rβ1 binding (FIG. 3C). CNTO 1275 again served as a positive control. The selective inhibition of IL-23/IL-23R binding and the lack of interference with IL-12 or IL-23 binding to IL-12Rβ1 further demonstrates that these IL-23p19 mAbs do not bind the p40 subunit and thus are neutralizing anti-human IL-23p19 antibodies. The receptor inhibition studies with these mAbs are summarized in Table 3.

Example 5

Neutralization of IL-23 Biological Function by IL-23p19 mAbs

IL-23 is known to induce intracellular STAT3 phosphorylation and IL-17 production by T cells. Therefore, the IL-23p19 mAbs were tested for their ability to inhibit these biological functions of human IL-23.

Figure 4:
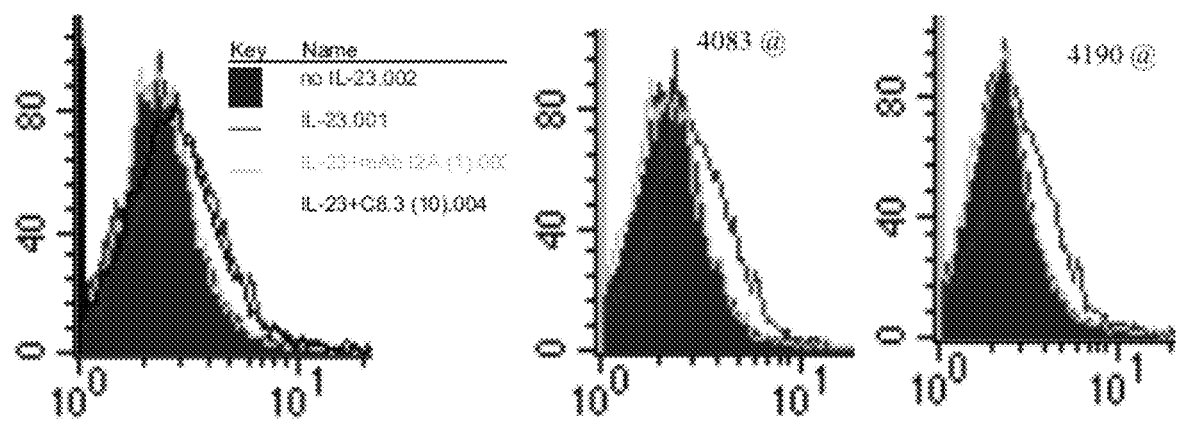
FIG. 4 shows that the IL-23p19 antibodies MOR04083 and MOR04190 of the invention inhibit hrIL-23 mediated STAT3 phosphorylation.

In one experiment, natural killer (NKL) cells were stimulated with hrIL-23 either alone or after preincubation with the MOR04083 and MOR0190 mAbs at 20 ug/ml and 10 ug/ml, respectively. MAb 12A (1 ug/ml) was the positive control and C8.3 (10 ug/ml), a non-neutralizing anti-human p40 mAb, was the negative control. Treated cells were stained with fluorochrome-conjugated anti-phospho-STAT3 antibodies and analyzed by intracellular flow cytometry (FIG. 4). These mAbs completely inhibit STAT3 phosphorylation, albeit with lower potency than the neutralizing anti-p40 mAb 12A. The lower potency of the IL-23p19 mAbs likely reflects their relatively weak affinity.

Figure 5A:
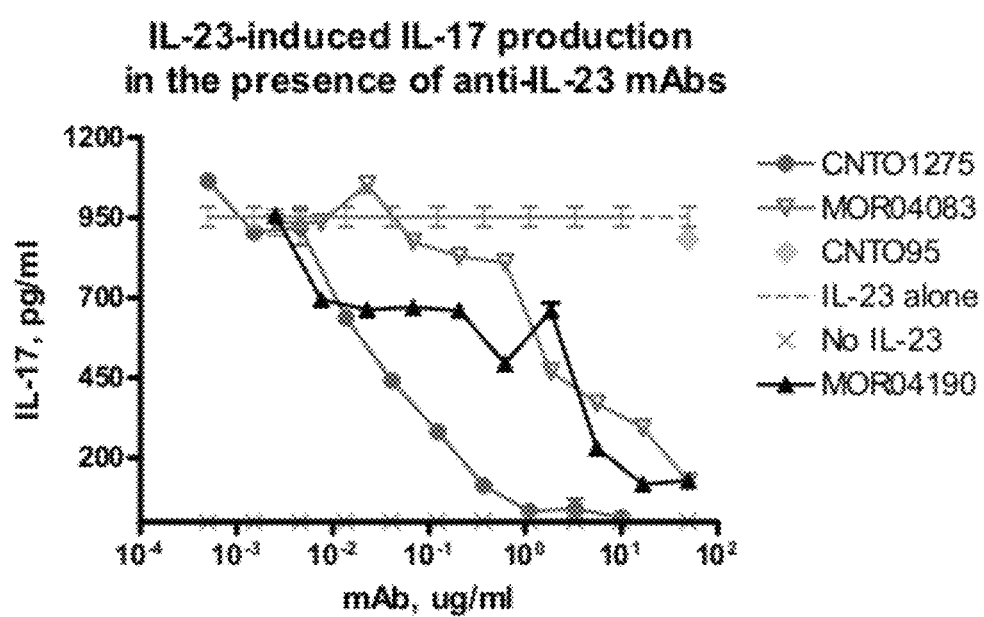
FIG. 5A shows that the IL-23p19 antibodies MOR04083 and MOR04190 of the invention inhibit recombinant hrIL-23 mediated IL-17 production.
Figure 5B:
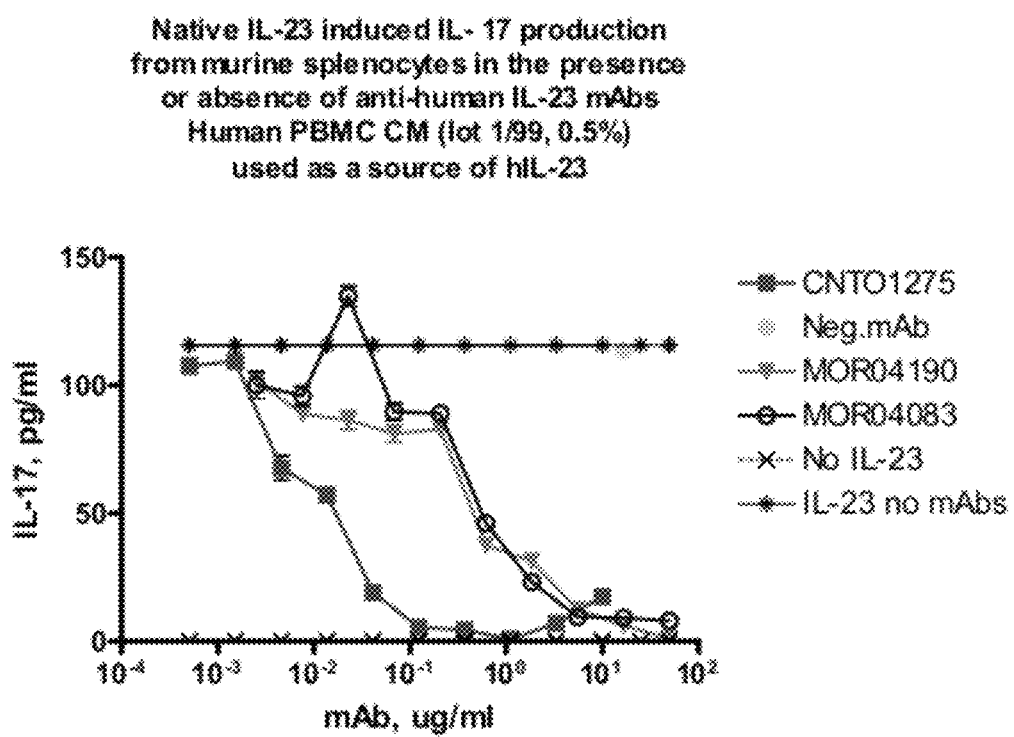
FIG. 5B shows that the IL-23p19 antibodies MOR04083 and MOR04190 of the invention inhibit native hrIL-23 mediated IL-17 production.
Figure 5C:
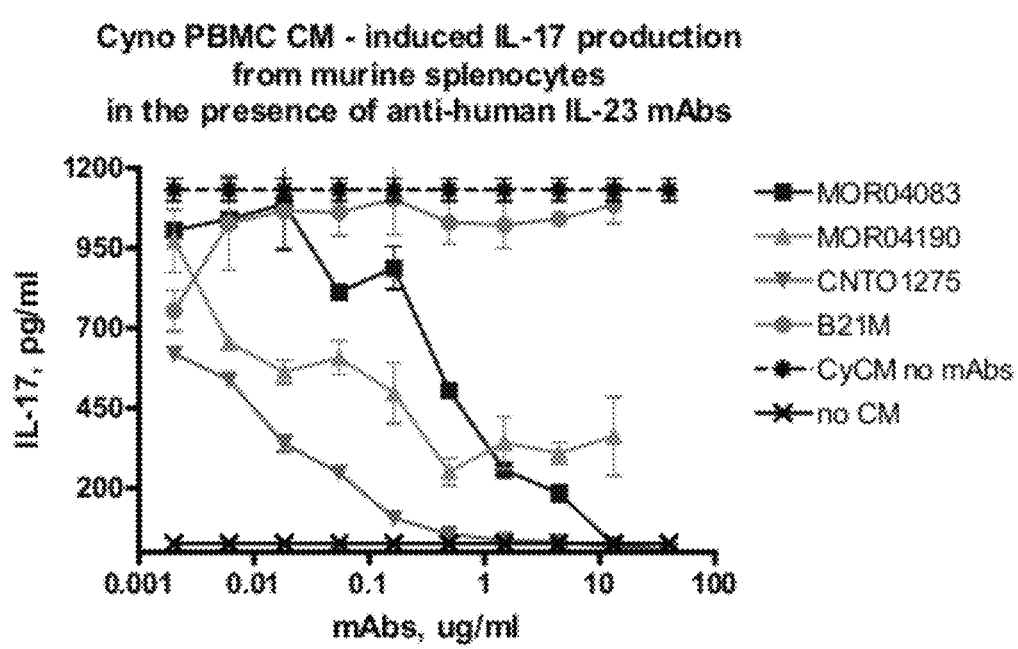
FIG. 5C shows that the IL-23p19 antibodies MOR04083 and MOR04190 of the invention inhibit native cynomologous monkey IL-23 mediated IL-17 production.

In another experiment, freshly isolated murine splenocytes were treated with hrIL-23 preincubated with titrated IL-23p19 mAbs or control mAbs. hrIL-23 with no antibody preincubation was used as the positive control. After 3 days in culture, cell supernatants were collected and assayed by ELISA using an IL-17 ELISA duo set (R&D Systems). As shown in FIG. 5A, IL-23p19 mAbs MOR04083 and MOR04190 inhibited hrIL-23 mediated IL-17 production. These mAbs also inhibited IL-17 production induced by native IL-23 produced by human (FIG. 5B) and cynomologous monkey (FIG. 5C) PBMCs.

Figure 6:
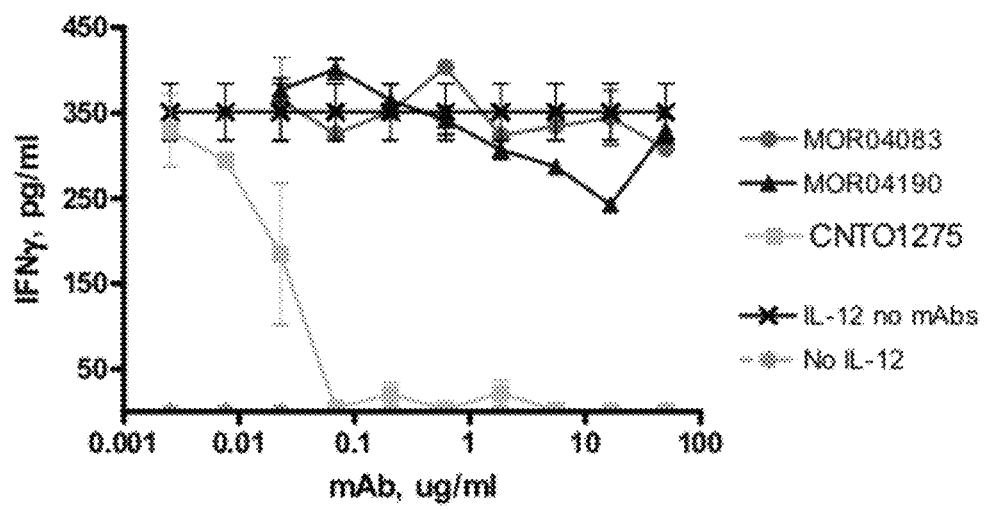
FIG. 6 shows that the IL-23p19 antibodies MOR04083 and MOR04190 of the invention do not inhibit hrIL-12 mediated IFNγ production.

In comparison, IL-23p19 mAbs were tested for their ability to inhibit hrIL-12 induced IFNγ production. Briefly, NK92MI cells were treated with IL-12 preincubated with titrated IL-23p19 mAbs or control mAbs (FIG. 6). IL-12 with no antibody preincubation was used as the negative control and CNTO 1275 as the positive control. ELISA analysis performed 24 hours post-stimulation showed no effect of IL-23p19 mAbs MOR04083 and 4190 on IL-12 induced IFNγ production demonstrating that the antibodies do not bind and neutralize the p40 subunit shared by IL-12 and IL-23. The results of these assays are summarized in Table 3.

Example 6

Epitope Identification of IL-23p19 mAbs

Figure 7A:
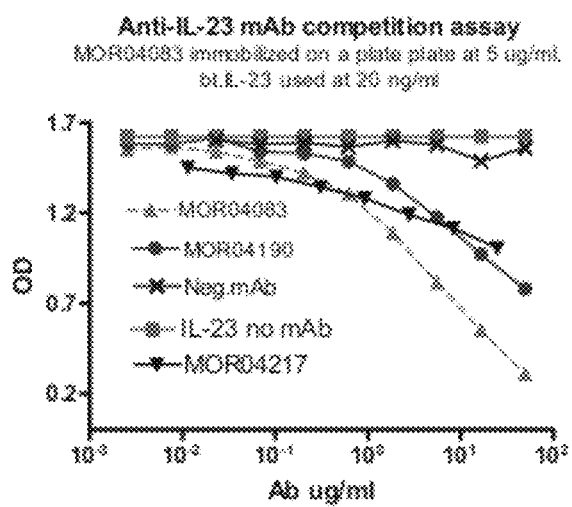
FIGS. 7A-C show that the IL-23p19 antibodies MOR04083, MOR04190, and MOR04217 of the invention cross-compete with each other for binding to huIL-23.
Figure 7B:
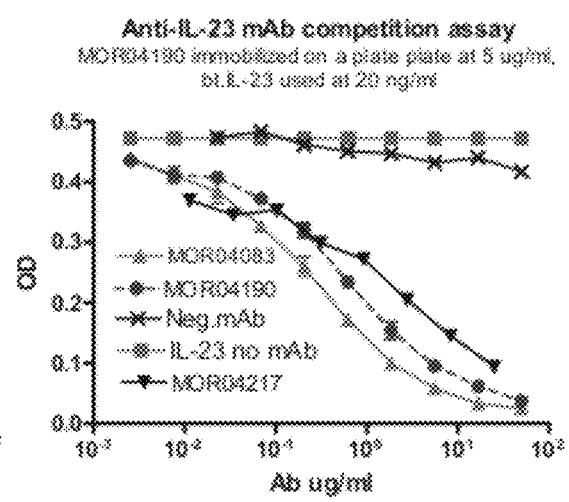
Figure 7C:
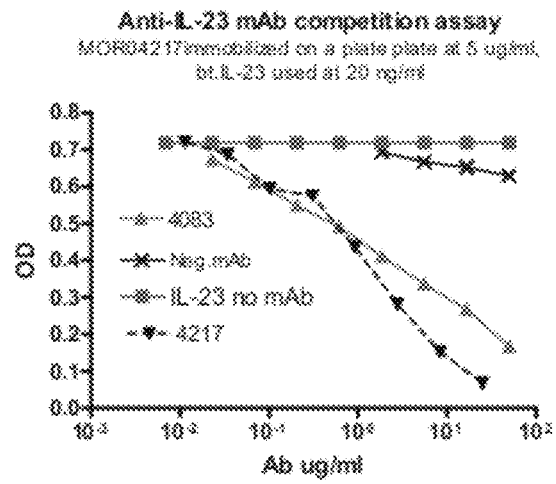

Competition binding analysis was performed to determine if the neutralizing IL-23p19 mAbs bind to similar or different IL-23p19 epitopes. The results for mAbs, MOR04083, MOR04190 and MOR04217, are shown in FIG. 7. IL-23 mAbs were individually coated on ELISA plates. Competing mAbs were added, followed by the addition of biotinylated hrIL-23. For positive control, the same mAb for coating was used as the competing mAb ("self-competition"). IL-23 binding was detected using streptavidin. All three mAbs show cross-competition to varying extents, indicating binding to spatially related sites.

Example 7

Affinity Maturation of Candidate Neutralizing Fabs

Fabs MOR04083, 04190, 04649 and 04658 were selected for independent affinity maturation based on the above characterization in both Fab and mAb formats. Utilizing the cassette feature of the HuCal™ system (Knappik et al., 2000), two variant phage libraries were constructed for each Fab, one for CDR3 of the light chain variable region (VL) and the other for CDR2 of the heavy chain variable region (VH). These libraries were selected against biotinylated hrIL-23 in solution under varying stringencies of wash and antigen concentration. 35 unique Fabs were recovered, each showing improved binding activity relative to the starting parental Fab. Subsequently, three additional Fabs (5267, 5268, and 5269; all VL-CDR3 variants of 4083) were selected in a second round of screening. The CDR sequences of the parental Fabs, the matured derivatives from the VL-CDR3 or VH-CDR2 libraries, and variants of those sequences are shown in Tables 4A and B. The complete V-region sequences are shown in Table 8.

Example 8

Production and Characterization of Affinity Matured Fabs

The 38 selected Fabs were produced, purified and characterized essentially as described in Examples 2-4 above. Ten of the Fabs gave poor yields and/or showed heterogeneous patterns in size exclusion chromatography and were excluded from further analysis. The remaining 28 Fabs were analyzed for specificity of binding, affinity, and inhibition of receptor binding. All of the Fabs were specific for IL-23p19 and had 10-500 fold higher affinities for hrIL-23 than the corresponding parental Fab (Tables 5 and 6). All showed improved IC50 values for inhibition of hrIL-23 binding to the IL-23R Fc fusion protein and, like the parental Fabs, did not inhibit either IL-23 or IL-12 binding to IL-12Rb1 receptor Fc fusion protein (Tables 5 and 6). As expected from these results, none of the Fabs inhibited hrIL-23 binding to TALL-104 cells as measured by flow cyotometry, consistent with the similar lack of inhibition by the parental Fabs.

Example 9

Production and Characterization of the Affinity Matured Abs in a mAb Format 34 of the 35 selected Fabs were cloned into human IgG1/kappa or lambda mAb format vectors and produced as mAbs by transient transfection in HEK293 cells for further analysis. All the antibodies were evaluated for inhibition of IL-17 production as described in Example 5, above (Table 7). In most cases, each of the matured derivatives was more potent than its corresponding parent, with improvements in IC50 up to 200 fold. The biochemical properties of the 34 mAbs were evaluated by SDS-PAGE and size exclusion chromatography for indications of aggregation, chain heterogeneity, and incomplete disulfide bond formation between the heavy and light chains and in the hinge region.

Figure 8:
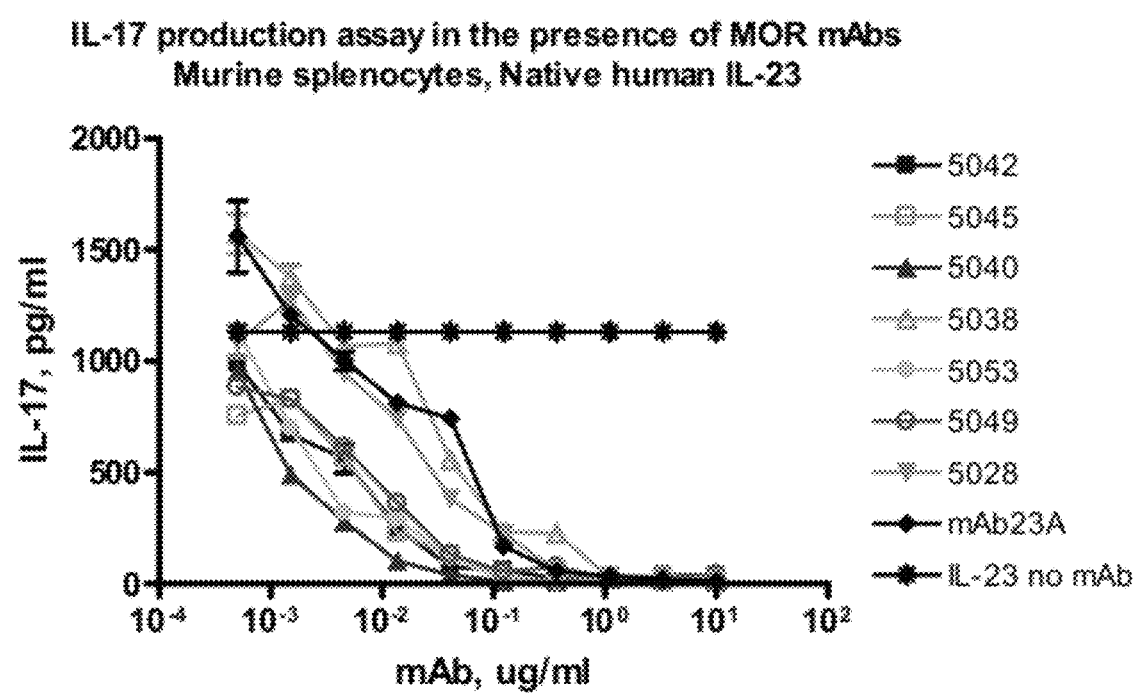
FIG. 8 shows that the IL-23p19 antibodies MOR05028, 05038, 05040, 05042, 05045, 05049, and 05053 of the invention inhibit recombinant hrIL-23 mediated IL-17 production.
Figure 9:
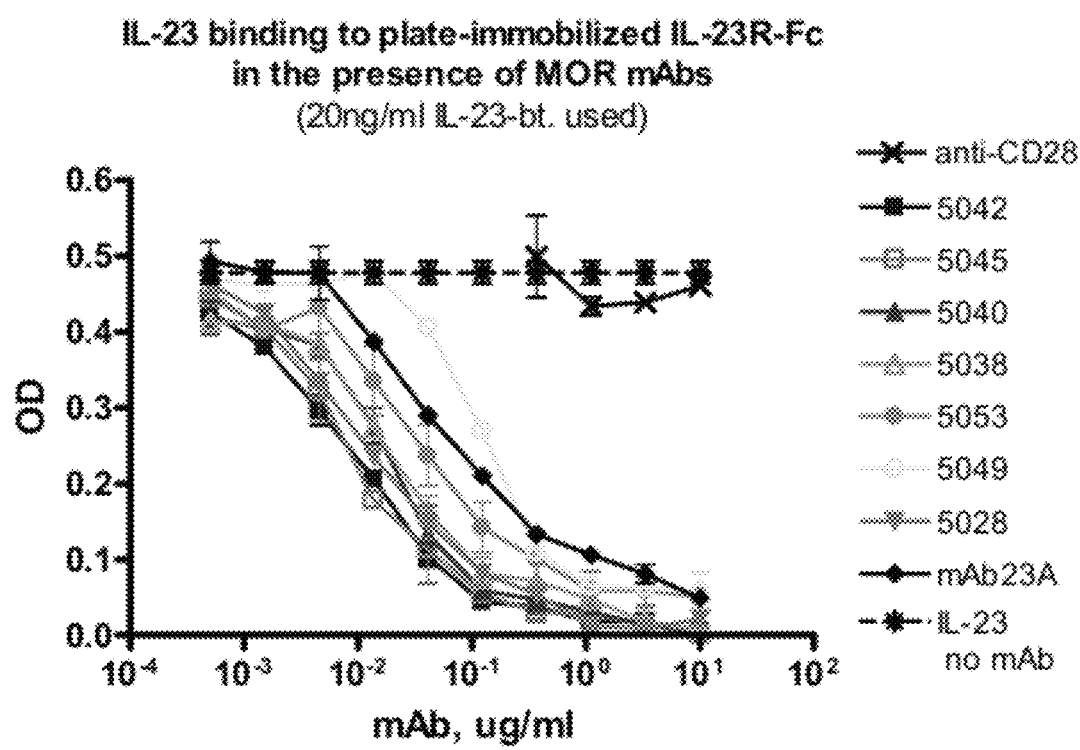
FIG. 9 shows the IL-23p19 antibodies MOR05028, 05038, 05040, 05042, 05045, 05049, and 05053 of the invention block normal IL-23/IL-23R binding.

From the combined activity and biochemical analysis, 7 mAbs were selected for more detailed analysis, at least one from each original parental antibody. Antibodies MOR05058 and 05059, derived from the VL CDR3 diversity libraries of MOR04649, were excluded from this set (see Examples 10 and 11). All selected candidates inhibited IL-17 production induced by native IL-23 from human (FIG. 8) and cynomologous monkey PBMCs (not shown). As expected, all inhibited hrIL-23 binding to hrIL-23R Fc fusion protein with a potency greater than that of the control mAb IL-23A (FIG. 9). With the possible exception of MOR05053, these selected mAbs did not inhibit native IL-12 bioactivity (not shown), consistent with the lack of binding of those available as Fabs to hrIL-12 protein.

Example 10

Production and Characterization of Cross-Chain Combination mAbs

The parent Fabs MOR04190, 04649, and 4658 gave rise to improved Fabs from both the VH CDR2 and VL CDR3 diversity libraries. The Fabs derived from MOR04649 were of particular interest due to their relatively potent activity from both types of libraries. However, the parental MOR04649Fab contains a predicted, but potentially unfavorable, N-linked glycosylation site in VH CDR2 that is not present in any of the 6 improved Fabs derived from the VH CDR2 library. To eliminate this glycosylation site and test for potential improved activity, the heavy chains of MOR05042 and 05045 were expressed with the light chains of MOR05058 and 5059 in HEK293 cells (Table 4C—mAbs 42-58, 42-59, 45-58, and 45-59). None of the combinations were more potent antagonists (IL-17 production and inhibition IL-23 binding to IL-23R) than the respective donor chain mAbs and each showed a greater tendency towards aggregation by size exclusion chromatography (not shown).

Example 11

Substitution Mutagenesis of Selected Matured mAbs and Their Characterization

Amino acid substitutions were introduced into selected mAbs to eliminate the predicted N-linked glycosylation site and/or conform the amino termini of variable regions with their closest predicted human germline V-region sequence. The predicted N-linked glycosylation site in the Vh of 5058 and 5059 ("NYS" in CDR2, same as in the parent Vh of MOR04649) was eliminated by substitution of arginine (4649r) or aspartic acid (4649d) for asparagine at position 59 (direct numbering). The CDR sequences of these VH regions are shown in Table 4A and the full V-region sequences are given in Table 8. These variants were produced by transient expression in HEK 293 cells and purified by Protein A affinity chromatography. These mAbs showed improved potency relative to the parental antibodies in their inhibition of IL-17 production. The arginine substitution in MOR05059 had the best profile based on activity and biochemical characterization and was named mAb 3759 Table 4C).

MAbs5040 and 3759 were selected as the top leads based on a their activities and biochemical characterization. Amino acid substitutions were introduced for conformity with human germline antibody sequence and a single amino acid substitution was made in the =5040 VL region to revert a framework mutation back to germline, substituting a valine for threonine at position 86.

The amino acid sequences changed from the original mAb format were as follows:

| Antibody | VH | VL |
|---|---|---|
| 5040 | E(3) to Q | D(1) to E, T(86) to V |
| 3759 | Q(1)E(3) to EQ | D(1)I(2) to QS |

The E3 to Q change in VH of both antibodies is reversion of an E substitution introduced upon cloning of the Fab into the mAb format vector. Q was present at this position in the original Fabs and can be used as a variant to the E substitution in various mAbs.

These variants are designated $5040^{Q/EV}$ and $3759^{EQ/QS}$. The component V-regions of $5040^{Q/EV}$ are 5040 VH and $4190^{EV}$ VL (Table 4C). The component V-regions of $3759^{EQ/QS}$ are $4649r^E$ VH and $5059^{QS}$ VL (Table 4C). The sequences of the CDRs and full V-regions of the component chains of both antibodies are shown in Tables 4 and 8, respectively. Similar substitutions can be identified for any of the candidates by comparison to their predicted human germline sequences.

Figure 10:
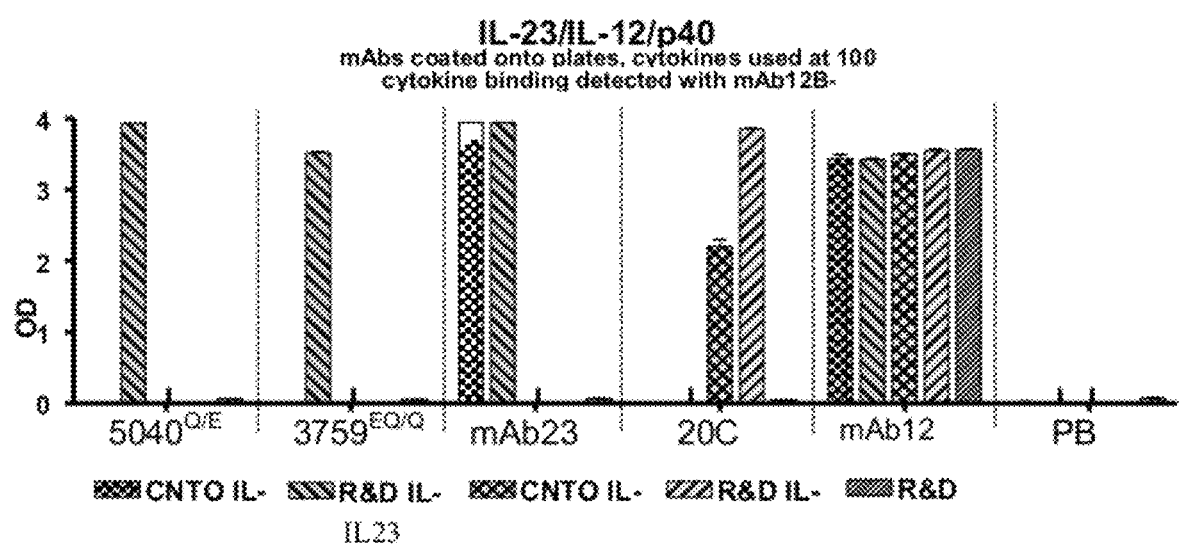
FIG. 10 shows that the IL-23p19 antibodies $5040^{Q/EV}$ and $3759^{EQ/QS}$ of the invention bind specifically to hrIL-23 and not hrIL-12 or hrp40 monomer, comparable to the anti-IL-23p19 murine monoclonal antibody, mAb23A. The anti-IL-12/IL-23p40 antibody mAb12A is shown to bind IL-23, IL-12 and the p40 monomer.
Figure 11A:
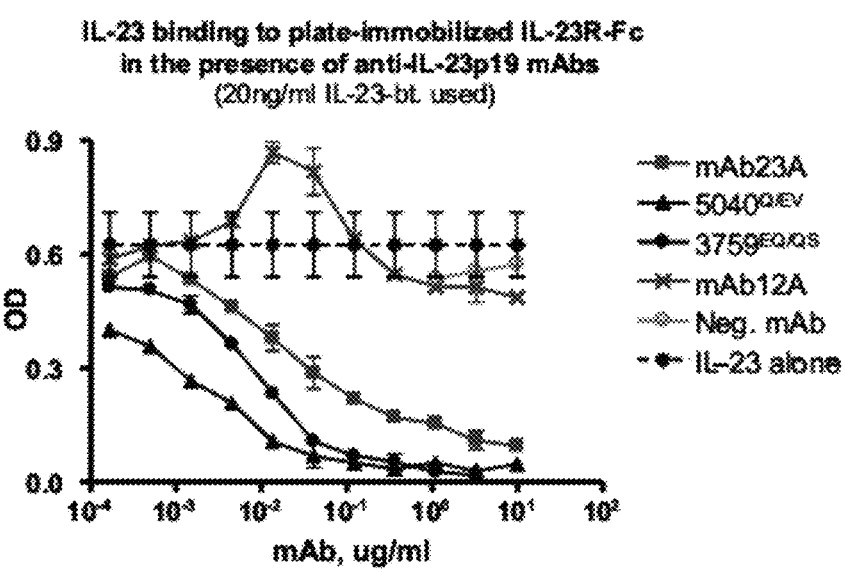
FIG. 11A shows that the IL-23p19 antibodies $5040^{Q/EV}$ and $3759^{EQ/QS}$ of the invention block normal IL-23/IL-23R binding.
Figure 11B:
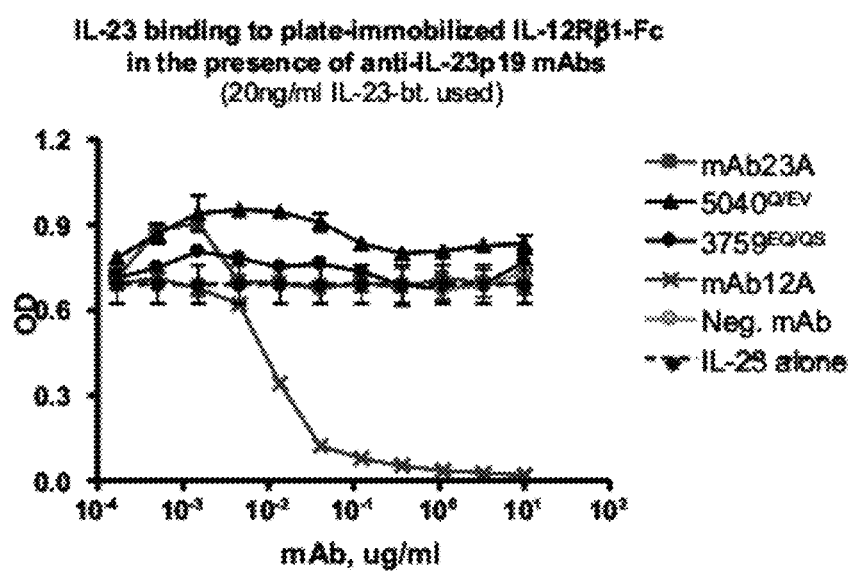
FIG. 11B shows that the IL-23p19 antibodies $5040^{Q/EV}$ and $3759^{EQ/QS}$ of the invention do not block normal IL-23/IL-12Rβ1 binding.
Figure 11C:
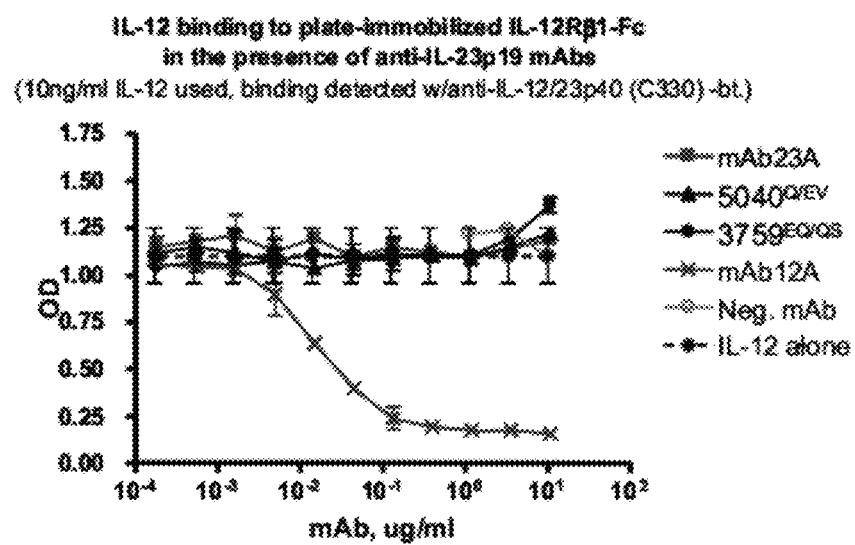
FIG. 11C shows that the IL-23p19 antibodies $5040^{Q/EV}$ and $3759^{EQ/QS}$ of the invention do not inhibit IL-12 binding to IL-12Rβ1-Fc binding.
Figure 12:
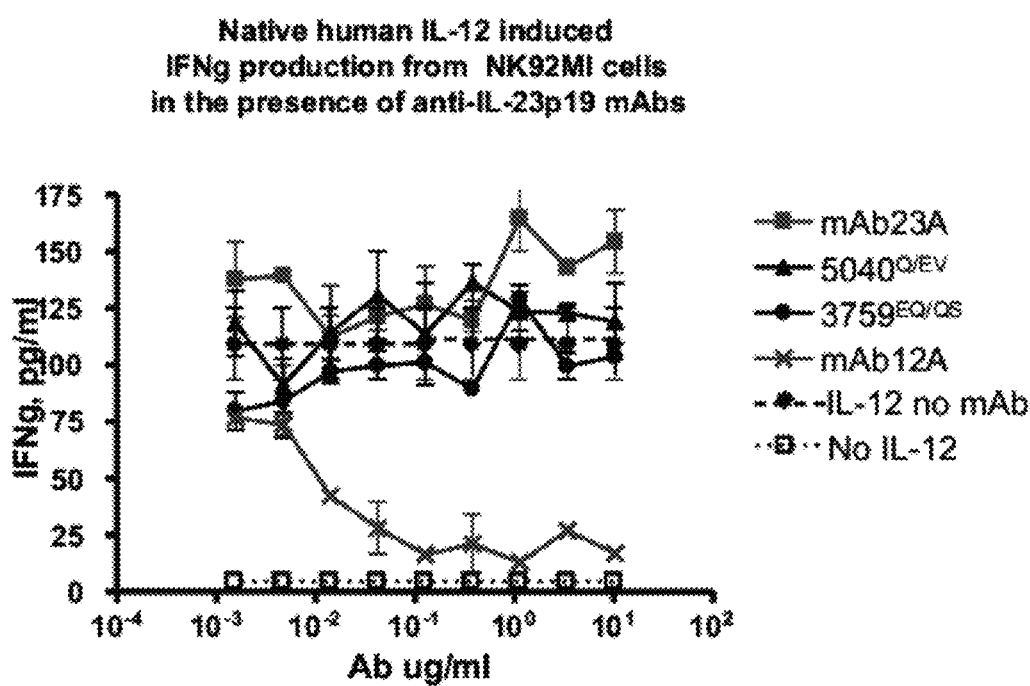
FIG. 12 shows that the IL-23p19 antibodies $5040^{Q/EV}$ and $3759^{EQ/QS}$ of the invention do not inhibit IL-12 induced INFγ production from NK92MI cells.
Figure 13:
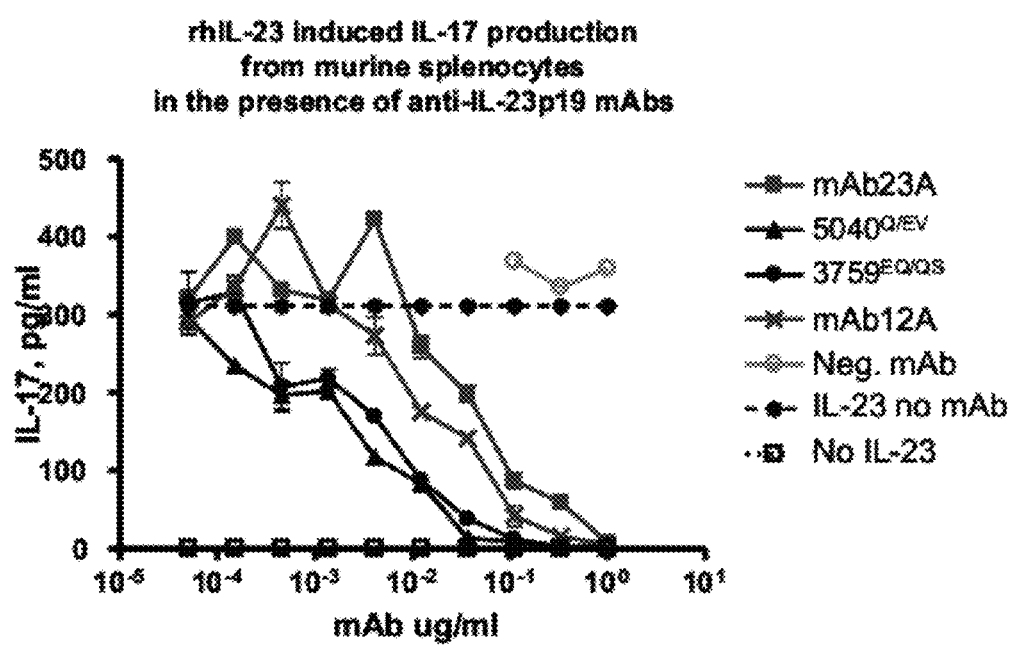
FIG. 13 shows that the IL-23p19 antibodies $5040^{Q/EV}$ and $3759^{EQ/QS}$ of the invention inhibit recombinant hrIL-23 mediated IL-17 production.
Figure 14:
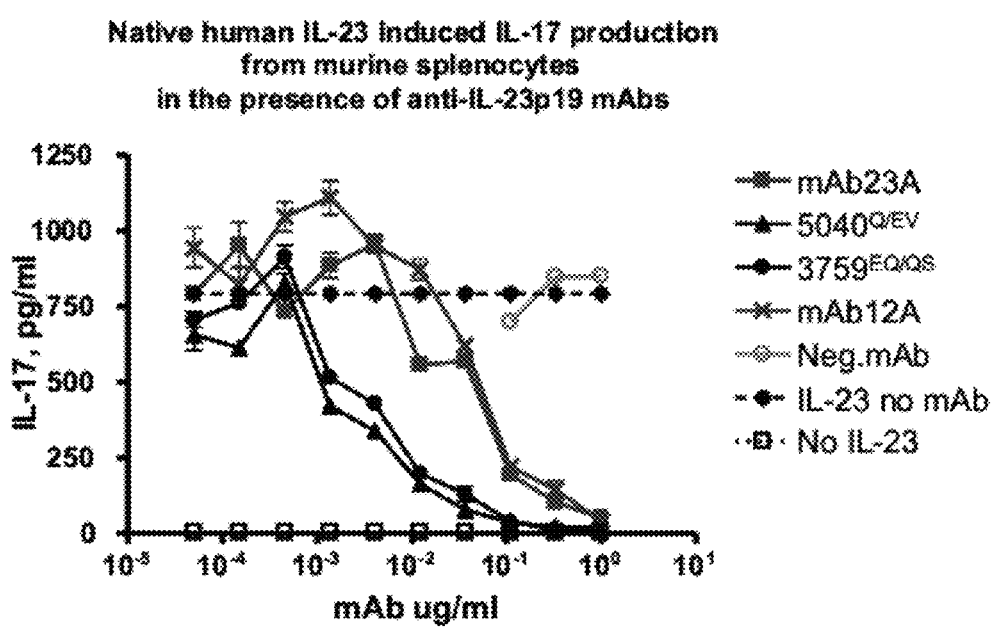
FIG. 14 shows that the IL-23p19 antibodies $5040^{Q/EV}$ and $3759^{EQ/QS}$ of the invention inhibit native hrIL-23 mediated IL-17 production.
Figure 15:
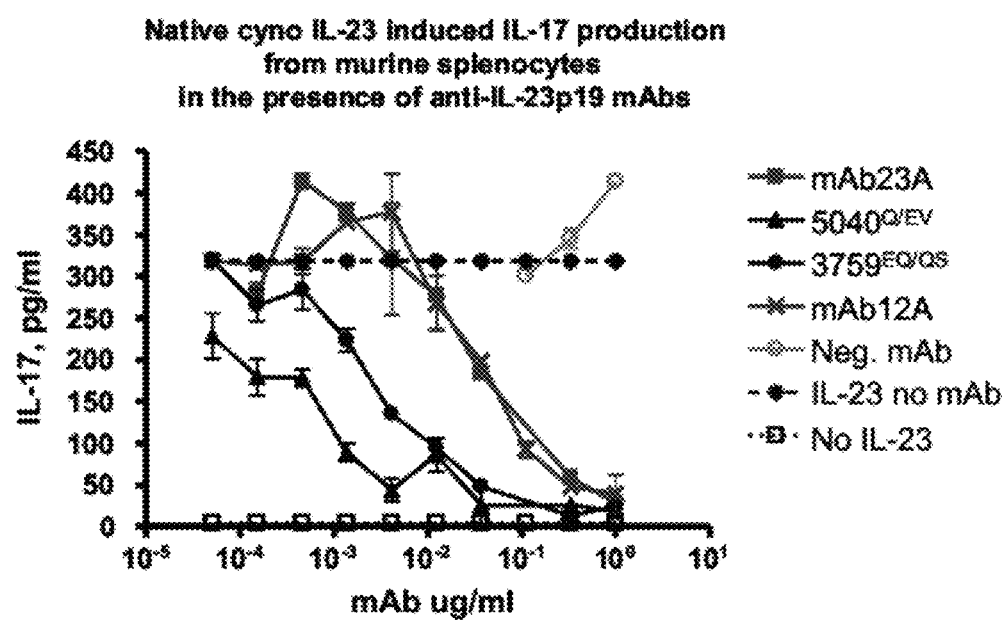
FIG. 15 shows that the IL-23p19 antibodies $5040^{Q/EV}$ and $3759^{EQ/QS}$ of the invention inhibit native cynomologous monkey IL-23 mediated IL-17 production.

The mAbs $5040^{Q/EV}$ and $3759^{EQ/QS}$ were produced by transient expression in HEK 293 cells and purified by Protein A affinity chromatography. These mAbs retain complete specificity for human IL-23 relative to IL-12 and p40, as shown in FIG. 10. These mAbs inhibit the binding of recombinant human IL-23 to IL-23R-Fc and are more potent than the reference, mAb23A (FIG. 11A). As expected from their specificity profile, they do not inhibit IL-23 (FIG. 11B) or IL-12 (FIG. 11C) binding to IL-12Rβ1. Consistent with this pattern of receptor inhibition, these mAbs do not inhibit IL-12 induced IFNγ production from NK92M1 cells (FIG. 12), but do inhibit both recombinant (FIG. 13) and native (FIG. 14) IL-23 induced production of IL-17 from murine splenocytes. These mAbs also show very strong inhibition of IL-17 induction by native IL-23 from cynomolgous monkey (FIG. 15), demonstrating a high degree of cross-reactivity with IL-23 from cynomolgous monkey. These mAbs also inhibited STAT3 phosphorylation induced in human NK cells by recombinant human IL-23 (not shown).

Figure 16A:
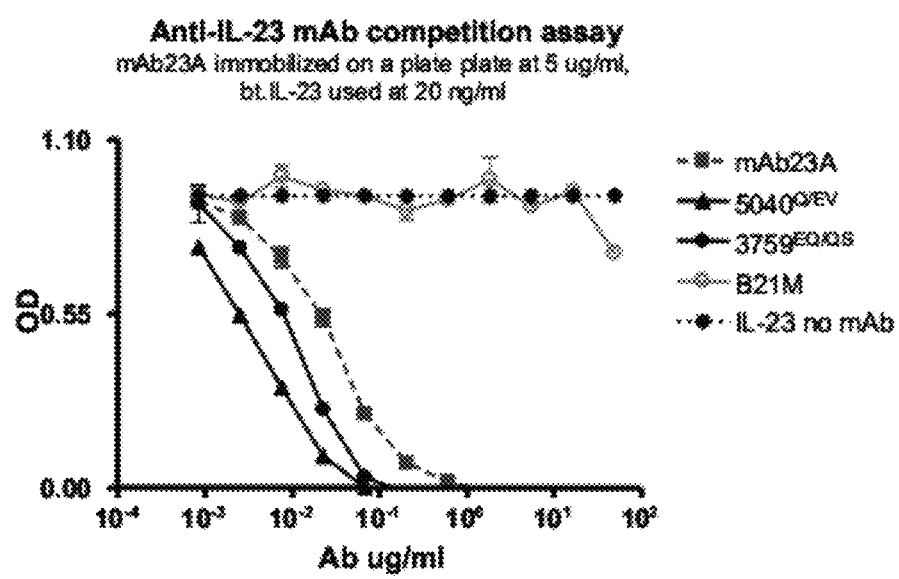
FIG. 16A shows that the IL-23p19 antibodies $5040^{Q/EV}$ and $3759^{EQ/QS}$ of the invention and mAb23A compete with the binding to of IL-23 to immobilized mAb23A.
Figure 16B:
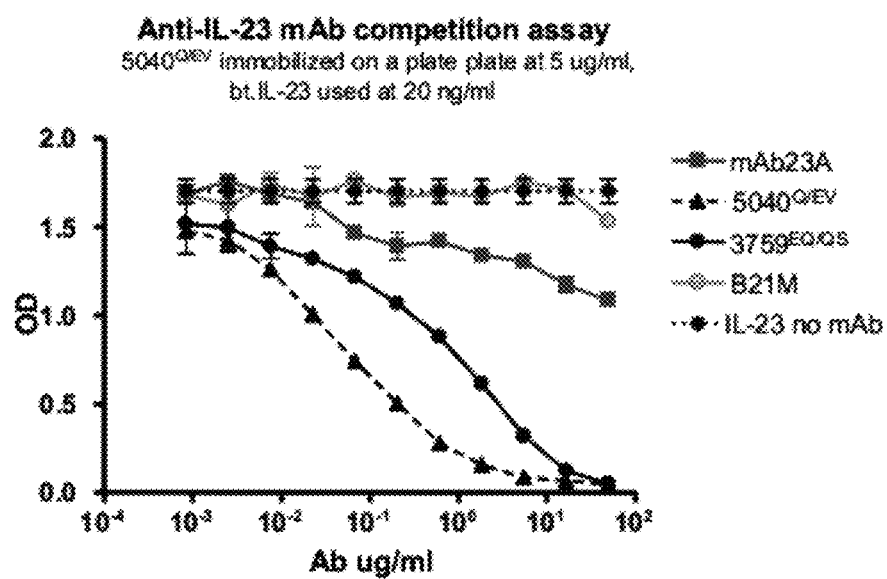
FIG. 16B shows that the IL-23p19 antibodies $5040^{Q/EV}$ and $3759^{EQ/QS}$ of the invention and, to a lesser extent, mAb23A compete with the binding to of IL-23 to immobilized $5040^{Q/EV}$ mAb.
Figure 16C:
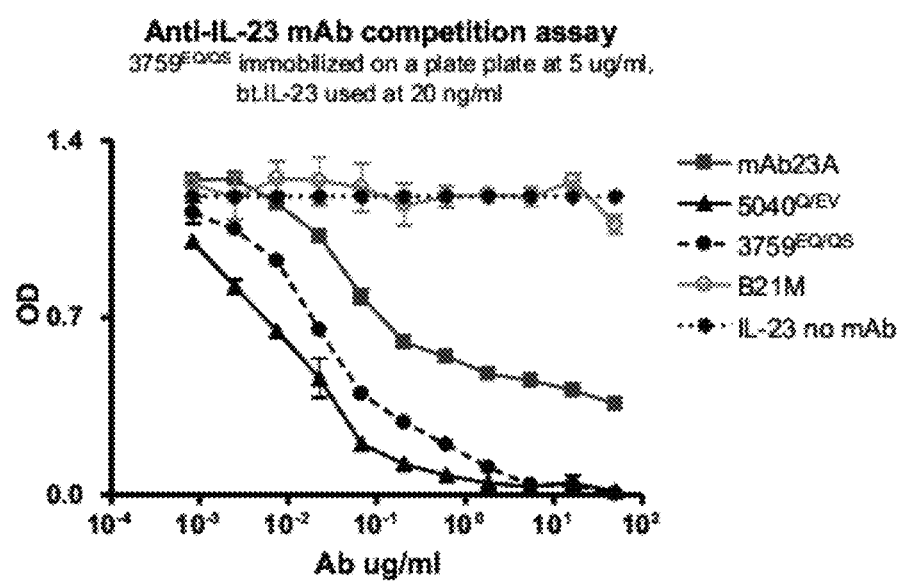
FIG. 16C shows that the IL-23p19 antibodies $5040^{Q/EV}$ and $3759^{EQ/QS}$ of the invention and mAb23A compete with the binding to of IL-23 to immobilized $3759^{EQ/QS}$ mAb.

The mAbs $5040^{Q/EV}$ and $3759^{EQ/QS}$ recognize closely positioned epitopes on IL-23 as demonstrated by their inhibition of mAB23A binding (FIG. 16A) and their reciprocal competition with each other (FIGS. 16B and 16C). The epitope of mAb23A has been mapped on human p19 in the region around 193-G105:

$I_{93}$HQGLIFYEKLLG$_{105}$ (SEQ ID NO: 148)

The competition results show that epitopes for mAbs $5040^{Q/EV}$ and $3759^{EQ/QS}$ lie in the same region.

Example 12

Coding Sequence Variants of mAbs $5040^{Q/EV}$ and $3759^{EQ/QS}$ and Their Characterization The coding sequence of the variable regions of the antibodies were engineered into three different coding sequence variants to evaluate the impact on expression of these proteins. The first variant used the codons as obtained from the original library, with a few nucleotide substitutions to remove consensus mRNA splice sites. The second variant, germline codon exchange (GCE), was designed by aligning the variable region amino acid sequences to germline genes, identifying the closest matching germline gene and replacing the codons in the original coding sequence with the synonymous codons that are used in the germline gene. At positions where the amino acid residue did not have a match to germline genes, the codon that is used at the highest frequency in highly expressed human proteins was substituted for the original codon. The third codon variant was designed by replacing the starting antibody codons with the codon that is used at the highest frequency in highly expressed human proteins. Each codon variant did express as measured by transient transfection in HEK 293 cells and CHO cells. This result shows that stable cell line transfectants can be established in these, and likely other host cells and the highest expressing variant can be used for development of a production cell line. The mAbs are evaluated as described in Example 11, in addition to other functional and biochemical and biophysical properties analyses. Table 9 shows the variable heavy and light chain nucleotide sequences for the $5040^{Q/EV}$ and $3759^{EQ/QS}$ mAb variants.

For the purposes of this invention, 70-100% amino acid or nucleotide sequence identity (i.e., 90, 91, 92, 93, 94, 95, 96, 97, 98, 99, 100 or any range or value therein) is determined using a suitable computer algorithm, as known in the art.

It will be clear that the invention can be practiced otherwise than as particularly described in the foregoing description and examples. Numerous modifications and variations of the present invention are possible in light of the above teachings and, therefore, are within the scope of the appended claims.

TABLE 1

Binding Specificity of Candidate Fabs

| | Specificity ELISA: Antigens in solution to immobilized Fabs | | | | | Biacore (Fab capture mode) $K_D$ [nM] | |
|---|---|---|---|---|---|---|---|
| MOR0# | IL-23 CNTO | IL-23 R&D | IL-12 CNTO | IL-12 R&D | p40 R&D | IL-23 CNTO | IL-12 CNTO |
| 4083 | + | nd | – | nd | nd | 16 | no binding |
| 4086 | + | nd | – | nd | nd | 36 | no binding; n: 3 |
| 4185 | + | nd | – | nd | nd | 79 | no binding |
| 4190 | + | nd | – | nd | nd | 11 | no binding |
| 4205 | + | + | – | – | – | 140 | slight binding* |

TABLE 1-continued

Binding Specificity of Candidate Fabs

| MOR0# | Specificity ELISA: Antigens in solution to immobilized Fabs | | | | | Biacore (Fab capture mode) $K_D$ [nM] | |
|---|---|---|---|---|---|---|---|
| | IL-23 CNTO | IL-23 R&D | IL-12 CNTO | IL-12 R&D | p40 R&D | IL-23 CNTO | IL-12 CNTO |
| 4217 | | + | − | − | − | 41 | slight binding* |
| 4235 | + | | − | − | − | 65 | slight binding* |
| 4491 | + | | − | − | − | 190 | no binding |
| 4647 | + | | − | − | − | 12 | |
| 4649 | + | + | − | − | − | 7 | |
| 4651 | + | + | − | − | − | 160 | no binding |
| 4655 | + | | | | | 66 | no binding |
| 4658 | + | + | − | − | − | 11 | no binding |
| Fab12A | + | + | + | + | + | 1.1 | 0.6 |

TABLE 2

IC50 of Candidate Fabs in hrIL-23/hIL-23R Assay

| MOR0# | IC50 [nM] |
|---|---|
| 4083 | 4.6 +/− 3.9 |
| 4086 | no complete inhibition |
| 4185 | 280 |
| 4190 | 4.8 +/− 2 |
| 4205 | 38 |
| 4217 | 16 |
| 4235 | 190 |
| 4491 | 10~50% inhibition |
| 4647 | 2.1 |
| 4649 | 0.2 +/− 0.2 |
| 4651 | 36 |
| 4655 | 286 |
| 4658 | 0.7 |
| IL-23R-Fc | 1.8 +/− 1.8 |

TABLE 3

Characterization of the Parental Antibodies in a mAb Format.

| mAb MOR# | IL-23 binding hrIL-23 subunit specificity | Biochemical receptor binding assays | | | pSTAT3 Assay Results at noted concentration | IL-12 bioassay in NK92MI IFNg in NK92MI cells | IL-23 induced IL-17 production assay | | |
|---|---|---|---|---|---|---|---|---|---|
| | | IL-12/ IL-12Rb1 | IL-23/ IL-12Rb1 | IL-23/ IL-23R | | | hrIL-17 neutralization | Native human IL-23 neutralization | Native cyno IL 23 neutralation |
| 4083 (κ) | p19 | − | − | + | +/− at 10<br>+ at 20 | − | + | + | + |
| 4190 (κ) | p19 | − | − | + | + at 10 | − | + | + | + |
| 4649 (λ) | p19 | − | − | + | +/− at 1<br>+ at 10 | − | + | + | + |
| 4658 (λ) | p19 | − | − | +/− | −/+ at 10 | − | −/+ | + | + |
| 4205 | p19 | − | − | −/+ | + at 10 | N/d | − | N/d | N/d |
| 4217 | p19 | − | − | −/+ | − at 10 | N/d | −/+ | N/d | N/d |
| 4185 | p19 | − | − | −/+ | − at 7 | − | − | N/d | N/d |
| 4235 | p19 | − | − | −/+ | − at 10 | − | − | N/d | N/d |
| 4090 | p19 | − | − | − | N/d | N/d | − | N/d | N/d |
| 4647 | p19 | − | − | +/− | − at 10 | − | − | N/d | N/d |
| 4491 | p19 | − | − | +/− | − at 10 | − | − | N/d | N/d |
| 4651 | p19 | − | − | +/− | − at 10 | − | − | N/d | N/d |
| 4085 | p19* | − | − | − | − at 3 | − | − | N/d | N/d |
| 4086 | p19* | − | − | − | − at 5 | N/d | +*** | N/d | N/d |
| 4655 | p19* | − | − | − | − at 10 | − | +*** | N/d | N/d |
| 4193 | IL-12/IL-23p40 | − | − | −/+ | − at 6 | + | + | N/d | N/d |
| 4201 | IL-12/IL-23p40 | − | +, no titration | −/+ | N/d | + | + | N/d | N/d |
| 4704 | IL-12/IL-23p40 | −/+** | −/+ | −/+ | + at 10 | + | + | N/d | N/d |

| Symbol | Description |
|---|---|
| − | No inhibition |
| −/+ | Slight Inhibition |
| +/− | Weak, incomplete inhibition |
| + | Inhibition |
| * | Did not bind to linked rhIL-23 with no His-tag (from R&D Systems) |
| ** | Better inhibits R&D IL-12, than CNTO IL-12 |
| *** | Caused cell death at high concentration |
| N/d | Not done |

TABLE 4A

Hc V-region CDR sequences of candidate antibodies

| Clone # | H-CDR1 VH (SEQ ID NO:) | H-CDR2 (SEQ ID NO:) | H-CDR3 (SEQ ID NO:) | Comments |
|---|---|---|---|---|
| 4083 | IA NYAIS (1) | GIIPMFGYANYAQKFQG (7) | DIYAGMD V (40) | Primary hit |

TABLE 4A-continued

Hc V-region CDR sequences of candidate antibodies

| Clone # | VH | H-CDR1 (SEQ ID NO:) | H-CDR2 (SEQ ID NO:) | H-CDR3 (SEQ ID NO:) | Comments |
|---|---|---|---|---|---|
| 5028 | | | GIIPVFGFTHYAQKFQG (8) | | Affinity maturation |
| 4190 | 1A | SNYIS (2) | GIIPIFGHANYAQKFQG (9) | SKKGMYG GWTYPLM MFDL (41) | Primary hit |
| 5033 | | | IIIPPIGNAWYAQKFQG (10) | | Affinity maturation |
| 5034 | | | LIDPNFGGAYYAQKFQG (11) | | Affinity maturation |
| 5036 | | | LIDPVFGGAYYAQKFQG (12) | | Affinity maturation |
| 5037 | | | LIDPMFGGAYYAQKFQG (13) | | Affinity maturation |
| 5038 | | | -INAHLGGTWYAQKFQG (14) | | Affinity maturation |
| 5040 | | | ISPGTGINAYYAQKFQG (15) | | Affinity maturation |
| 4190x | | | $Z_1Z_2Z_3Z_4Z_5Z_6Z_7Z_8Z_9Z_{10}$YAQKFQG! ! (16) | | Predicted |
| 4205 | 5 | NYWIS (3) | WIRPGDSDTRYSPSFEG (17) | HYYGMDY (42) | Primary hit |
| 4217 | 3 | 1.1.1.1.1 sywit (4) | VSYISSSGSSTYYADSVKG (18) | GTFWSFG NYFAN (43) | Primary hit |
| 4649 | 5 | NYWIG (5) | IIDPSNSYT<u>NYS</u>PSFQG (19) | WYYKPFD V (44) | Primary hit |
| 4649r | | | IIDPSNSYTRYSPSFQG (20) | | Δ glycosylation site |
| 4649r$^E$ | | | IIDPSNSYTRYSPSFQG | | Plus E1 substitutions |
| 4649d | | | IIDPSNSYTDYSPSFQG (21) | | Δ glycosylation site |
| 5041 | | | IISPTGSVTWYSPSFQG (22) | | Affinity maturation |
| 5042 | | | IISPTGSSTWYSPSFQG (23) | | Affinity maturation |
| 5043 | | | FISPDGSHTWYSPSFQG (24 | | Affinity maturation |
| 5044 | | | IISPSGSTTWYSPSFQG (25) | | Affinity maturation |
| 5045 | | | IISPTGSATWYSPSFQG (26) | | Affinity maturation |
| 5046 | | | IIDPVSSWTKYSPSFQG (27) | | Affinity maturation |
| 4649x | | | II$X_1$P$X_2X_3$S$X_4$T$X_5$YSPSFQG ** (28) | | predicted |

TABLE 4A-continued

Hc V-region CDR sequences of candidate antibodies

| Clone # | VH | H-CDR1 (SEQ ID NO:) | H-CDR2 (SEQ ID NO:) | H-CDR3 (SEQ ID NO:) | Comments |
|---|---|---|---|---|---|
| 4658 | 3 | SFGMS (6) | NISSSGSS--TYYADSVKG (29) | YWGTPYLMQFDN (45) | Primary hit |
| 5039 | | | NIEHKYLNYATYYAASVKG (30) | | Affinity maturation |
| 5047 | | | NIEHKYLGYATSYAASVKG (146) | | Affinity maturation |
| 5048 | | | NIEHKFMGYTTYYAAGVKG (31) | | Affinity maturation |
| 5049 | | | GIEHKYLSYTTHYAASVKG (32) | | Affinity maturation |
| 5050 | | | SIEHKYTGYTTYYAAPVKG (33) | | Affinity maturation |
| 5051 | | | QIEHKYLSYTTLYAASVKG (34) | | Affinity maturation |
| 5052 | | | SIEHKYLSYTTFYAASVKG (35) | | Affinity maturation |
| 5053 | | | NIEGKYTSYTTYYAASVKG (36) | | Affinity maturation |
| 5054 | | | GIEHKYLSYATLYAASVKG (37) | | Affinity maturation |
| 5055 | | | NIEHKYLGYATVYAASVKG (38) | | Affinity maturation |
| 5056 | | | SIEHKYLSYATYYAAGVKG (39) | | Affinity maturation |

All antibodies expressed as Fabs have Q at residue 3 in Vh, whereas when expressed as mAbs, most had E at residue 3.
** $X_1$ is D or S; $X_2$ is S, V, D, or T; $X_3$ is N, S, or G; $X_4$ is Y, W, T, H, V, S, or A; $X_5$ is N, D, R, K, or W
! ! $Z_1$ is G, I, or L; $Z_2$ is I or S; $Z_3$ is I, P, N, or D; $Z_4$ is P, G, or A; $Z_5$ is I, M, P, T, H, N, or V; $Z_6$ is F, I, G, or L; $Z_7$ G or I; $Z_8$ is H, Y, N, or G; $Z_9$ is A or T; $Z_{10}$ is N, W, or Y
++ $a_1$ is S or A; $a_2$ is T or G; $a_3$ is P or L; $a_4$ is S or N; $a_5$ is S, M, or L; $a_6$ is I or V
$b_1$ is T, F, D, or S; $b_2$ is S, I, A, T, R, or L; $b_3$ is N, T, L, S, or G; $b_4$ is T, Y, S, or I; $b_5$ is P or L; $b_6$ is F or P

TABLE 4B

Lc V-region CDR sequences of candidate antibodies

| Clone # | VL | L-CDR1 (SEQ ID NO:) | L-CDR2 (SEQ ID NO:) | L-CDR3 (SEQ ID NO:) | Comments |
|---|---|---|---|---|---|
| 4083 | κ3 | RASQSVLGNYLA (46) | GASSRAT (52) | HQYGSISTT (58) | Primary hit |
| 5267 | | | | QQYSHLLIT (59) | Affinity maturation |
| 5268 | | | | QQYSHISLT (60) | Affinity maturation |
| 5269 | | | | QQFAHILLT (61) | Affinity maturation |
| 4190 | κ3 | RASQSVSSNYLA (47) | YASRRAT (53) | QQTSNTPFT (62) | Primary hit |

TABLE 4B-continued

Lc V-region CDR sequences of candidate antibodies

| Clone # | VL | L-CDR1 (SEQ ID NO:) | L-CDR2 (SEQ ID NO:) | L-CDR3 (SEQ ID NO:) | Comments |
|---|---|---|---|---|---|
| 4190[EV] | | | | QQTSNTPFT | Plus E1 & V86 substitutions |
| 5029 | | | | QQFITYLPT (63) | Affinity maturation |
| 5030 | | | | QQDALSPFT (64) | Affinity maturation |
| 5031 | | | | QQDRGTPFT (65) | Affinity maturation |
| 5032 | | | | QQSLNIPFT (66) | Affinity maturation |
| 5057 | | | | QQDTSSPFT (67) | Affinity maturation |
| 4190x | | | | QQ$b_1b_2b_3b_4b_5b_6$FT## (68) | Predicted |
| 4205 | λ1 | SGSSSNIGSYYVN (48) | GNTHRPS (54) | QTYASLGPGEV (69) | Primary Hit |
| 4217 | κ1 | RASQSIFYNLA (49) | GASNRAT (55) | QQYSSEPVT (70) | Primary Hit |
| 4649 | λ1 | TGSSSNIGSGYDVH (50) | GNSKRPS (56) | SSWT--PSSVV (71) | Primary hit |
| 5058 | | | | SSWTDTPNMIV (72) | Affinity maturation |
| 5059 | | | | ASWTDGLSLVV (73) | Affinity maturation |
| 5059[QS] | | | | ASWTDGLSLVV | Plus Q1, S2 substitutions |
| 4649x | | | | $a_1$SWTD$a_2a_3a_4a_5a_6$V++ (74) | Predicted |
| 4658 | λ2 | TGTSSDVGGYNSVS (51) | SVSSRPS (57) | SSYDTNKPLVV (75) | Primary hit |
| 5060 | | | | GSYDVYGRFYV (76) | Affinity maturation |
| 5061 | | | | SSYYFYLQRIV (77) | Affinity maturation |
| 5062 | | | | QTYYFSYSGPV (78) | Affinity maturation |
| 5063 | | | | GSWDPIFSYEV (79) | Affinity maturation |

TABLE 4C

Antibodies produced, purified and evaluated

| Ab Name | VH | VL | Fab*[#] | MAb* | Comments |
|---|---|---|---|---|---|
| 4083 | 4083 | 4083 | x | x | |
| 5028 | 5028 | 4083 | x | x | |
| 5267** | 4083 | 5267 | x | (in progress) | |
| 5268** | 4083 | 5268 | x | (in progress) | |
| 5269** | 4083 | 5269 | x | (in progress) | |
| 4190 | 4190 | 4190 | x | x | |
| 5033 | 5033 | 4190 | | x | |
| 5034 | 5034 | 4190 | x | x | |
| 5036 | 5036 | 4190 | x | x | |
| 5037 | 5037 | 4190 | | x | |

TABLE 4C-continued

Antibodies produced, purified and evaluated

| Ab Name | VH | VL | Fab*# | MAb* | Comments |
|---|---|---|---|---|---|
| 5038 | 5038 | 4190 | x | x | |
| 5040 | 5040 | 4190 | | x | |
| 5040$^{Q/EV}$ | 5040 | 4190$^{EV}$ | | x | Vh-Q3 back substitution in mAb |
| 5029** | 4190 | 5029 | | x | |
| 5030** | 4190 | 5030 | | x | |
| 5031** | 4190 | 5031 | | x | |
| 5032** | 4190 | 5032 | | x | |
| 5057** | 4190 | 5057 | | x | |
| 4205 | 4205 | 4205 | x | x | |
| 4217 | 4217 | 4217 | x | x | |
| 4649 | 4649 | 4649 | x | x | |
| 5041 | 5041 | 4649 | x | x | |
| 5042 | 5042 | 4649 | x | x | |
| 42-58 | 5042 | 5058 | | x | Pair 5058 VL with VH lacking CDR2 glycosylation site |
| 42-59 | 5042 | 5059 | | x | Pair 5059 VL with VH lacking CDR2 glycosylation site |
| 5043 | 5043 | 4649 | x | x | |
| 5044 | 5044 | 4649 | x | x | |
| 5045 | 5045 | 4649 | x | x | |
| 45-58 | 5045 | 5058 | | x | Pair 5058 VL with VH lacking CDR2 glycosylation site |
| 45-59 | 5045 | 5059 | | x | Pair 5059 VL with VH lacking CDR2 glycosylation site |
| 5046 | 5046 | 4649 | x | x | |
| 5058 | 4649 | 5058 | x | x | |
| 5059 | 4649 | 5058 | x | x | |
| 3758 | 4649r | 5058 | | x | |
| 3759 | 4649r | 5059 | | x | |
| 3759$^{EQ/QS}$ | 4649r$^E$ | 5059$^{QS}$ | | x | Vh-Q3 substitution in mAb |
| 3658 | 4649d | 5058 | | x | |
| 3659 | 4649d | 5059 | | x | |
| 4658 | 4658 | 4658 | x | x | |
| 5039 | 5039 | 4658 | x | x | |
| 5047 | 5047 | 4658 | x | x | |
| 5048 | 5048 | 4658 | x | x | |
| 5049 | 5049 | 4658 | x | x | |
| 5050 | 5050 | 4658 | x | x | |
| 5051 | 5051 | 4658 | | x | |
| 5052 | 5052 | 4658 | x | x | |
| 5053 | 5053 | 4658 | x | x | |
| 5054 | 5054 | 4658 | | x | |
| 5055 | 5055 | 4658 | x | x | |
| 5056 | 5056 | 4658 | | x | |
| 5060 | 4658 | 5060 | x | x | |
| 5061 | 4658 | 5061 | x | x | |
| 5062 | 4658 | 5062 | x | x | |
| 5063 | 4658 | 5063 | x | x | |

*Except as indicated in the "comments" box, position 3 in the heavy chain was Q in the Fabs and E in the mAbs.
**The affinity matured kappa light chains of 4083 and 4190 contain a T to V substitution relative to the parents in FW3 (FAVYYC). V is a germline residue at this position.
Several Fabs listed as "affinity matured" showed some aggregation during purification and thus were not evaluated. They were previously evaluated as hits as crude samples.

TABLE 5

Characterization of Affinity-Matured Fabs: specificity, receptor neutralization, and affinity.

| MOR0# | Library | $K_D$ [pM] SET (n: 1) | IL-23/IL-23R IC$_{50}$ [nM] (n: 1-4) | IL-23/ IL-12R$^b$1 | IL-12 (R&D)/ IL-12R$^b$1 | Specificity ELISA | FACS (TALL-104) |
|---|---|---|---|---|---|---|---|
| 4083 | — | 1600 | 7.1 ± 8.3 | O.K. | O.K. | O.K. | — |
| 5028 | H-CDR2 | 133 | 0.43 ± 0.58 | O.K. | O.K. | O.K. | — |
| 5267 | L-CDR3 | 2000 | 0.14 | O.K. | O.K. | n.d. | n.d. |
| 5268 | | 660 | 0.15 | O.K. | O.K. | n.d. | n.d. |
| 5269 | | 960 | 0.2 | O.K. | O.K. | n.d. | n.d. |
| 4190 | — | 4400 | 1.3 ± 1.5 | O.K. | O.K. | O.K. | — |
| 5034 | H-CDR2 | 126 | 0.4 ± 0.15 | O.K. | O.K. | O.K. | — |
| 5036 | | 32 | 0.32 ± 0.02 | O.K. | O.K. | O.K. | — |
| 5038 | | 38 | 0.17 ± 0.05 | O.K. | O.K. | O.K. | — |
| 4649 | — | 1100 | 1.2 | O.K. | O.K. | O.K. | — |
| 5041 | H-CDR2 | 41 | 0.07 ± 0.04 | O.K. | O.K. | O.K. | — |
| 5042 | | 4 | 0.06 ± 0.03 | O.K. | O.K. | O.K. | — |
| 5043 | | 18 | 0.05 ± 0.03 | O.K. | O.K. | O.K. | — |
| 5044 | | 43 | 0.05 ± 0.04 | O.K. | O.K. | O.K. | — |
| 5045 | | 9 | 0.05 ± 0.02 | O.K. | O.K. | O.K. | — |
| 5046 | | 23 | 0.08 ± 0.01 | O.K. | O.K. | O.K. | — |
| 5058 | L-CDR3 | 33 | 0.11 ± 0.08 | O.K. | O.K. | O.K. | — |
| 5059 | | 93 | 0.69 ± 0.72 | O.K. | O.K. | O.K. | — |

TABLE 6

Characterization of Affinity-Matured Fabs: specificity, receptor neutralization, and affinity.

| MOR0# | Library | $K_D$ [pM] SET (n: 1) | IL-23/IL-23R IC$_{50}$ [nM] (n: 1-4) | IL-23/ IL-12R$^b$1 | IL-12 (R&D)/ IL-12R$^b$1 | Specificity ELISA | FACS (TALL-104) |
|---|---|---|---|---|---|---|---|
| 4658 | — | 4300 | 14 | O.K. | O.K. | O.K. | — |
| 5039 | H-CDR2 | 27 | 0.1 ± 0.09 | O.K. | O.K. | O.K. | — |
| 5047 | | 36 | 0.13 ± 0.1 | O.K. | O.K. | O.K. | — |

TABLE 6-continued

Characterization of Affinity-Matured Fabs: specificity, receptor neutralization, and affinity.

| MOR0# | Library | $K_D$ [pM] SET (n: 1) | IL-23/IL-23R $IC_{50}$ [nM] (n: 1–4) | IL-23/ IL-12R$^{b}$1 | IL-12 (R&D)/ IL-12R$^{b}$1 | Specificity ELISA | FACS (TALL –104) |
|---|---|---|---|---|---|---|---|
| 5048 | | 20 | 0.1 ± 0.1 | O.K. | O.K. | O.K. | — |
| 5049 | | 7 | 0.39 ± 0.62 | O.K. | O.K. | O.K. | — |
| 5050 | | 23 | 0.89 ± 1.15 | O.K. | O.K. | O.K. | — |
| 5052 | | 10 | 0.58 ± 0.74 | O.K. | O.K. | O.K. | — |
| 5053 | | 27 | 0.98 ± 1.3 | O.K. | O.K. | O.K. | — |
| 5055 | | 29 | 0.79 ± 1.0 | O.K. | O.K. | O.K. | — |
| 5056 | | 65 | 0.52 ± 0.68 | O.K. | O.K. | O.K. | — |
| 5060 | L-CDR3 | 142 | 1.0 ± 1.14 | O.K. | O.K. | O.K. | — |
| 5061 | | 58 | 1.25 ± 1.49 | O.K. | O.K. | O.K. | — |
| 5062 | | 98 | 1.34 ± 1.5 | O.K. | O.K. | O.K. | — |
| 5063 | | 69 | 0.32 ± 0.25 | O.K. | O.K. | O.K. | — |

TABLE 7

Characterization of Affinity-Matured Antibodies in mAb Format: Inhibition of IL-17 production.
Inhibition of hrIL-23 binding to immobilized IL-23R-Fc fusion protein.
IC50 values from titration curves.
The mAbs (see Table 4C) are listed in order of decreasing potency.
The matured antibodies are grouped according to their respective parents:
pink (5028 is from 4083); (5040, 5038, 5029, 5030, 5057, 5036, 5032, 5034, 5033, and 5037 are with 4190); (5042, 5045, 5058, 5041, 5059, 5044, 5043, 5046, and 4083 are with 4649); (5054, 5053, 5049, 5048, 5052, 5047, 5050, 5051, 5055, 5056, 5039, 5063, 5062, and 5061 are with 4658). MAb 23A is a reference murine anti-human IL-23 mAb

| mAb | IC50, ug/ml |
|---|---|
| 5042 | 0.00127 |
| 5045 | 0.001396 |
| 5040 | 0.002641 |
| 5058 | 0.002847 |
| 5041 | 0.003007 |
| 5054 | 0.003227 |
| 5053 | 0.00493 |
| 5059 | 0.01062 |
| 5044 | 0.01414 |
| 5043 | 0.01439 |
| 5049 | 0.01616 |
| 5048 | 0.01624 |
| 5052 | 0.0178 |
| 5047 | 0.02342 |
| 5050 | 0.02766 |
| 5038 | 0.02815 |
| 5046 | 0.04281 |
| 5029 | 0.04907 |
| mAb23A | 0.05415 |
| 5030 | 0.06458 |
| 5051 | 0.0663 |
| 5055 | 0.09155 |
| 5056 | 0.09198 |
| 5028 | 0.1039 |
| 5057 | 0.1103 |
| 5039 | 0.1606 |
| 5036 | 0.1702 |
| 5032 | 0.1716 |
| 5034 | 0.1854 |
| 5063 | 0.1981 |
| 5062 | 0.1989 |
| 5031 | 0.2149 |
| 4190 | 0.218 |
| 4649 | 0.2758 |
| 5033 | 0.2834 |
| 5061 | 0.3087 |
| 5037 | 0.3364 |
| 4083 | 1.395 |
| 4658 | 1.956 |

TABLE 8

Sequences of initial IL-23p19 mAbs and their matured and engineered derivatives.

MOR04083 Family

```
            (SEQ ID NOS: 80 & 81)
            1
117
4083 Vh     (1)
            QVQLVQSGAEVKKPGSSVKVSCKASGGTFSNYAISWVRQAPGQGLEWMGGIIPMFGYANYAQKFQGRVTITADESTSTA
            YMELSSLRSEDTAVYYCARDIYAGMDVWGQGTLVTVSS

5028 Vh     (1)
            QVQLVQSGAEVKKPGSSVKVSCKASGGTFSNYAISWVRQAPGQGLEWMGGIIPvFGfthYAQKFQGRVTITADESTSTA
            YMELSSLRSEDTAVYYCARDIYAGMDVWGQGTLVTVSS
```

TABLE 8-continued

Sequences of initial IL-23p19 mAbs and their matured and engineered derivatives.

|  |  |
|---|---|
| | (SEQ ID NOS: 82-85)<br>1 |
| 108 | |
| 4083 Vk | (1)<br>DIVLTQSPATLSLSPGERATLSC<u>RASQSVLGNYLA</u>WYQQKPGQAPRLLIY<u>GASSRAT</u>GVRARFSGSGSGTDFTLTISSL<br>EPEDFAVYYC<u>HQYGSISTT</u>FGQGTKVEIK |
| 5268 Vk | (1)<br>DIVLTQSPATLSLSPGERATLSCRASQSVLGNYLAWYQQKPGQAPRLLIYGASSRATGVPARFSGSGSGTDFTLTISSL<br>EPEDFAVYYCqQYshISLTFGQGTKVEIK |
| 5267 Vk | (1)<br>DIVLTQSPATLSLSPGERATLSCRASQSVLGNYLAWYQQKPGQAPRLLIYGASSRATGVPARFSGSGSGTDFTLTISSL<br>EPEDFAVYYCqQYshliITFGQGTKVEIK |
| 5269 Vk | (1)<br>DIVLTQSPATLSLSPGERATLSCRASQSVLGNYLAWYQQKPGQAPRLLIYGASSRATGVPARFSGSGSGTDFTLTISSL<br>EPEDFAVYYCqQfahIllTFGQGTKVEIK |
| MOR04190 Family | |
| | (SEQ ID NOS: 86-92)<br>1 |
| 127 | |
| 4190 Vh | (1)<br>QVQLVQSGAEVKKPGSSVKVSCKASGGTFS<u>SNYIS</u>WVRQAPGQGLEWMG<u>GIIPIFGHANYAQKFQG</u>RVTITADESTSTA<br>YMELSSLRSEDTAVYYCAR<u>SKKGMYGGWTYPLMMFDL</u>WGQGTLVTVSS |
| 5033 Vh | (1)<br>QVQLVQSGAEVKKPGSSVKVSCKASGGTFSSNYISWVRQAPGQGLEWMGiIIPpiGnAwYAQKFQGRVTITADESTSTA<br>YMELSSLRSEDTAVYYCARSKKGMYGGWTYPLMMFDLWGQGTLVTVSS |
| 5040 Vh | (1)<br>QVQLVQSGAEVKKPGSSVKVSCKASGGTFSSNYISWVRQAPGQGLEWMGispgtginAyYAQKFQGRVTITADESTSTA<br>YMELSSLRSEDTAVYYCARSKKGMYGGWTYPLMMFDLWGQGTLVTVSS |
| 5038 Vh | (1) QVQLVQSGAEVKKPGSSVKVSCKASGGTFSSNYISWVRQAPGQGLEWMG-<br>InahlGgtwYAQKFQGRVTITADESTSTAYMELSSLRSEDTAVYYCARSKKGMYGGWTYPLMMFDLWGQGTLVTVSS |
| 5034 Vh | (1)<br>QVQLVQSGAEVKKPGSSVKVSCKASGGTFSSNYISWVRQAPGQGLEWMGLIdPnFGgAyYAQKFQGRVTITADESTSTA<br>YMELSSLRSEDTAVYYCARSKKGMYGGWTYPLMMFDLWGQGTLVTVSS |
| 5036 Vh | (1)<br>QVQLVQSGAEVKKPGSSVKVSCKASGGTFSSNYISWVRQAPGQGLEWMGLIdPvFGgAyYAQKFQGRVTITADESTSTA<br>YMELSSLRSEDTAVYYCARSKKGMYGGWTYPLMMFDLWGQGTLVTVSS |
| 5037 Vh | (1)<br>QVQLVQSGAEVKKPGSSVKVSCKASGGTFSSNYISWVRQAPGQGLEWMglIdPmFGgAyYAQKFQGRVTITADESTSTA<br>YMELSSLRSEDTAVYYCARSKKGMYGGWTYPLMMFDLWGQGTLVTVSS |
| | (SEQ ID NOS: 93-98)<br>1 |
| 108 | |
| 4190 Vk | (1)<br>DIVLTQSPATLSLSPGERATLSC<u>RASQSVSSNYLA</u>WYQQKPGQAPRLLIY<u>YASRRAT</u>GVPARFSGSGSGTDFTLTISSL<br>EPEDFATYYC<u>QQTSNTPFT</u>FGQGTKVEIK |
| 4190$^{EV}$k | (1)<br>EIVLTQSPATLSLSPGERATLSCRASQSVSSNYLAWYQQKPGQAPRLLIYYASRRATGVPARFSGSGSGTDFTLTISSL<br>EPEDFAvYYCQQTSNTPFTFGQGTKVEIK |
| 5029 Vk | (1)<br>DIVLTQSPATLSLSPGERATLSCRASQSVSSNYLAWYQQKPGQAPRLLIYYASRRATGVPARFSGSGSGTDFTLTISSL<br>EPEDFAvYYCQQfitylpTFGQGTKVEIK |
| 5030 Vk | (1)<br>DIVLTQSPATLSLSPGERATLSCRASQSVSSNYLAWYQQKPGQAPRLLIYYASRRATGVPARFSGSGSGTDFTLTISSL<br>EPEDFAvYYCQQdalsPFTFGQGTKVEIK |
| 5031 Vk | (1)<br>DIVLTQSPATLSLSPGERATLSCRASQSVSSNYLAWYQQKPGQAPRLLIYYASRRATGVPARFSGSGSGTDFTLTISSL<br>EPEDFAvYYCQQdrgTPFTFGQGTKVEIK |
| 5032 Vk | (1)<br>DIVLTQSPATLSLSPGERATLSCRASQSVSSNYLAWYQQKPGQAPRLLIYYASRRATGVPARFSGSGSGTDFTLTISSL<br>EPEDFAvYYCQQslNiPFTFGQGTKVEIK |

TABLE 8-continued

Sequences of initial IL-23p19 mAbs and their matured and engineered derivatives.

MOR04205

| | | |
|---|---|---|
| 116 | | (SEQ ID NO: 99)<br>1 |
| 4205 Vh | (1) | QVQLVQSGAEVKKPGESLKISCKGSGYSFT<u>NYWIS</u>WVRQAPGKGLEWMG<u>WIRPGDSDTRYSPSFEG</u>QVTISADKSISTA<br>YLQWSSLKASDTAMYYCAR<u>HYYGMDY</u>WGQGTLVTVSS |
| 110 | | (SEQ ID NO: 100)<br>1 |
| 4205 Vl | (1) | DIVLTQPPSVSGAPGQRVTISC<u>SGSSSNIGSYYVN</u>WYQQLPGTAPKLLIY<u>GNTHRPS</u>GVPDRFSGSKSGTSASLAITGL<br>QSEDEADYYC<u>QTYASLGPGEV</u>FGGGTKLTVL |

MOR04217

| | | |
|---|---|---|
| 121 | | (SEQ ID NO: 101)<br>1 |
| 4217 Vh | (1) | QVQLVESGGGLVQPGGSLRLSCAASGFTFS<u>SYWIT</u>WVRQAPGKGLEW<u>VSYISSSGSSTYYADSVKG</u>RFTISRDNSKNTL<br>YLQMNSLRAEDTAVYYCAR<u>GTFWSFGNYFAN</u>WGQGTLVTVSS |
| 107 | | (SEQ ID NO: 102)<br>1 |
| 4217 Vk | (1) | DIVLTQSPATLSLSPGERATLSC<u>RASQSIFYNLA</u>WYQQKPGQAPRLLIY<u>GASNRAT</u>GVPARFSGSGSGTDFTLTISSLE<br>PEDFATYYC<u>QQYSSEPVT</u>FGQGTKVEIK |

MOR04649 Family

| | | |
|---|---|---|
| 117 | | (SEQ ID NOS: 103-112)<br>1 |
| 4649 Vh | (1) | QVQLVQSGAEVKKPGESLKISCKGSGYSFS<u>NYWIG</u>WVRQMPGKGLEWMG<u>IIDPSNSYTNYSPSFQG</u>QVTISADKSISTA<br>YLQWSSLKASDTAMYYCAR<u>WYYKPFDV</u>WGQGTLVTVSS |
| 4649d Vh | (1) | QVQLVQSGAEVKKPGESLKISCKGSGYSFSNYWIGWVRQMPGKGLEWMGIIDPSNSYTdYSPSFQGQVTISADKSISTA<br>YLQWSSLKASDTAMYYCARWYYKPFDVWGQGTLVTVSS |
| 4649r Vh | (1) | QVQLVQSGAEVKKPGESLKISCKGSGYSFSNYWIGWVRQMPGKGLEWMGIIDPSNSYTrYSPSFQGQVTISADKSISTA<br>YLQWSSLKASDTAMYYCARWYYKPFDVWGQGTLVTVSS |
| 4649r$^E$ Vh | (1) | eVQLVQSGAEVKKPGESLKISCKGSGYSFSNYWIGWVRQMPGKGLEWMGIIDPSNSYTrYSPSFQGQVTISADKSISTA<br>YLQWSSLKASDTAMYYCARWYYKPFDVWGQGTLVTVSS |
| 5046 Vh | (1) | QVQLVQSGAEVKKPGESLKISCKGSGYSFSNYWIGWVRQMPGKGLEWMGIIDPvsSwTkYSPSFQGQVTISADKSISTA<br>YLQWSSLKASDTAMYYCARWYYKPFDVWGQGTLVTVSS |
| 5044 Vh | (1) | QVQLVQSGAEVKKPGESLKISCKGSGYSFSNYWIGWVRQMPGKGLEWMGIIsPSgStTwYSPSFQGQVTISADKSISTA<br>YLQWSSLKASDTAMYYCARWYYKPFDVWGQGTLVTVSS |
| 5043 Vh | (1) | QVQLVQSGAEVKKPGESLKISCKGSGYSFSNYWIGWVRQMPGKGLEWMGfIsPdgShTwYSPSFQGQVTISADKSISTA<br>YLQWSSLKASDTAMYYCARWYYKPFDVWGQGTLVTVSS |
| 5041 Vh | (1) | QVQLVQSGAEVKKPGESLKISCKGSGYSFSNYWIGWVRQMPGKGLEWMGIIsPtgSvTwYSPSFQGQVTISADKSISTA<br>YLQWSSLKASDTAMYYCARWYYKPFDVWGQGTLVTVSS |
| 5042 Vh | (1) | QVQLVQSGAEVKKPGESLKISCKGSGYSFSNYWIGWVRQMPGKGLEWMGIIsPtgSsTwYSPSFQGQVTISADKSISTA<br>YLQWSSLKASDTAMYYCARWYYKPFDVWGQGTLVTVSS |
| 5045 Vh | (1) | QVQLVQSGAEVKKPGESLKISCKGSGYSFSNYWIGWVRQMPGKGLEWMGIIsPtgSaTwYSPSFQGQVTISADKSISTA<br>YLQWSSLKASDTAMYYCARWYYKPFDVWGQGTLVTVSS |

TABLE 8-continued

Sequences of initial IL-23p19 mAbs and their matured and engineered derivatives.

* Consensus N-linked glycosylation site in 4649 Vh (SEQ ID NOS: 113-116)
1
111

4649 VL (1)
DIVLTQPPSVSGAPGQRVTISCTGSSSNIGSGYDVHWYQQLPGTAPKLLIYGNSKRPSGVPDRFSGSKSGTSASLAITG
LQSEDEADYYCSSWT--PSSVVFGGGTKLTVL

5058 VL (1)
DIVLTQPPSVSGAPGQRVTISCTGSSSNIGSGYDVHWYQQLPGTAPKLLIYGNSKRPSGVPDRFSGSKSGTSASLAITG
LQSEDEADYYCSSWTdtPnmiVFGGGTKLTVL 5059 VL (1)
DIVLTQPPSVSGAPGQRVTISCTGSSSNIGSGYDVHWYQQLPGTAPKLLIYGNSKRPSGVPDRFSGSKSGTSASLAITG
LQSEDEADYYCaSWTdglSlVVFGGGTKLTVL 5059$^{QS}$VL (1)
qsVLTQPPSVSGAPGQRVTISCTGSSSNIGSGYDVHWYQQLPGTAPKLLIYGNSKRPSGVPDRFSGSKSGTSASLAITG
LQSEDEADYYCaSWTdglSlVVFGGGTKLTVL MOR04658 Family (SEQ ID NOS: 117-127)
1
123

4658 Vh (1) QVQLVESGGGLVQPGGSLRLSCAASGFTFSSFGMSWVRQAPGKGLEWVSNISSS--
GSSTYYADSVKGRFTISRDNSKNTLYLQMNSLRAEDTAVYYCARYWGTPYLMQFDNWGQGTLVTVSS

5048 Vh (1)
QVQLVESGGGLVQPGGSLRLSCAASGFTFSSFGMSWVRQAPGKGLEWVSNIehkfmGytTYYAagVKGRFTISRDNSKN
TLYLQMNSLRAEDTAVYYCARYWGTPYLMQFDNWGQGTLVTVSS 5050 Vh (1)
QVQLVESGGGLVQPGGSLRLSCAASGFTFSSFGMSWVRQAPGKGLEWVSsIehkytGytTYYAapVKGRFTISRDNSKN
TLYLQMNSLRAEDTAVYYCARYWGTPYLMQFDNWGQGTLVTVSS 5053 Vh (1)
QVQLVESGGGLVQPGGSLRLSCAASGFTFSSFGMSWVRQAPGKGLEWVSNIehkytsytTYYAaSVKGRFTISRDNSKN
TLYLQMNSLRAEDTAVYYCARYWGTPYLMQFDNWGQGTLVTVSS 5039 Vh (1)
QVQLVESGGGLVQPGGSLRLSCAASGFTFSSFGMSWVRQAPGKGLEWVSNIehkylnyaTYYAaSVKGRFTISRDNSKN
TLYLQMNSLRAEDTAVYYCARYWGTPYLMQFDNWGQGTLVTVSS 5055 Vh (1)
QVQLVESGGGLVQPGGSLRLSCAASGFTFSSFGMSWVRQAPGKGLEWVSNIehkylGyaTvYAaSVKGRFTISRDNSKN
TLYLQMNSLRAEDTAVYYCARYWGTPYLMQFDNWGQGTLVTVSS 5056 Vh (4)
QVQLVESGGGLVQPGGSLRLSCAASGFTFSSFGMSWVRQAPGKGLEWVSsIehkylsyaTYYAagVKGRFTISRDNSKN
TLYLQMNSLRAEDTAVYYCARYWGTPYLMQFDNWGQGTLVTVSS 5052 Vh (1)
QVQLVESGGGLVQPGGSLRLSCAASGFTFSSFGMSWVRQAPGKGLEWVSsIehkylsytTfYAaSVKGRFTISRDNSKN
TLYLQMNSLRAEDTAVYYCARYWGTPYLMQFDNWGQGTLVTVSS 5049 Vh (1)
QVQLVESGGGLVQPGGSLRLSCAASGFTFSSFGMSWVRQAPGKGLEWVSgIehkylsytThYAaSVKGRFTISRDNSKN
TLYLQMNSLRAEDTAVYYCARYWGTPYLMQFDNWGQGTLVTVSS 5051 Vh (1)
QVQLVESGGGLVQPGGSLRLSCAASGFTFSSFGMSWVRQAPGKGLEWVSqIehkylsytTlYAaSVKGRFTISRDNSKN
TLYLQMNSLRAEDTAVYYCARYWGTPYLMQFDNWGQGTLVTVSS 5054 Vh (1)
QVQLVESGGGLVQPGGSLRLSCAASGFTFSSFGMSWVRQAPGKGLEWVSgIehkylsyaTlYAaSVKGRFTISRDNSKN
TLYLQMNSLRAEDTAVYYCARYWGTPYLMQFDNWGQGTLVTVSS 5047 Vh (SEQ ID NO: 147)
(1)
QVQLVESGGGLVQPGGSLRLSCAASGFTFSSFGMSWVRQAPGKGLEWVSNIehkylGyaTsYAaSVKGRFTISRDNSKNTLYLQMNSL
RAEDTAVYYCARYWGTPYLMQFDNWGQGTLVTVSS (SEQ ID NOS: 128-132)
1

TABLE 8-continued

Sequences of initial IL-23p19 mAbs and their matured and engineered derivatives.

```
4658 VL   (1)
          DIALTQPASVSGSPGQSITISCTGTSSDVGGYNSVSWYQQHPGKAPKLMIYSVSSRPSGVSNRFSGSKSGNTASLTISG
          LQAEDEADYYCSSYDTNKPLVVFGGGTKLTVL

5061 VL   (1)
          DIALTQPASVSGSPGQSITISCTGTSSDVGGYNSVSWYQQHPGKAPKLMIYSVSSRPSGVSNRFSGSKSGNTASLTISG
          LQAEDEADYYCSSYyfylqriVFGGGTKLTVL 5062 VL   (1)
          DIALTQPASVSGSPGQSITISCTGTSSDVGGYNSVSWYQQHPGKAPKLMIYSVSSRPSGVSNRFSGSKSGNTASLTISG
          LQAEDEADYYCqtYyfsysgpVFGGGTKLTVL 5060 VL   (1)
          DIALTQPASVSGSPGQSITISCTGTSSDVGGYNSVSWYQQHPGKAPKLMIYSVSSRPSGVSNRFSGSKSGNTASLTISG
          LQAEDEADYYCgSYDvygrfyVFGGGTKLTVL 5063 VL   (1)
          DIALTQPASVSGSPGQSITISCTGTSSDVGGYNSVSWYQQHPGKAPKLMIYSVSSRPSGVSNRFSGSKSGNTASLTISG
          LQAEDEADYYCgSwDpifsyeVFGGGTKLTVL
```

TABLE 9

Nucledide Sequences

IL-23 p19 5040$^{Q/EV}$
VH-GCE (SEQ ID NO: 133):
(VH amino acid sequence is 5040 Vh)

```
      Q   V   Q   L   V   Q   S   G   A   E   V   K   K   P   G   S   S  •
  1 CAGGTGCAGC TGGTGCAGTC TGGGGCTGAG GTGAAGAAGC CTGGGTCCTC
    GTCCACGTCG ACCACGTCAG ACCCCGACTC CACTTCTTCG GACCCAGGAG

CDR1
                                                        ~~~~~~~~~~~
    •V   K   V   S   C   K   A   S   G   G   T   F   S   S   N   Y   I  •
 51 GGTGAAGGTC TCCTGCAAGG CTTCTGGAGG CACCTTCAGC AGCAACTACA
    CCACTTCCAG AGGACGTTCC GAAGACCTCC GTGGAAGTCG TCGTTGATGT

~~~~~                                                     ~~~
    •S   W   V   R   Q   A   P   G   Q   G   L   E   W   M   G   I  •
101 TCAGCTGGGT GCGACAGGCC CCTGGACAAG GGCTTGAGTG GATGGGGATC
    AGTCGACCCA CGCTGTCCGG GGACCTGTTC CCGAACTCAC CTACCCCTAG

CDR2
       ~~~~~~~~~~~~~~~~~~~~~~~~~~~~~~~~~~~~~~~~~~~~~~~~
       S   P   G   T   G   I   N   A   Y   Y   A   Q   K   F   Q   G   R  •
151 AGCCCTGGCA CCGGTATCAA CGCATACTAC GCACAGAAGT TCCAGGGCAG
    TCGGGACCGT GGCCATAGTT GCGTATGATG CGTGTCTTCA AGGTCCCGTC

•V   T   I   T   A   D   E   S   T   S   T   A   Y   M   E   L   S  •
201 AGTCACGATT ACCGCGGACG AATCCACGAG CACAGCCTAC ATGGAGCTGA
    TCAGTGCTAA TGGCGCCTGC TTAGGTGCTC GTGTCGGATG TACCTCGACT

CDR3
                                                        ~~~~~~
    •S   L   R   S   E   D   T   A   V   Y   Y   C   A   R   S   K
251 GCAGCCTGAG ATCTGAGGAC ACGGCCGTGT ATTACTGTGC GAGAAGCAAG
    CGTCGGACTC TAGACTCCTG TGCCGGCACA TAATGACACG CTCTTCGTTC

CDR3
       ~~~~~~~~~~~~~~~~~~~~~~~~~~~~~~~~~~~~~~~~~~~~~~~~
       K   G   M   Y   G   G   W   T   Y   P   L   M   M   F   D   L   W  •
301 AAGGGCATGT ACGGCGGCTG GACCTACCCC CTGATGATGT TCGACCTGTG
    TTCCCGTACA TGCCGCCGAC CTGGATGGGG GACTACTACA AGCTGGACAC

•G   Q   G   T   L   V   T   V   S   S
351 GGGCCAGGGC ACCCTGGTGA CCGTGAGCAG C
    CCCGGTCCCG TGGGACCACT GGCACTCGTC G
```

TABLE 9-continued

Nucledide Sequences

IL-23 p19 5040^{Q/EV}
VH-HCO (SEQ ID NO: 134):
(VH amino acid sequence is 5040 Vh)

```
     Q   V   Q   L   V   Q   S   G   A   E   V   K   K   P   G   S   S •
  1 CAGGTGCAGC TGGTGCAGAG CGGCGCCGAG GTGAAGAAGC CCGGCAGCAG
    GTCCACGTCG ACCACGTCTC GCCGCGGCTC CACTTCTTCG GGCCGTCGTC

CDR1
                                                          ~~~~~~~~~~~
   • V   K   V   S   C   K   A   S   G   G   T   F   S   S   N   Y   I •
 51 CGTGAAGGTG AGCTGCAAGG CCAGCGGCGG CACCTTCAGC AGCAACTACA
    GCACTTCCAC TCGACGTTCC GGTCGCCGCC GTGGAAGTCG TCGTTGATGT

~~~~~                                                        ~~~
   •   S   W   V   R   Q   A   P   G   Q   G   L   E   W   M   G   I •
101 TCAGCTGGGT GCGCCAGGCC CCCGGCCAGG GCCTGGAGTG GATGGGCATC
    AGTCGACCCA CGCGGTCCGG GGGCCGGTCC CGGACCTCAC CTACCCGTAG

CDR2
    ~~~~~~~~~~~~~~~~~~~~~~~~~~~~~~~~~~~~~~~~~~~~~~~~~~~~
     S   P   G   T   G   I   N   A   Y   Y   A   Q   K   F   Q   G   R •
151 AGCCCCGGCA CCGGCATCAA CGCCTACTAC GCCCAGAAGT TCCAGGGCCG
    TCGGGGCCGT GGCCGTAGTT GCGGATGATG CGGGTCTTCA AGGTCCCGGC

• V   T   I   T   A   D   E   S   T   S   T   A   Y   M   E   L   S •
201 CGTGACCATC ACCGCCGACG AGAGCACCAG CACCGCCTAC ATGGAGCTGA
    GCACTGGTAG TGGCGGCTGC TCTCGTGGTC GTGGCGGATG TACCTCGACT

~~~~~~
   •   S   L   R   S   E   D   T   A   V   Y   Y   C   A   R   S   K
251 GCAGCCTGCG CAGCGAGGAC ACCGCCGTGT ACTACTGCGC CCGCAGCAAG
    CGTCGGACGC GTCGCTCCTG TGGCGGCACA TGATGACGCG GGCGTCGTTC

CDR3
    ~~~~~~~~~~~~~~~~~~~~~~~~~~~~~~~~~~~~~~~~~~~~~~~~~~~~
     K   G   M   Y   G   G   W   T   Y   P   L   M   M   F   D   L   W •
301 AAGGGCATGT ACGGCGGCTG GACCTACCCC CTGATGATGT TCGACCTGTG
    TTCCCGTACA TGCCGCCGAC CTGGATGGGG GACTACTACA AGCTGGACAC

• G   Q   G   T   L   V   T   V   S   S
351 GGGCCAGGGC ACCCTGGTGA CCGTGAGCAG C
    CCCGGTCCCG TGGGACCACT GGCACTCGTC G
```

IL-23 p19 5040^{Q/EV}
VH-MOR (SEQ ID NO: 135):
(VH amino acid sequence is 5040 Vh)

```
     Q   V   Q   L   V   Q   S   G   A   E   V   K   K   P   G   S   S •
  1 CAGGTGCAAT TGGTTCAGTC TGGCGCGGAA GTGAAAAAAC CGGGCAGCAG
    GTCCACGTTA ACCAAGTCAG ACCGCGCCTT CACTTTTTTG GCCCGTCGTC

CDR1
                                                          ~~~~~~~~~~~
   • V   K   V   S   C   K   A   S   G   G   T   F   S   S   N   Y   I •
 51 CGTGAAAGTG AGCTGCAAAG CCTCCGGAGG CACTTTTTCT TCTAATTATA
    GCACTTTCAC TCGACGTTTC GGAGGCCTCC GTGAAAAAGA AGATTAATAT

~~~~~                                                        ~~~
   •   S   W   V   R   Q   A   P   G   Q   G   L   E   W   M   G   I •
101 TTTCTTGGGT GCGCCAAGCC CCTGGGCAGG GTCTCGAGTG GATGGGCATT
    AAAGAACCCA CGCGGTTCGG GGACCCGTCC CAGAGCTCAC CTACCCGTAA

CDR2
    ~~~~~~~~~~~~~~~~~~~~~~~~~~~~~~~~~~~~~~~~~~~~~~~~~~~~
     S   P   G   T   G   I   N   A   Y   Y   A   Q   K   F   Q   G   R •
151 TCTCCTGGTA CTGGTATTAA TGCTTATTAT GCTCAGAAGT TTCAGGGTCG
    AGAGGACCAT GACCATAATT ACGAATAATA CGAGTCTTCA AAGTCCCAGC

• V   T   I   T   A   D   E   S   T   S   T   A   Y   M   E   L   S •
201 GGTGACCATT ACCGCGGATG AAAGCACCAG CACCGCGTAT ATGGAACTGA
    CCACTGGTAA TGGCGCCTAC TTTCGTGGTC GTGGCGCATA TACCTTGACT

~~~~~~
   •   S   L   R   S   E   D   T   A   V   Y   Y   C   A   R   S   K
251 GCAGCCTGCG TAGCGAAGAT ACGGCCGTGT ATTATTGCGC GCGTTCTAAG
    CGTCGGACGC ATCGCTTCTA TGCCGGCACA TAATAACGCG CGCAAGATTC
```

TABLE 9-continued

Nucledide Sequences

```
                    CDR3
        ~~~~~~~~~~~~~~~~~~~~~~~~~~~~~~~~~~~~~~~~~~~~~~~~~~~~~~~~
      K  G  M  Y     G  G  W     T  Y  P     L  M  M     F  D  L  W •
  301 AAGGGTATGT ATGGTGGTTG GACTTATCCT CTTATGATGT TTGATCTTTG
      TTCCCATACA TACCACCAAC CTGAATAGGA GAATACTACA AACTAGAAAC

• G  Q  G     T  L  V  T     V  S  S
  351 GGGCCAAGGC ACCCTGGTGA CGGTTAGCTC A
      CCCGGTTCCG TGGGACCACT GCCAATCGAG T

IL-23 p19 5040^{Q/EV}
  VK-HCO (SEQ ID NO: 136):
  (VK amino acid sequence is 4190^{EV})

E  I  V  L     T  Q  S     P  A  T     L  S  L  S     P  G  E •
    1 GAGATCGTGC TGACCCAGAG CCCCGCCACC CTGAGCCTGA GCCCCGGCGA
      CTCTAGCACG ACTGGGTCTC GGGGCGGTGG GACTCGGACT CGGGGCCGCT

CDR1
                  ~~~~~~~~~~~~~~~~~~~~~~~~~~~~~~~~~~~~~
     • R  A  T     L  S  C  R     A  S  Q     S  V  S     S  N  Y  L •
   51 GCGCGCCACC CTGAGCTGCC GCGCCAGCCA GAGCGTGAGC AGCAACTACC
      CGCGCGGTGG GACTCGACGG CGCGGTCGGT CTCGCACTCG TCGTTGATGG

~~~~~
     • A  W  Y     Q  Q  K     P  G  Q  A     P  R  L     L  I  Y
  101 TGGCCTGGTA CCAGCAGAAG CCCGGCCAGG CCCCCCGCCT GCTGATCTAC
      ACCGGACCAT GGTCGTCTTC GGGCCGGTCC GGGGGGCGGA CGACTAGATG

CDR2
     ~~~~~~~~~~~~~~~~~~~~~~~~
      Y  A  S  R     R  A  T     G  V  P     A  R  F  S     G  S  G •
  151 TACGCCAGCC GCCGCGCCAC CGGCGTGCCC GCCCGCTTCA GCGGCAGCGG
      ATGCGGTCGG CGGCGCGGTG GCCGCACGGG CGGGCGAAGT CGCCGTCGCC

• S  G  T     D  F  T  L     T  I  S     S  L  E     P  E  D  F •
  201 CAGCGGCACC GACTTCACCC TGACCATCAG CAGCCTGGAG CCCGAGGACT
      GTCGCCGTGG CTGAAGTGGG ACTGGTAGTC GTCGGACCTC GGGCTCCTGA

CDR3
        ~~~~~~~~~~~~~~~~~~~~~~~~~~~~~~~~
     • A  V  Y     Y  C  Q     Q  T  S  N     T  P  F     T  F  G •
  251 TCGCCGTGTA CTACTGCCAG CAGACCAGCA ACACCCCCTT CACCTTCGGC
      AGCGGCACAT GATGACGGTC GTCTGGTCGT TGTGGGGGAA GTGGAAGCCG

Q  G  T  K     V  E  I     K
  301 CAGGGCACCA AGGTGGAGAT CAAG
      GTCCCGTGGT TCCACCTCTA GTTC

IL-23 p19 5040^{Q/EV}
  VK-HCO (SEQ ID NO: 137):
  (VK amino acid sequence is 4190^{EV})

E  I  V  L     T  Q  S     P  A  T     L  S  L  S     P  G  E •
    1 GAAATTGTGT TGACACAGTC TCCAGCCACC CTGTCTTTGT CTCCAGGGGA
      CTTTAACACA ACTGTGTCAG AGGTCGGTGG GACAGAAACA GAGGTCCCCT

CDR1
                  ~~~~~~~~~~~~~~~~~~~~~~~~~~~~~~~~~~~~~
     • R  A  T     L  S  C  R     A  S  Q     S  V  S     S  N  Y  L •
   51 AAGAGCCACC CTCTCCTGCA GGGCCAGTCA GAGTGTTAGC AGCAACTACT
      TTCTCGGTGG GAGAGGACGT CCCGGTCAGT CTCACAATCG TCGTTGATGA

~~~~~
     • A  W  Y     Q  Q  K     P  G  Q  A     P  R  L     L  I  Y
  101 TAGCCTGGTA CCAACAGAAA CCTGGCCAGG CTCCCAGGCT CCTCATCTAT
      ATCGGACCAT GGTTGTCTTT GGACCGGTCC GAGGGTCCGA GGAGTAGATA

CDR2
     ~~~~~~~~~~~~~~~~~~~~~~~~
      Y  A  S  R     R  A  T     G  V  P     A  R  F  S     G  S  G •
  151 TACGCATCCC GCAGGGCCAC TGGCGTGCCA GCCAGGTTCA GTGGCAGTGG
      ATGCGTAGGG CGTCCCGGTG ACCGCACGGT CGGTCCAAGT CACCGTCACC

• S  G  T     D  F  T  L     T  I  S     S  L  E     P  E  D  F •
  201 GTCTGGGACA GACTTCACTC TCACCATCAG CAGCCTAGAG CCTGAAGATT
      CAGACCCTGT CTGAAGTGAG AGTGGTAGTC GTCGGATCTC GGACTTCTAA
```

TABLE 9-continued

Nucledide Sequences

```
                          CDR3
              ~~~~~~~~~~~~~~~~~~~~~~~~~~~~~~
     • A  V  Y  Y  C  Q   Q  T  S  N   T  P  F   T  F  G
251 TTGCAGTTTA TTACTGTCAG CAGACTTCTA ATATCCTTTT TACCTTTGGC
    AACGTCAAAT AATGACAGTC GTCTGAAGAT TATGAGGAAA ATGGAAACCG

Q  G  T  K  V  E  I   K
301 CAGGGTACGA AAGTTGAAAT TAAA
    GTCCCATGCT TTCAACTTTA ATTT
```

IL-23 p19 5040$^{Q/EV}$
VK-HCO (SEQ ID NO: 138):
(VK amino acid sequence is 4190$^{EV}$)

```
     E  I  V  L   T  Q  S   P  A  T   L  S  L  S   P  G  E •
  1 GAGATCGTGC TGACCCAGAG CCCGGCGACC CTGAGCCTGT CTCCGGGCGA
    CTCTAGCACG ACTGGGTCTC GGGCCGCTGG GACTCGGACA GAGGCCCGCT

CDR1
                       ~~~~~~~~~~~~~~~~~~~~~~~~~~~~~~~~~~
    • R  A  T   L  S  C  R   A  S  Q   S  V  S   S  N  Y  L •
 51 ACGTGCGACC CTGAGCTGCA GAGCGAGCCA GTCTGTTTCT TCTAATTATC
    TGCACGCTGG GACTCGACGT CTCGCTCGGT CAGACAAAGA AGATTAATAG

~~~~~
    • A  W  Y  Q  Q  K   P  G  Q  A   P  R  L   L  I  Y
101 TGGCTTGGTA CCAGCAGAAA CCAGGTCAAG CACCGCGTCT ATTAATTTAT
    ACCGAACCAT GGTCGTCTTT GGTCCAGTTC GTGGCGCAGA TAATTAAATA

CDR2
    ~~~~~~~~~~~~~~~~~~~~~~~~
     Y  A  S  R   R  A  T   G  V  P   A  R  F  S   G  S  G •
151 TATGCTTCTC GTCGTGCAAC TGGGGTCCCG GCGCGTTTTA GCGGCTCTGG
    ATACGAAGAG CAGCACGTTG ACCCCAGGGC CGCGCAAAAT CGCCGAGACC

• S  G  T   D  F  T  L   T  I  S   S  L  E   P  E  D  F •
201 ATCCGGCACG GATTTTACCC TGACCATTAG CAGCCTGGAA CCTGAAGACT
    TAGGCCGTGC CTAAAATGGG ACTGGTAATC GTCGGACCTT GGACTTCTGA

CDR3
             ~~~~~~~~~~~~~~~~~~~~~~~~~~~~~~
    • A  V  Y  Y  C  Q   Q  T  S  N   T  P  F   T  F  G
251 TTGCGGTGTA TTATTGCCAG CAGACTTCTA ATATCCTTTT TACCTTTGGC
    AACGCCACAT AATAACGGTC GTCTGAAGAT TATGAGGAAA ATGGAAACCG

Q  G  T  K  V  E  I   K
301 CAGGGTACGA AAGTTGAAAT TAAA
    GTCCCATGCT TTCAACTTTA ATTT
```

IL-23 p19 3759$^{EQ/QS}$
VH-GCE (SEQ ID NO: 139):
(VH amino acid sequence is 4649r$^E$)

```
     E  V  Q  L   V  Q  S   G  A  E   V  K  K  P   G  E  S •
  1 GAGGTGCAGC TGGTGCAGTC TGGAGCAGAG GTGAAAAAGC CCGGGGAGTC
    CTCCACGTCG ACCACGTCAG ACCTCGTCTC CACTTTTTCG GGCCCCTCAG

CDR1
                                     ~~~~~~~~~~~~
    • L  K  I   S  C  K  G   S  G  Y   S  F  S   N  Y  W  I •
 51 TCTGAAGATC TCCTGTAAGG GTTCTGGATA CAGCTTTAGC AACTACTGGA
    AGACTTCTAG AGGACATTCC CAAGACCTAT GTCGAAATCG TTGATGACCT

~~~~~                                          ~~~
    • G  W  V   R  Q  M   P  G  K  G   L  E  W   M  G  I
101 TCGGCTGGGT GCGCCAGATG CCCGGGAAAG GCCTGGAGTG GATGGGGATC
    AGCCGACCCA CGCGGTCTAC GGGCCCTTTC CGGACCTCAC CTACCCCTAG

CDR2
    ~~~~~~~~~~~~~~~~~~~~~~~~~~~~~~~~~~~~~~~~~~~~~~~
     I  D  P  S   N  S  Y   T  R  Y   S  P  S  F   Q  G  Q •
151 ATCGACCCTA GCAACTCTTA CACCAGATAC AGCCCGTCCT TCCAAGGCCA
    TAGCTGGGAT CGTTGAGAAT GTGGTCTATG TCGGGCAGGA AGGTTCCGGT

• V  T  I   S  A  D  K   S  I  S   T  A  Y   L  Q  W  S •
201 GGTCACCATC TCAGCCGACA AGTCCATCAG CACCGCCTAC CTGCAGTGGA
    CCAGTGGTAG AGTCGGCTGT TCAGGTAGTC GTGGCGGATG GACGTCACCT
```

TABLE 9-continued

Nucleotide Sequences

```
                                                ~~~~~~
     • S   L   K   A   S   D   T   A   M   Y   Y   C   A   R   W   Y
251 GCAGCCTGAA GGCCTCGGAC ACCGCCATGT ATTACTGTGC GAGATGGTAC
    CGTCGGACTT CCGGAGCCTG TGGCGGTACA TAATGACACG CTCTACCATG

CDR3
    ~~~~~~~~~~~~~~~~~~~~
     Y   K   P   F   D   V   W   G   Q   G   T   L   V   T   V   S   S •
301 TACAAGCCCT TCGACGTGTG GGGCCAGGGC ACCCTGGTGA CCGTGAGCAG
    ATGTTCGGGA AGCTGCACAC CCCGGTCCCG TGGGACCACT GGCACTCGTC

• S
351 C
    G
```

IL-23 p19 3759$^{EQ/QS}$
VH-HCO (SEQ ID NO: 140):
(VH amino acid sequence is 4649r$^E$)

```
     E   V   Q   L   V   Q   S   G   A   E   V   K   K   P   G   E   S •
  1 GAGGTGCAGC TGGTGCAGAG CGGCGCCGAG GTGAAGAAGC CCGGCGAGAG
    CTCCACGTCG ACCACGTCTC GCCGCGGCTC CACTTCTTCG GGCCGCTCTC

CDR1
                                                  ~~~~~~~~~~~
     • L   K   I   S   C   K   G   S   G   Y   S   F   S   N   Y   W   I •
 51 CCTGAAGATC AGCTGCAAGG GCAGCGGCTA CAGCTTCAGC AACTACTGGA
    GGACTTCTAG TCGACGTTCC CGTCGCCGAT GTCGAAGTCG TTGATGACCT

~~~~~                                                ~~~
     • G   W   V   R   Q   M   P   G   K   G   L   E   W   M   G   I
101 TCGGCTGGGT GCGCCAGATG CCCGGCAAGG GCCTGGAGTG GATGGGCATC
    AGCCGACCCA CGCGGTCTAC GGGCCGTTCC CGGACCTCAC CTACCCGTAG

CDR2
    ~~~~~~~~~~~~~~~~~~~~~~~~~~~~~~~~~~~~~~~~~~~~~~~~~~~~~
     I   D   P   S   N   S   Y   T   R   Y   S   P   S   F   Q   G   Q •
151 ATCGACCCCA GCAACAGCTA CACCCGCTAC AGCCCCAGCT TCCAGGGCCA
    TAGCTGGGGT CGTTGTCGAT GTGGGCGATG TCGGGGTCGA AGGTCCCGGT

• V   T   I   S   A   D   K   S   I   S   T   A   Y   L   Q   W   S •
201 GGTGACCATC AGCGCCGACA AGAGCATCAG CACCGCCTAC CTGCAGTGGA
    CCACTGGTAG TCGCGGCTGT TCTCGTAGTC GTGGCGGATG GACGTCACCT

~~~~~~
     • S   L   K   A   S   D   T   A   M   Y   Y   C   A   R   W   Y
251 GCAGCCTGAA GGCCAGCGAC ACCGCCATGT ACTACTGCGC CCGCTGGTAC
    CGTCGGACTT CCGGTCGCTG TGGCGGTACA TGATGACGCG GGCGACCATG

CDR3
    ~~~~~~~~~~~~~~~~~~~~
     Y   K   P   F   D   V   W   G   Q   G   T   L   V   T   V   S   S •
301 TACAAGCCCT TCGACGTGTG GGGCCAGGGC ACCCTGGTGA CCGTGAGCAG
    ATGTTCGGGA AGCTGCACAC CCCGGTCCCG TGGGACCACT GGCACTCGTC

• S
351 C
    G
```

IL-23 p19 3759$^{EQ/QS}$
VH-MOR (SEQ ID NO: 141):
(VH amino acid sequence is 4649r$^E$)

```
     E   V   Q   L   V   Q   S   G   A   E   V   K   K   P   G   E   S •
  1 GAGGTGCAAT TGGTTCAGAG CGGCGCGGAA GTGAAAAAAC CGGGCGAAAG
    CTCCACGTTA ACCAAGTCTC GCCGCGCCTT CACTTTTTTG GCCCGCTTTC

CDR1
                                                  ~~~~~~~~~~~
     • L   K   I   S   C   K   G   S   G   Y   S   F   S   N   Y   W   I •
 51 CCTGAAAATT AGCTGCAAAG GTTCCGGATA TTCCTTTTCT AATTATTGGA
    GGACTTTTAA TCGACGTTTC CAAGGCCTAT AAGGAAAAGA TTAATAACCT

~~~~~                                                ~~~
     • G   W   V   R   Q   M   P   G   K   G   L   E   W   M   G   I
101 TTGGTTGGGT GCGCCAGATG CCTGGGAAGG GTCTCGAGTG GATGGGCATT
    AACCAACCCA CGCGGTCTAC GGACCCTTCC CAGAGCTCAC CTACCCGTAA
```

TABLE 9-continued

Nucleotide Sequences

```
                    CDR2
         ~~~~~~~~~~~~~~~~~~~~~~~~~~~
      I   D   P   S   N   S   Y   T   R   Y   S   P   S   F   Q   G   Q  •
151 ATCGATCCGT CTAATAGCTA TACCCGCTAT TCTCCGAGCT TTCAGGGCCA
    TAGCTAGGCA GATTATCGAT ATGGGCGATA AGAGGCTCGA AAGTCCCGGT

•  V   T   I   S   A   D   K   S   I   S   T   A   Y   L   Q   W   S •
201 GGTGACCATT AGCGCGGATA AAAGCATTAG CACCGCGTAT CTTCAATGGA
    CCACTGGTAA TCGCGCCTAT TTTCGTAATC GTGGCGCATA GAAGTTACCT

~~~~~~
    •  S   L   K   A   S   D   T   A   M   Y   Y   C   A   R   W   Y
251 GCAGCCTGAA AGCGAGCGAT ACGGCCATGT ATTATTGCGC GCGTTGGTAT
    CGTCGGACTT TCGCTCGCTA TGCCGGTACA TAATAACGCG CGCAACCATA

CDR3
         ~~~~~~~~~~~~~~~~~~~~
      Y   K   P   F   D   V   W   G   Q   G   T   L   V   T   V   S   S  •
301 TATAAGCCTT TTGATGTTTG GGGCCAAGGC ACCCTGGTGA CGGTTAGCTC
    ATATTCGGAA AACTACAAAC CCCGGTTCCG TGGGACCACT GCCAATCGAG

•  S
351 A
    T
```

IL-23 p19 3759$^{EQ/QS}$
VL-GCE (SEQ ID NO: 142):
(VL amino acid sequence is 5059$^{QS}$)

```
      Q   S   V   L   T   Q   P   P   S   V   S   G   A   P   G   Q   R  •
  1 CAGTCTGTGC TGACGCAGCC GCCCTCAGTG TCTGGGGCCC AGGGCAGAG
    GTCAGACACG ACTGCGTCGG CGGGAGTCAC AGACCCCGGG GTCCCGTCTC

CDR1
                    ~~~~~~~~~~~~~~~~~~~~~~~~~~~~~~~~~~~~~~
    •  V   T   I   S   C   T   G   S   S   S   N   I   G   S   G   Y   D •
 51 GGTCACCATC TCCTGCACTG GGAGCAGCTC CAACATCGGG AGCGGTTATG
    CCAGTGGTAG AGGACGTGAC CCTCGTCGAG GTTGTAGCCC TCGCCAATAC

~~~~~~~~
    •  V   H   W   Y   Q   Q   L   P   G   T   A   P   K   L   L   I
101 ATGTACACTG GTACCAGCAG CTTCCAGGAA CAGCCCCCAA ACTCCTCATC
    TACATGTGAC CATGGTCGTC GAAGGTCCTT GTCGGGGGTT TGAGGAGTAG

CDR2
         ~~~~~~~~~~~~~~~~~~~~~~~
      Y   G   N   S   K   R   P   S   G   V   P   D   R   F   S   G   S  •
151 TATGGTAACA GCAAGCGGCC CTCAGGGGTC CCTGACCGAT TCTCTGGCTC
    ATACCATTGT CGTTCGCCGG GAGTCCCCAG GGACTGGCTA AGAGACCGAG

•  K   S   G   T   S   A   S   L   A   I   T   G   L   Q   S   E   D •
201 CAAGTCTGGC ACCTCAGCCT CCCTGGCCAT CACTGGGCTC CAGAGCGAGG
    GTTCAGACCG TGGAGTCGGA GGGACCGGTA GTGACCCGAG GTCTCGCTCC

CDR3
                           ~~~~~~~~~~~~~~~~~~~~~~~~~~~~~~~~~~
    •  E   A   D   Y   Y   C   A   S   W   T   D   G   L   S   L   V
251 ATGAGGCTGA TTATTACTGC GCCAGCTGGA CCGACGGCCT GAGCCTGGTG
    TACTCCGACT AATAATGACG CGGTCGACCT GGCTGCCGGA CTCGGACCAC

~~~
      V   F   G   G   G   T   K   L   T   V   L   G
301 GTGTTCGGCG GCGGCACCAA GCTGACCGTG CTGGGC
    CACAAGCCGC CGCCGTGGTT CGACTGGCAC GACCCG
```

IL-23 p19 3759$^{EQ/QS}$
VL-HCO (SEQ ID NO: 143):
(VL amino acid sequence is 5059$^{QS}$)

```
      Q   S   V   L   T   Q   P   P   S   V   S   G   A   P   G   Q   R  •
  1 CAGAGCGTGC TGACCCAGCC CCCCAGCGTG AGCGGCGCCC CCGGCCAGCG
    GTCTCGCACG ACTGGGTCGG GGGGTCGCAC TCGCCGCGGG GGCCGGTCGC

CDR1
                    ~~~~~~~~~~~~~~~~~~~~~~~~~~~~~~~~~~~~~~~~~
    •  V   T   I   S   C   T   G   S   S   S   N   I   G   S   G   Y   D •
 51 CGTGACCATC AGCTGCACCG GCAGCAGCAG CAACATCGGC AGCGGCTACG
```

TABLE 9-continued

Nucledide Sequences

```
                GCACTGGTAG TCGACGTGGC CGTCGTCGTC GTTGTAGCCG TCGCCGATGC

~~~~~~~~
     • V   H   W     Y   Q   Q     L   P   G   T     A   P   K     L   L   I
101 ACGTGCACTG GTACCAGCAG CTGCCCGGCA CCGCCCCCAA GCTGCTGATC
    TGCACGTGAC CATGGTCGTC GACGGGCCGT GGCGGGGGTT CGACGACTAG

CDR2
         ~~~~~~~~~~~~~~~~~~~~~~~~
     Y   G   N   S     K   R   P     S   G   V     P   D   R   F     S   G   S •
151 TACGGCAACA GCAAGCGCCC CAGCGGCGTG CCCGACCGCT TCAGCGGCAG
    ATGCCGTTGT CGTTCGCGGG GTCGCCGCAC GGGCTGGCGA AGTCGCCGTC

• K   S   G     T   S   A   S     L   A   I     T   G   L     Q   S   E   D •
201 CAAGAGCGGC ACCAGCGCCA GCCTGGCCAT CACCGGCCTC CAGAGCGAGG
    GTTCTCGCCG TGGTCGCGGT CGGACCGGTA GTGGCCGGAG GTCTCGCTCC

CDR3
                              ~~~~~~~~~~~~~~~~~~~~~~~~~~~~~~~~
     • E   A   D     Y   Y   C     A   S   W   T     D   G   L     S   L   V
251 ACGAGGCCGA CTACTACTGT GCCAGCTGGA CCGACGGCCT GAGCCTGGTG
    TGCTCCGGCT GATGATGACA CGGTCGACCT GGCTGCCGGA CTCGGACCAC

~~~
     V   F   G   G     G   T   K     L   T   V     L   G
301 GTGTTCGGCG GCGGCACCAA GCTGACCGTG CTGGGC
    CACAAGCCGC CGCCGTGGTT CGACTGGCAC GACCCG
```

IL-23 p19 3759$^{EQ/QS}$
VL-MOR (SEQ ID NO: 144):
(VL amino acid sequence is 5059$^{QS}$)

```
       Q   S   V   L     T   Q   P     P   S   V     S   G   A   P     G   Q   R •
     1 CAGAGCGTGC TGACCCAGCC GCCTTCAGTG AGTGGCGCAC CAGGTCAGCG
       GTCTCGCACG ACTGGGTCGG CGGAAGTCAC TCACCGCGTG GTCCAGTCGC

CDR1
                              ~~~~~~~~~~~~~~~~~~~~~~~~~~~~~~~~~~~~~~
     • V   T   I     S   C   T   G     S   S   S     N   I   G     S   G   Y   D •
    51 TGTGACCATC TCGTGTACGG GCAGCAGCAG CAACATTGGT TCTGGTTATG
       ACACTGGTAG AGCACATGCC CGTCGTCGTC GTTGTAACCA AGACCAATAC

~~~~~~~~
     • V   H   W     Y   Q   Q     L   P   G   T     A   P   K     L   L   I
101 ATGTGCATTG GTACCAGCAG TTGCCCGGGA CGGCGCCGAA ACTTCTGATT
    TACACGTAAC CATGGTCGTC AACGGGCCCT GCCGCGGCTT TGAAGACTAA

CDR2
         ~~~~~~~~~~~~~~~~~~~~~~~~
     Y   G   N   S     K   R   P     S   G   V     P   D   R   F     S   G   S •
151 TATGGTAATT CTAAGCGTCC CTCAGGCGTG CCGGATCGTT TTAGCGGATC
    ATACCATTAA GATTCGCAGG GAGTCCGCAC GGCCTAGCAA AATCGCCTAG

• K   S   G     T   S   A   S     L   A   I     T   G   L     Q   S   E   D •
201 CAAAAGCGGC ACCAGCGCGA GCCTTGCGAT TACGGGCCTG CAAAGCGAAG
    GTTTTCGCCG TGGTCGCGCT CGGAACGCTA ATGCCCGGAC GTTTCGCTTC

CDR3
                              ~~~~~~~~~~~~~~~~~~~~~~~~~~~~~~~~
     • E   A   D     Y   Y   C     A   S   W   T     D   G   L     S   L   V
251 ACGAAGCGGA TTATTATTGC GCTTCTTGGA CTGATGGTCT TTCTCTTGTT
    TGCTTCGCCT AATAATAACG CGAAGAACCT GACTACCAGA AAGAGAACAA

~~~
     V   F   G   G     G   T   K     L   T   V     L   G
301 GTGTTTGGCG GCGGCACGAA GTTAACCGTT CTTGGC
    CACAAACCGC CGCCGTGCTT CAATTGGCAA GAACCG
```

TABLE 10

SEQ ID NO: 145 (human IL-23p19 subunit)

Met Leu Gly Ser Arg Ala Val Met Leu Leu Leu Leu Pro Trp Thr
1               5                   10                  15

TABLE 10-continued

SEQ ID NO: 145 (human IL-23p19 subunit)

Ala Gln Gly Arg Ala Val Pro Gly Gly Ser Ser Pro Ala Trp Thr Gln
             20                  25                  30

Cys Gln Gln Leu Ser Gln Lys Leu Cys Thr Leu Ala Trp Ser Ala His
         35                  40                  45

Pro Leu Val Gly His Met Asp Leu Arg Glu Glu Gly Asp Glu Glu Thr
     50                  55                  60

Thr Asn Asp Val Pro His Ile Gln Cys Gly Asp Gly Cys Asp Pro Gln
 65                  70                  75                  80

Gly Leu Arg Asp Asn Ser Gln Phe Cys Leu Gln Arg Ile His Gln Gly
                 85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Ala Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185

---

What is claimed is:

1. An isolated IL-23p19 antibody, comprising a light chain variable region and a heavy chain variable region, said light chain variable region comprising:
   a complementarity determining region light chain 1 (CDRL1) amino acid sequence of SEQ ID NO:50;
   a CDRL2 amino acid sequence of SEQ ID NO:56; and
   a CDRL3 amino acid sequence of SEQ ID NO:73,
   said heavy chain variable region comprising:
   a complementarity determining region heavy chain 1 (CDRH1) amino acid sequence of SEQ ID NO:5;
   a CDRH2 amino acid sequence of SEQ ID NO:28; and a CDRH3 amino acid sequence of SEQ ID NO:44.

2. The isolated IL-23p19 antibody of claim 1, further comprising at least one human framework region adjacent to a complementarity determining region.

3. The IL-23p19 antibody of claim 1, wherein said antibody binds IL-23p19 with at least one affinity selected from at least $10^{-9}$ M, at least $10^{-10}$ M, at least $10^{-11}$ M, and at least $10^{-12}$ M, at least $10^{-13}$ M, at least $10^{-14}$ M, and at least $10^{-15}$ M, as determined by surface plasmon resonance or the Kinexa method.

4. The IL-23p19 antibody of claim 1, wherein said antibody substantially modulates an activity of the IL-23 polypeptide, the activity selected from the group consisting of binding to the IL-23 receptor (IL-23R), induction of STAT3 phosphorylation, and IL-17 production.

5. A composition comprising the isolated IL-23p19 antibody according to claim 1 and at least one pharmaceutically acceptable carrier or diluent.

6. The composition according to claim 5, further comprising at least one compound or polypeptide selected from a TNF antagonist, an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic drug, an otic drug or nasal drug, a topical drug, a nutritional drug, and a cytokine antagonist.

7. An article of manufacture for human pharmaceutical or diagnostic use, comprising packaging material and a container comprising a solution or a lyophilized form of an IL-23p19 antibody according to claim 1.

8. The article of manufacture of claim 7, wherein said container is a component of a parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal delivery device or system.

9. The composition according to claim 5, wherein the antibody is conjugated to a detectable label or reporter.

* * * * *

SEQUENCE LISTING

<160> NUMBER OF SEQ ID NOS: 148

<210> SEQ ID NO 1
<211> LENGTH: 5
<212> TYPE: PRT
<213> ORGANISM: Homo sapiens

<400> SEQUENCE: 1

Asn Tyr Ala Ile Ser
1               5

<210> SEQ ID NO 2
<211> LENGTH: 5
<212> TYPE: PRT
<213> ORGANISM: Homo sapiens

<400> SEQUENCE: 2

Ser Asn Tyr Ile Ser
1               5

<210> SEQ ID NO 3
<211> LENGTH: 5
<212> TYPE: PRT
<213> ORGANISM: Homo sapiens

<400> SEQUENCE: 3

Asn Tyr Trp Ile Ser
1               5

<210> SEQ ID NO 4
<211> LENGTH: 5
<212> TYPE: PRT

```
<213> ORGANISM: Homo sapiens

<400> SEQUENCE: 4

Ser Tyr Trp Ile Thr
 1               5

<210> SEQ ID NO 5
<211> LENGTH: 5
<212> TYPE: PRT
<213> ORGANISM: Homo sapiens

<400> SEQUENCE: 5

Asn Tyr Trp Ile Gly
 1               5

<210> SEQ ID NO 6
<211> LENGTH: 5
<212> TYPE: PRT
<213> ORGANISM: Homo sapiens

<400> SEQUENCE: 6

Ser Phe Gly Met Ser
 1               5

<210> SEQ ID NO 7
<211> LENGTH: 17
<212> TYPE: PRT
<213> ORGANISM: Homo sapiens

<400> SEQUENCE: 7

Gly Ile Ile Pro Met Phe Gly Tyr Ala Asn Tyr Ala Gln Lys Phe Gln
 1               5                  10                  15

Gly

<210> SEQ ID NO 8
<211> LENGTH: 17
<212> TYPE: PRT
<213> ORGANISM: Homo sapiens

<400> SEQUENCE: 8

Gly Ile Ile Pro Val Phe Gly Phe Thr His Tyr Ala Gln Lys Phe Gln
 1               5                  10                  15

Gly

<210> SEQ ID NO 9
<211> LENGTH: 17
<212> TYPE: PRT
<213> ORGANISM: Homo sapiens

<400> SEQUENCE: 9

Gly Ile Ile Pro Ile Phe Gly His Ala Asn Tyr Ala Gln Lys Phe Gln
 1               5                  10                  15

Gly

<210> SEQ ID NO 10
<211> LENGTH: 17
<212> TYPE: PRT
<213> ORGANISM: Homo sapiens

<400> SEQUENCE: 10

Ile Ile Ile Pro Pro Ile Gly Asn Ala Trp Tyr Ala Gln Lys Phe Gln
 1               5                  10                  15
```

Gly

```
<210> SEQ ID NO 11
<211> LENGTH: 17
<212> TYPE: PRT
<213> ORGANISM: Homo sapiens

<400> SEQUENCE: 11

Leu Ile Asp Pro Asn Phe Gly Gly Ala Tyr Tyr Ala Gln Lys Phe Gln
1               5                   10                  15

Gly

<210> SEQ ID NO 12
<211> LENGTH: 17
<212> TYPE: PRT
<213> ORGANISM: Homo sapiens

<400> SEQUENCE: 12

Leu Ile Asp Pro Val Phe Gly Gly Ala Tyr Tyr Ala Gln Lys Phe Gln
1               5                   10                  15

Gly

<210> SEQ ID NO 13
<211> LENGTH: 17
<212> TYPE: PRT
<213> ORGANISM: Homo sapiens

<400> SEQUENCE: 13

Leu Ile Asp Pro Met Phe Gly Gly Ala Tyr Tyr Ala Gln Lys Phe Gln
1               5                   10                  15

Gly

<210> SEQ ID NO 14
<211> LENGTH: 16
<212> TYPE: PRT
<213> ORGANISM: Homo sapiens

<400> SEQUENCE: 14

Ile Asn Ala His Leu Gly Gly Thr Trp Tyr Ala Gln Lys Phe Gln Gly
1               5                   10                  15

<210> SEQ ID NO 15
<211> LENGTH: 17
<212> TYPE: PRT
<213> ORGANISM: Homo sapiens

<400> SEQUENCE: 15

Ile Ser Pro Gly Thr Gly Ile Asn Ala Tyr Tyr Ala Gln Lys Phe Gln
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: Synthesized human sequence
<220> FEATURE:
<221> NAME/KEY: unsure
<222> LOCATION: (1)
<223> OTHER INFORMATION: Where Xaa can be G, I, or L
<220> FEATURE:
<221> NAME/KEY: unsure
<222> LOCATION: (2)
```

```
<223> OTHER INFORMATION: Where Xaa can be I or S
<220> FEATURE:
<221> NAME/KEY: unsure
<222> LOCATION: (3)
<223> OTHER INFORMATION: Where Xaa can be I, P, N, or D
<220> FEATURE:
<221> NAME/KEY: unsure
<222> LOCATION: (4)
<223> OTHER INFORMATION: Where Xaa can be P, G, or A
<220> FEATURE:
<221> NAME/KEY: unsure
<222> LOCATION: (5)
<223> OTHER INFORMATION: Where Xaa can be I, M, P,
<223> OTHER INFORMATION: T, H, N, or V
<220> FEATURE:
<221> NAME/KEY: unsure
<222> LOCATION: (6)
<223> OTHER INFORMATION: Where Xaa can be F, I, G, or L
<220> FEATURE:
<221> NAME/KEY: unsure
<222> LOCATION: (7)
<223> OTHER INFORMATION: Where Xaa can be G or I
<220> FEATURE:
<221> NAME/KEY: unsure
<222> LOCATION: (8)
<223> OTHER INFORMATION: Where Xaa can be H, Y, N, or G
<220> FEATURE:
<221> NAME/KEY: unsure
<222> LOCATION: (9)
<223> OTHER INFORMATION: Where Xaa can be A or T
<220> FEATURE:
<221> NAME/KEY: unsure
<222> LOCATION: (10)
<223> OTHER INFORMATION: Where Xaa can be N, W, or Y

<400> SEQUENCE: 16

Xaa Xaa Xaa Xaa Xaa Xaa Xaa Xaa Xaa Xaa Tyr Ala Gln Lys Phe Gln
 1               5                  10                  15

Gly

<210> SEQ ID NO 17
<211> LENGTH: 17
<212> TYPE: PRT
<213> ORGANISM: Homo sapiens

<400> SEQUENCE: 17

Trp Ile Arg Pro Gly Asp Ser Asp Thr Arg Tyr Ser Pro Ser Phe Glu
 1               5                  10                  15

Gly

<210> SEQ ID NO 18
<211> LENGTH: 19
<212> TYPE: PRT
<213> ORGANISM: Homo sapiens

<400> SEQUENCE: 18

Val Ser Tyr Ile Ser Ser Ser Gly Ser Ser Thr Tyr Tyr Ala Asp Ser
 1               5                  10                  15

Val Lys Gly

<210> SEQ ID NO 19
<211> LENGTH: 17
<212> TYPE: PRT
<213> ORGANISM: Homo sapiens

<400> SEQUENCE: 19

Ile Ile Asp Pro Ser Asn Ser Tyr Thr Asn Tyr Ser Pro Ser Phe Gln
 1               5                  10                  15
```

Gly

<210> SEQ ID NO 20
<211> LENGTH: 17
<212> TYPE: PRT
<213> ORGANISM: Homo sapiens

<400> SEQUENCE: 20

Ile Ile Asp Pro Ser Asn Ser Tyr Thr Arg Tyr Ser Pro Ser Phe Gln
1               5                   10                  15

Gly

<210> SEQ ID NO 21
<211> LENGTH: 17
<212> TYPE: PRT
<213> ORGANISM: Homo sapiens

<400> SEQUENCE: 21

Ile Ile Asp Pro Ser Asn Ser Tyr Thr Asp Tyr Ser Pro Ser Phe Gln
1               5                   10                  15

Gly

<210> SEQ ID NO 22
<211> LENGTH: 17
<212> TYPE: PRT
<213> ORGANISM: Homo sapiens

<400> SEQUENCE: 22

Ile Ile Ser Pro Thr Gly Ser Val Thr Trp Tyr Ser Pro Ser Phe Gln
1               5                   10                  15

Gly

<210> SEQ ID NO 23
<211> LENGTH: 17
<212> TYPE: PRT
<213> ORGANISM: Homo sapiens

<400> SEQUENCE: 23

Ile Ile Ser Pro Thr Gly Ser Ser Thr Trp Tyr Ser Pro Ser Phe Gln
1               5                   10                  15

Gly

<210> SEQ ID NO 24
<211> LENGTH: 17
<212> TYPE: PRT
<213> ORGANISM: Homo sapiens

<400> SEQUENCE: 24

Phe Ile Ser Pro Asp Gly Ser His Thr Trp Tyr Ser Pro Ser Phe Gln
1               5                   10                  15

Gly

<210> SEQ ID NO 25
<211> LENGTH: 17
<212> TYPE: PRT
<213> ORGANISM: Homo sapiens

<400> SEQUENCE: 25

Ile Ile Ser Pro Ser Gly Ser Thr Thr Trp Tyr Ser Pro Ser Phe Gln
1               5                   10                  15

Gly

<210> SEQ ID NO 26
<211> LENGTH: 17
<212> TYPE: PRT
<213> ORGANISM: Homo sapiens

<400> SEQUENCE: 26

Ile Ile Ser Pro Thr Gly Ser Ala Thr Trp Tyr Ser Pro Ser Phe Gln
1               5                   10                  15
Gly

<210> SEQ ID NO 27
<211> LENGTH: 17
<212> TYPE: PRT
<213> ORGANISM: Homo sapiens

<400> SEQUENCE: 27

Ile Ile Asp Pro Val Ser Ser Trp Thr Lys Tyr Ser Pro Ser Phe Gln
1               5                   10                  15
Gly

<210> SEQ ID NO 28
<211> LENGTH: 17
<212> TYPE: PRT
<213> ORGANISM: Artificial Sequence
<220> FEATURE:
<223> OTHER INFORMATION: Synthesized human sequence
<220> FEATURE:
<221> NAME/KEY: unsure
<222> LOCATION: (3)
<223> OTHER INFORMATION: Where Xaa can be D or S
<220> FEATURE:
<221> NAME/KEY: unsure
<222> LOCATION: (5)
<223> OTHER INFORMATION: Where Xaa can be S, V, D, or T
<220> FEATURE:
<221> NAME/KEY: unsure
<222> LOCATION: (6)
<223> OTHER INFORMATION: Where Xaa can be N, S, or G
<220> FEATURE:
<221> NAME/KEY: unsure
<222> LOCATION: (8)
<223> OTHER INFORMATION: Where Xaa can be Y, W, T, H, V, S, or A
<220> FEATURE:
<221> NAME/KEY: unsure
<222> LOCATION: (10)
<223> OTHER INFORMATION: Where Xaa can be N, D, R, K, or W

<400> SEQUENCE: 28

Ile Ile Xaa Pro Xaa Xaa Ser Xaa Thr Xaa Tyr Ser Pro Ser Phe Gln
1               5                   10                  15
Gly

<210> SEQ ID NO 29
<211> LENGTH: 17
<212> TYPE: PRT
<213> ORGANISM: Homo sapiens

<400> SEQUENCE: 29

Asn Ile Ser Ser Ser Gly Ser Ser Thr Tyr Tyr Ala Asp Ser Val Lys
1               5                   10                  15
Gly

<210> SEQ ID NO 30
<211> LENGTH: 19
<212> TYPE: PRT

<213> ORGANISM: Homo sapiens

<400> SEQUENCE: 30

Asn Ile Glu His Lys Tyr Leu Asn Tyr Ala Thr Tyr Tyr Ala Ala Ser
 1               5                  10                  15

Val Lys Gly

<210> SEQ ID NO 31
<211> LENGTH: 19
<212> TYPE: PRT
<213> ORGANISM: Homo sapiens

<400> SEQUENCE: 31

Asn Ile Glu His Lys Phe Met Gly Tyr Thr Thr Tyr Ala Ala Gly
 1               5                  10                  15

Val Lys Gly

<210> SEQ ID NO 32
<211> LENGTH: 19
<212> TYPE: PRT
<213> ORGANISM: Homo sapiens

<400> SEQUENCE: 32

Gly Ile Glu His Lys Tyr Leu Ser Tyr Thr Thr His Tyr Ala Ala Ser
 1               5                  10                  15

Val Lys Gly

<210> SEQ ID NO 33
<211> LENGTH: 19
<212> TYPE: PRT
<213> ORGANISM: Homo sapiens

<400> SEQUENCE: 33

Ser Ile Glu His Lys Tyr Thr Gly Tyr Thr Thr Tyr Tyr Ala Ala Pro
 1               5                  10                  15

Val Lys Gly

<210> SEQ ID NO 34
<211> LENGTH: 19
<212> TYPE: PRT
<213> ORGANISM: Homo sapiens

<400> SEQUENCE: 34

Gln Ile Glu His Lys Tyr Leu Ser Tyr Thr Thr Leu Tyr Ala Ala Ser
 1               5                  10                  15

Val Lys Gly

<210> SEQ ID NO 35
<211> LENGTH: 19
<212> TYPE: PRT
<213> ORGANISM: Homo sapiens

<400> SEQUENCE: 35

Ser Ile Glu His Lys Tyr Leu Ser Tyr Thr Thr Phe Tyr Ala Ala Ser
 1               5                  10                  15

Val Lys Gly

<210> SEQ ID NO 36
<211> LENGTH: 19
<212> TYPE: PRT
<213> ORGANISM: Homo sapiens

<400> SEQUENCE: 36

Asn Ile Glu Gly Lys Tyr Thr Ser Tyr Thr Thr Tyr Tyr Ala Ala Ser
 1               5                  10                  15

Val Lys Gly

<210> SEQ ID NO 37
<211> LENGTH: 19
<212> TYPE: PRT
<213> ORGANISM: Homo sapiens

<400> SEQUENCE: 37

Gly Ile Glu His Lys Tyr Leu Ser Tyr Ala Thr Leu Tyr Ala Ala Ser
 1               5                  10                  15

Val Lys Gly

<210> SEQ ID NO 38
<211> LENGTH: 19
<212> TYPE: PRT
<213> ORGANISM: Homo sapiens

<400> SEQUENCE: 38

Asn Ile Glu His Lys Tyr Leu Gly Tyr Ala Thr Val Tyr Ala Ala Ser
 1               5                  10                  15

Val Lys Gly

<210> SEQ ID NO 39
<211> LENGTH: 19
<212> TYPE: PRT
<213> ORGANISM: Homo sapiens

<400> SEQUENCE: 39

Ser Ile Glu His Lys Tyr Leu Ser Tyr Ala Thr Tyr Tyr Ala Ala Gly
 1               5                  10                  15

Val Lys Gly

<210> SEQ ID NO 40
<211> LENGTH: 8
<212> TYPE: PRT
<213> ORGANISM: Homo sapiens

<400> SEQUENCE: 40

Asp Ile Tyr Ala Gly Met Asp Val
 1               5

<210> SEQ ID NO 41
<211> LENGTH: 18
<212> TYPE: PRT
<213> ORGANISM: Homo sapiens

<400> SEQUENCE: 41

Ser Lys Lys Gly Met Tyr Gly Gly Trp Thr Tyr Pro Leu Met Met Phe
 1               5                  10                  15

Asp Leu

<210> SEQ ID NO 42
<211> LENGTH: 7
<212> TYPE: PRT
<213> ORGANISM: Homo sapiens

<400> SEQUENCE: 42

His Tyr Tyr Gly Met Asp Tyr
1               5

<210> SEQ ID NO 43
<211> LENGTH: 12
<212> TYPE: PRT
<213> ORGANISM: Homo sapiens

<400> SEQUENCE: 43

Gly Thr Phe Trp Ser Phe Gly Asn Tyr Phe Ala Asn
1               5                   10

<210> SEQ ID NO 44
<211> LENGTH: 8
<212> TYPE: PRT
<213> ORGANISM: Homo sapiens

<400> SEQUENCE: 44

Trp Tyr Tyr Lys Pro Phe Asp Val
1               5

<210> SEQ ID NO 45
<211> LENGTH: 12
<212> TYPE: PRT
<213> ORGANISM: Homo sapiens

<400> SEQUENCE: 45

Tyr Trp Gly Thr Pro Tyr Leu Met Gln Phe Asp Asn
1               5                   10

<210> SEQ ID NO 46
<211> LENGTH: 12
<212> TYPE: PRT
<213> ORGANISM: Homo sapiens

<400> SEQUENCE: 46

Arg Ala Ser Gln Ser Val Leu Gly Asn Tyr Leu Ala
1               5                   10

<210> SEQ ID NO 47
<211> LENGTH: 12
<212> TYPE: PRT
<213> ORGANISM: Homo sapiens

<400> SEQUENCE: 47

Arg Ala Ser Gln Ser Val Ser Ser Asn Tyr Leu Ala
1               5                   10

<210> SEQ ID NO 48
<211> LENGTH: 13
<212> TYPE: PRT
<213> ORGANISM: Homo sapiens

<400> SEQUENCE: 48

Ser Gly Ser Ser Ser Asn Ile Gly Ser Tyr Tyr Val Asn
1               5                   10

<210> SEQ ID NO 49
<211> LENGTH: 11
<212> TYPE: PRT
<213> ORGANISM: Homo sapiens

<400> SEQUENCE: 49

Arg Ala Ser Gln Ser Ile Phe Tyr Asn Leu Ala
1               5                   10

<210> SEQ ID NO 50
<211> LENGTH: 14
<212> TYPE: PRT
<213> ORGANISM: Homo sapiens

<400> SEQUENCE: 50

Thr Gly Ser Ser Ser Asn Ile Gly Ser Gly Tyr Asp Val His
 1               5                  10

<210> SEQ ID NO 51
<211> LENGTH: 14
<212> TYPE: PRT
<213> ORGANISM: Homo sapiens

<400> SEQUENCE: 51

Thr Gly Thr Ser Ser Asp Val Gly Gly Tyr Asn Ser Val Ser
 1               5                  10

<210> SEQ ID NO 52
<211> LENGTH: 7
<212> TYPE: PRT
<213> ORGANISM: Homo sapiens

<400> SEQUENCE: 52

Gly Ala Ser Ser Arg Ala Thr
 1               5

<210> SEQ ID NO 53
<211> LENGTH: 7
<212> TYPE: PRT
<213> ORGANISM: Homo sapiens

<400> SEQUENCE: 53

Tyr Ala Ser Arg Arg Ala Thr
 1               5

<210> SEQ ID NO 54
<211> LENGTH: 7
<212> TYPE: PRT
<213> ORGANISM: Homo sapiens

<400> SEQUENCE: 54

Gly Asn Thr His Arg Pro Ser
 1               5

<210> SEQ ID NO 55
<211> LENGTH: 7
<212> TYPE: PRT
<213> ORGANISM: Homo sapiens

<400> SEQUENCE: 55

Gly Ala Ser Asn Arg Ala Thr
 1               5

<210> SEQ ID NO 56
<211> LENGTH: 7
<212> TYPE: PRT
<213> ORGANISM: Homo sapiens

<400> SEQUENCE: 56

Gly Asn Ser Lys Arg Pro Ser
 1               5

<210> SEQ ID NO 57
<211> LENGTH: 7
<212> TYPE: PRT
<213> ORGANISM: Homo sapiens

<400> SEQUENCE: 57

Ser Val Ser Ser Arg Pro Ser
1               5

<210> SEQ ID NO 58
<211> LENGTH: 9
<212> TYPE: PRT
<213> ORGANISM: Homo sapiens

<400> SEQUENCE: 58

His Gln Tyr Gly Ser Ile Ser Thr Thr
1               5

<210> SEQ ID NO 59
<211> LENGTH: 9
<212> TYPE: PRT
<213> ORGANISM: Homo sapiens

<400> SEQUENCE: 59

Gln Gln Tyr Ser His Leu Leu Ile Thr
1               5

<210> SEQ ID NO 60
<211> LENGTH: 9
<212> TYPE: PRT
<213> ORGANISM: Homo sapiens

<400> SEQUENCE: 60

Gln Gln Tyr Ser His Ile Ser Leu Thr
1               5

<210> SEQ ID NO 61
<211> LENGTH: 9
<212> TYPE: PRT
<213> ORGANISM: Homo sapiens

<400> SEQUENCE: 61

Gln Gln Phe Ala His Ile Leu Leu Thr
1               5

<210> SEQ ID NO 62
<211> LENGTH: 9
<212> TYPE: PRT
<213> ORGANISM: Homo sapiens

<400> SEQUENCE: 62

Gln Gln Thr Ser Asn Thr Pro Phe Thr
1               5

<210> SEQ ID NO 63
<211> LENGTH: 9
<212> TYPE: PRT
<213> ORGANISM: Homo sapiens

<400> SEQUENCE: 63

Gln Gln Phe Ile Thr Tyr Leu Pro Thr
1               5

<210> SEQ ID NO 64
<211> LENGTH: 9

```
<212> TYPE: PRT
<213> ORGANISM: Homo sapiens

<400> SEQUENCE: 64

Gln Gln Asp Ala Leu Ser Pro Phe Thr
1               5

<210> SEQ ID NO 65
<211> LENGTH: 9
<212> TYPE: PRT
<213> ORGANISM: Homo sapiens

<400> SEQUENCE: 65

Gln Gln Asp Arg Gly Thr Pro Phe Thr
1               5

<210> SEQ ID NO 66
<211> LENGTH: 9
<212> TYPE: PRT
<213> ORGANISM: Homo sapiens

<400> SEQUENCE: 66

Gln Gln Ser Leu Asn Ile Pro Phe Thr
1               5

<210> SEQ ID NO 67
<211> LENGTH: 9
<212> TYPE: PRT
<213> ORGANISM: Homo sapiens

<400> SEQUENCE: 67

Gln Gln Asp Thr Ser Ser Pro Phe Thr
1               5

<210> SEQ ID NO 68
<211> LENGTH: 10
<212> TYPE: PRT
<213> ORGANISM: Artificial Sequence
<220> FEATURE:
<223> OTHER INFORMATION: Synthesized human sequence
<220> FEATURE:
<221> NAME/KEY: unsure
<222> LOCATION: (3)
<223> OTHER INFORMATION: Where Xaa can be T, F, D, or S
<220> FEATURE:
<221> NAME/KEY: unsure
<222> LOCATION: (4)
<223> OTHER INFORMATION: Where Xaa can be S, I, A, T, R, or L
<220> FEATURE:
<221> NAME/KEY: unsure
<222> LOCATION: (5)
<223> OTHER INFORMATION: Where Xaa can be N, T, L, S, or G
<220> FEATURE:
<221> NAME/KEY: unsure
<222> LOCATION: (6)
<223> OTHER INFORMATION: Where Xaa can be T, Y, S, or I
<220> FEATURE:
<221> NAME/KEY: unsure
<222> LOCATION: (7)
<223> OTHER INFORMATION: Where Xaa can be P or L
<220> FEATURE:
<221> NAME/KEY: unsure
<222> LOCATION: (8)
<223> OTHER INFORMATION: Where Xaa can be F or P

<400> SEQUENCE: 68

Gln Gln Xaa Xaa Xaa Xaa Xaa Xaa Phe Thr
1               5                   10
```

```
<210> SEQ ID NO 69
<211> LENGTH: 11
<212> TYPE: PRT
<213> ORGANISM: Homo sapiens

<400> SEQUENCE: 69

Gln Thr Tyr Ala Ser Leu Gly Pro Gly Glu Val
1               5                   10

<210> SEQ ID NO 70
<211> LENGTH: 9
<212> TYPE: PRT
<213> ORGANISM: Homo sapiens

<400> SEQUENCE: 70

Gln Gln Tyr Ser Ser Glu Pro Val Thr
1               5

<210> SEQ ID NO 71
<211> LENGTH: 9
<212> TYPE: PRT
<213> ORGANISM: Homo sapiens

<400> SEQUENCE: 71

Ser Ser Trp Thr Pro Ser Ser Val Val
1               5

<210> SEQ ID NO 72
<211> LENGTH: 11
<212> TYPE: PRT
<213> ORGANISM: Homo sapiens

<400> SEQUENCE: 72

Ser Ser Trp Thr Asp Thr Pro Asn Met Ile Val
1               5                   10

<210> SEQ ID NO 73
<211> LENGTH: 11
<212> TYPE: PRT
<213> ORGANISM: Homo sapiens

<400> SEQUENCE: 73

Ala Ser Trp Thr Asp Gly Leu Ser Leu Val Val
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthesized human sequence
<220> FEATURE:
<221> NAME/KEY: unsure
<222> LOCATION: (1)
<223> OTHER INFORMATION: Where Xaa can be S or A
<220> FEATURE:
<221> NAME/KEY: unsure
<222> LOCATION: (6)
<223> OTHER INFORMATION: Where Xaa can be T or G
<220> FEATURE:
<221> NAME/KEY: unsure
<222> LOCATION: (7)
<223> OTHER INFORMATION: Where Xaa can be P or L
<220> FEATURE:
<221> NAME/KEY: unsure
<222> LOCATION: (8)
<223> OTHER INFORMATION: Where Xaa can be S or N
<220> FEATURE:
<221> NAME/KEY: unsure
```

```
<222> LOCATION: (9)
<223> OTHER INFORMATION: Where Xaa can be S, M, or L
<220> FEATURE:
<221> NAME/KEY: unsure
<222> LOCATION: (10)
<223> OTHER INFORMATION: Where Xaa can be I or V

<400> SEQUENCE: 74

Xaa Ser Trp Thr Asp Xaa Xaa Xaa Xaa Val
 1               5                  10

<210> SEQ ID NO 75
<211> LENGTH: 11
<212> TYPE: PRT
<213> ORGANISM: Homo sapiens

<400> SEQUENCE: 75

Ser Ser Tyr Asp Thr Asn Lys Pro Leu Val Val
 1               5                  10

<210> SEQ ID NO 76
<211> LENGTH: 11
<212> TYPE: PRT
<213> ORGANISM: Homo sapiens

<400> SEQUENCE: 76

Gly Ser Tyr Asp Val Tyr Gly Arg Phe Tyr Val
 1               5                  10

<210> SEQ ID NO 77
<211> LENGTH: 11
<212> TYPE: PRT
<213> ORGANISM: Homo sapiens

<400> SEQUENCE: 77

Ser Ser Tyr Tyr Phe Tyr Leu Gln Arg Ile Val
 1               5                  10

<210> SEQ ID NO 78
<211> LENGTH: 11
<212> TYPE: PRT
<213> ORGANISM: Homo sapiens

<400> SEQUENCE: 78

Gln Thr Tyr Tyr Phe Ser Tyr Ser Gly Pro Val
 1               5                  10

<210> SEQ ID NO 79
<211> LENGTH: 11
<212> TYPE: PRT
<213> ORGANISM: Homo sapiens

<400> SEQUENCE: 79

Gly Ser Trp Asp Pro Ile Phe Ser Tyr Glu Val
 1               5                  10

<210> SEQ ID NO 80
<211> LENGTH: 117
<212> TYPE: PRT
<213> ORGANISM: Homo sapiens

<400> SEQUENCE: 80

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Asn Tyr
```

```
                     20                  25                  30

Ala Ile Ser Trp Val Arg Gln Ala Pro Gly Gln Gly Leu Glu Trp Met
            35                  40                  45

Gly Gly Ile Ile Pro Met Phe Gly Tyr Ala Asn Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asp Ile Tyr Ala Gly Met Asp Val Trp Gly Gln Gly Thr Leu
            100                 105                 110

Val Thr Val Ser Ser
        115

<210> SEQ ID NO 81
<211> LENGTH: 117
<212> TYPE: PRT
<213> ORGANISM: Homo sapiens

<400> SEQUENCE: 81

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
            35                  40                  45

Gly Gly Ile Ile Pro Val Phe Gly Phe Thr His Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asp Ile Tyr Ala Gly Met Asp Val Trp Gly Gln Gly Thr Leu
            100                 105                 110

Val Thr Val Ser Ser
        115

<210> SEQ ID NO 82
<211> LENGTH: 108
<212> TYPE: PRT
<213> ORGANISM: Homo sapiens

<400> SEQUENCE: 82

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Leu Gly Asn
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
        50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys His Gln Tyr Gly Ser Ile Ser
                85                  90                  95

Thr Thr Phe Gly Gln Gly Thr Lys Val Glu Ile Lys
```

<210> SEQ ID NO 83
<211> LENGTH: 108
<212> TYPE: PRT
<213> ORGANISM: Homo sapiens

<400> SEQUENCE: 83

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Leu Gly Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ser His Ile Ser
                85                  90                  95

Leu Thr Phe Gly Gln Gly Thr Lys Val Glu Ile Lys
            100                 105

<210> SEQ ID NO 84
<211> LENGTH: 108
<212> TYPE: PRT
<213> ORGANISM: Homo sapiens

<400> SEQUENCE: 84

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Leu Gly Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ser His Leu Ile
                85                  90                  95

Ile Thr Phe Gly Gln Gly Thr Lys Val Glu Ile Lys
            100                 105

<210> SEQ ID NO 85
<211> LENGTH: 108
<212> TYPE: PRT
<213> ORGANISM: Homo sapiens

<400> SEQUENCE: 85

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Leu Gly Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Phe Ala His Ile Leu
                85                  90                  95

Leu Thr Phe Gly Gln Gly Thr Lys Val Glu Ile Lys
            100                 105

<210> SEQ ID NO 86
<211> LENGTH: 127
<212> TYPE: PRT
<213> ORGANISM: Homo sapiens

<400> SEQUENCE: 86

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Gly Ile Ile Pro Ile Phe Gly His Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
        115                 120                 125

<210> SEQ ID NO 87
<211> LENGTH: 127
<212> TYPE: PRT
<213> ORGANISM: Homo sapiens

<400> SEQUENCE: 87

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Ile Ile Ile Pro Pro Ile Gly Asn Ala Trp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
        115                 120                 125

<210> SEQ ID NO 88
<211> LENGTH: 127
<212> TYPE: PRT
<213> ORGANISM: Homo sapiens

<400> SEQUENCE: 88

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Ile Ser Pro Gly Thr Gly Ile Asn Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
        115                 120                 125

<210> SEQ ID NO 89
<211> LENGTH: 126
<212> TYPE: PRT
<213> ORGANISM: Homo sapiens

<400> SEQUENCE: 89

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Ile Asn Ala His Leu Gly Gly Thr Trp Tyr Ala Gln Lys Phe Gln
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ser Lys Lys Gly Met Tyr Gly Gly Trp Thr Tyr Pro Leu Met Met
            100                 105                 110

Phe Asp Leu Trp Gly Gln Gly Thr Leu Val Thr Val Ser Ser
        115                 120                 125

<210> SEQ ID NO 90
<211> LENGTH: 127
<212> TYPE: PRT
<213> ORGANISM: Homo sapiens

<400> SEQUENCE: 90

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Leu Ile Asp Pro Asn Phe Gly Gly Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
        115                 120                 125

<210> SEQ ID NO 91
<211> LENGTH: 127
<212> TYPE: PRT
<213> ORGANISM: Homo sapiens

<400> SEQUENCE: 91

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Leu Ile Asp Pro Val Phe Gly Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
        115                 120                 125

<210> SEQ ID NO 92
<211> LENGTH: 127
<212> TYPE: PRT
<213> ORGANISM: Homo sapiens

<400> SEQUENCE: 92

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Leu Ile Asp Pro Met Phe Gly Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
        115                 120                 125

<210> SEQ ID NO 93
<211> LENGTH: 108

```
<212> TYPE: PRT
<213> ORGANISM: Homo sapiens

<400> SEQUENCE: 93

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Tyr Ala Ser Arg Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Thr Ser Asn Thr Pro
                85                  90                  95

Phe Thr Phe Gly Gln Gly Thr Lys Val Glu Ile Lys
            100                 105

<210> SEQ ID NO 94
<211> LENGTH: 108
<212> TYPE: PRT
<213> ORGANISM: Homo sapiens

<400> SEQUENCE: 94

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Tyr Ala Ser Arg Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Thr Ser Asn Thr Pro
                85                  90                  95

Phe Thr Phe Gly Gln Gly Thr Lys Val Glu Ile Lys
            100                 105

<210> SEQ ID NO 95
<211> LENGTH: 108
<212> TYPE: PRT
<213> ORGANISM: Homo sapiens

<400> SEQUENCE: 95

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Tyr Ala Ser Arg Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Phe Ile Thr Tyr Leu
```

Pro Thr Phe Gly Gln Gly Thr Lys Val Glu Ile Lys
                100                 105

<210> SEQ ID NO 96
<211> LENGTH: 108
<212> TYPE: PRT
<213> ORGANISM: Homo sapiens

<400> SEQUENCE: 96

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Tyr Ala Ser Arg Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Asp Ala Leu Ser Pro
                85                  90                  95

Phe Thr Phe Gly Gln Gly Thr Lys Val Glu Ile Lys
            100                 105

<210> SEQ ID NO 97
<211> LENGTH: 108
<212> TYPE: PRT
<213> ORGANISM: Homo sapiens

<400> SEQUENCE: 97

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Tyr Ala Ser Arg Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Asp Arg Gly Thr Pro
                85                  90                  95

Phe Thr Phe Gly Gln Gly Thr Lys Val Glu Ile Lys
            100                 105

<210> SEQ ID NO 98
<211> LENGTH: 108
<212> TYPE: PRT
<213> ORGANISM: Homo sapiens

<400> SEQUENCE: 98

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

```
Ile Tyr Tyr Ala Ser Arg Arg Ala Thr Gly Val Pro Ala Arg Phe Ser
        50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Ser Leu Asn Ile Pro
                85                  90                  95

Phe Thr Phe Gly Gln Gly Thr Lys Val Glu Ile Lys
            100                 105
```

<210> SEQ ID NO 99
<211> LENGTH: 116
<212> TYPE: PRT
<213> ORGANISM: Homo sapiens

<400> SEQUENCE: 99

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
                20                  25                  30

Trp Ile Ser Trp Val Arg Gln Ala Pro Gly Lys Gly Leu Glu Trp Met
            35                  40                  45

Gly Trp Ile Arg Pro Gly Asp Ser Asp Thr Arg Tyr Ser Pro Ser Phe
 50                  55                  60

Glu Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg His Tyr Tyr Gly Met Asp Tyr Trp Gly Gln Gly Thr Leu Val
            100                 105                 110

Thr Val Ser Ser
        115
```

<210> SEQ ID NO 100
<211> LENGTH: 110
<212> TYPE: PRT
<213> ORGANISM: Homo sapiens

<400> SEQUENCE: 100

```
Asp Ile Val Leu Thr Gln Pro Pro Ser Val Ser Gly Ala Pro Gly Gln
 1               5                  10                  15

Arg Val Thr Ile Ser Cys Ser Gly Ser Ser Ser Asn Ile Gly Ser Tyr
                20                  25                  30

Tyr Val Asn Trp Tyr Gln Gln Leu Pro Gly Thr Ala Pro Lys Leu Leu
            35                  40                  45

Ile Tyr Gly Asn Thr His Arg Pro Ser Gly Val Pro Asp Arg Phe Ser
 50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Gln Thr Tyr Ala Ser Leu Gly
                85                  90                  95

Pro Gly Glu Val Phe Gly Gly Gly Thr Lys Leu Thr Val Leu
            100                 105                 110
```

<210> SEQ ID NO 101
<211> LENGTH: 121
<212> TYPE: PRT
<213> ORGANISM: Homo sapiens

<400> SEQUENCE: 101

Gln Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile Thr Trp Val Arg Gln Ala Pro Gly Lys Gly Leu Glu Trp Val
        35                  40                  45

Ser Tyr Ile Ser Ser Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Phe Trp Ser Phe Gly Asn Tyr Phe Ala Asn Trp Gly
            100                 105                 110

Gln Gly Thr Leu Val Thr Val Ser Ser
        115                 120

<210> SEQ ID NO 102
<211> LENGTH: 107
<212> TYPE: PRT
<213> ORGANISM: Homo sapiens

<400> SEQUENCE: 102

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Phe Tyr Asn
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Tyr Ser Ser Glu Pro Val
                85                  90                  95

Thr Phe Gly Gln Gly Thr Lys Val Glu Ile Lys
            100                 105

<210> SEQ ID NO 103
<211> LENGTH: 117
<212> TYPE: PRT
<213> ORGANISM: Homo sapiens

<400> SEQUENCE: 103

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Asp Pro Ser Asn Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

```
Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
        115

<210> SEQ ID NO 104
<211> LENGTH: 117
<212> TYPE: PRT
<213> ORGANISM: Homo sapiens

<400> SEQUENCE: 104

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Asp Pro Ser Asn Ser Tyr Thr Asp Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
        115

<210> SEQ ID NO 105
<211> LENGTH: 117
<212> TYPE: PRT
<213> ORGANISM: Homo sapiens

<400> SEQUENCE: 105

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Asp Pro Ser Asn Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
        115

<210> SEQ ID NO 106
<211> LENGTH: 117
<212> TYPE: PRT
<213> ORGANISM: Homo sapiens
```

-continued

<400> SEQUENCE: 106

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Asp Pro Ser Asn Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
        115

<210> SEQ ID NO 107
<211> LENGTH: 117
<212> TYPE: PRT
<213> ORGANISM: Homo sapiens

<400> SEQUENCE: 107

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Asp Pro Val Ser Ser Trp Thr Lys Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
        115

<210> SEQ ID NO 108
<211> LENGTH: 117
<212> TYPE: PRT
<213> ORGANISM: Homo sapiens

<400> SEQUENCE: 108

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Ser Pro Ser Gly Ser Thr Thr Trp Tyr Ser Pro Ser Phe
    50                  55                  60

Gln Gly Gln Val Thr Ile Ser Ala Asp Lys Ser Ile Ser Thr Ala Tyr

```
              65                  70                  75                  80
Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
        115

<210> SEQ ID NO 109
<211> LENGTH: 117
<212> TYPE: PRT
<213> ORGANISM: Homo sapiens

<400> SEQUENCE: 109

Gln Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Ser Asn Tyr
             20                  25                  30

Trp Ile Gly Trp Val Arg Gln Met Pro Gly Lys Gly Leu Glu Trp Met
         35                  40                  45

Gly Phe Ile Ser Pro Asp Gly Ser His Thr Trp Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
        115

<210> SEQ ID NO 110
<211> LENGTH: 117
<212> TYPE: PRT
<213> ORGANISM: Homo sapiens

<400> SEQUENCE: 110

Gln Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Ser Asn Tyr
             20                  25                  30

Trp Ile Gly Trp Val Arg Gln Met Pro Gly Lys Gly Leu Glu Trp Met
         35                  40                  45

Gly Ile Ile Ser Pro Thr Gly Ser Val Thr Trp Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
        115

<210> SEQ ID NO 111
<211> LENGTH: 117
<212> TYPE: PRT
```

<213> ORGANISM: Homo sapiens

<400> SEQUENCE: 111

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Ser Pro Thr Gly Ser Ser Thr Trp Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
        115

<210> SEQ ID NO 112
<211> LENGTH: 117
<212> TYPE: PRT
<213> ORGANISM: Homo sapiens

<400> SEQUENCE: 112

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Ser Pro Thr Gly Ser Ala Thr Trp Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
        115

<210> SEQ ID NO 113
<211> LENGTH: 109
<212> TYPE: PRT
<213> ORGANISM: Homo sapiens

<400> SEQUENCE: 113

Asp Ile Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Lys Arg Pro Ser Gly Val Pro Asp Arg Phe
    50                  55                  60

```
Ser Gly Ser Lys Ser Gly Thr Ser Ala Ser Leu Ala Ile Thr Gly Leu
 65                  70                  75                  80

Gln Ser Glu Asp Glu Ala Asp Tyr Tyr Cys Ser Ser Trp Thr Pro Ser
                 85                  90                  95

Ser Val Val Phe Gly Gly Gly Thr Lys Leu Thr Val Leu
            100                 105
```

<210> SEQ ID NO 114
<211> LENGTH: 111
<212> TYPE: PRT
<213> ORGANISM: Homo sapiens

<400> SEQUENCE: 114

```
Asp Ile Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ser Gly
                 20                  25                  30

Tyr Asp Val His Trp Tyr Gln Gln Leu Pro Gly Thr Ala Pro Lys Leu
             35                  40                  45

Leu Ile Tyr Gly Asn Ser Lys Arg Pro Ser Gly Val Pro Asp Arg Phe
         50                  55                  60

Ser Gly Ser Lys Ser Gly Thr Ser Ala Ser Leu Ala Ile Thr Gly Leu
 65                  70                  75                  80

Gln Ser Glu Asp Glu Ala Asp Tyr Tyr Cys Ser Ser Trp Thr Asp Thr
                 85                  90                  95

Pro Asn Met Ile Val Phe Gly Gly Gly Thr Lys Leu Thr Val Leu
            100                 105                 110
```

<210> SEQ ID NO 115
<211> LENGTH: 111
<212> TYPE: PRT
<213> ORGANISM: Homo sapiens

<400> SEQUENCE: 115

```
Asp Ile Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ser Gly
                 20                  25                  30

Tyr Asp Val His Trp Tyr Gln Gln Leu Pro Gly Thr Ala Pro Lys Leu
             35                  40                  45

Leu Ile Tyr Gly Asn Ser Lys Arg Pro Ser Gly Val Pro Asp Arg Phe
         50                  55                  60

Ser Gly Ser Lys Ser Gly Thr Ser Ala Ser Leu Ala Ile Thr Gly Leu
 65                  70                  75                  80

Gln Ser Glu Asp Glu Ala Asp Tyr Tyr Cys Ala Ser Trp Thr Asp Gly
                 85                  90                  95

Leu Ser Leu Val Val Phe Gly Gly Gly Thr Lys Leu Thr Val Leu
            100                 105                 110
```

<210> SEQ ID NO 116
<211> LENGTH: 111
<212> TYPE: PRT
<213> ORGANISM: Homo sapiens

<400> SEQUENCE: 116

```
Gln Ser Val Leu Thr Gln Pro Pro Ser Val Ser Gly Ala Pro Gly Gln
 1               5                  10                  15
```

Arg Val Thr Ile Ser Cys Thr Gly Ser Ser Asn Ile Gly Ser Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Lys Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ala Ser Trp Thr Asp Gly
                85                  90                  95

Leu Ser Leu Val Val Phe Gly Gly Gly Thr Lys Leu Thr Val Leu
            100                 105                 110

<210> SEQ ID NO 117
<211> LENGTH: 121
<212> TYPE: PRT
<213> ORGANISM: Homo sapiens

<400> SEQUENCE: 117

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Asn Ile Ser Ser Ser Gly Ser Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Gly Thr Pro Tyr Leu Met Gln Phe Asp Asn Trp Gly
            100                 105                 110

Gln Gly Thr Leu Val Thr Val Ser Ser
        115                 120

<210> SEQ ID NO 118
<211> LENGTH: 123
<212> TYPE: PRT
<213> ORGANISM: Homo sapiens

<400> SEQUENCE: 118

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Asn Ile Glu His Lys Phe Met Gly Tyr Thr Thr Tyr Tyr Ala Ala
        50                  55                  60

Gly Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
            115                 120

<210> SEQ ID NO 119
<211> LENGTH: 123
<212> TYPE: PRT
<213> ORGANISM: Homo sapiens

<400> SEQUENCE: 119

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Glu His Lys Tyr Thr Gly Tyr Thr Thr Tyr Tyr Ala Ala
    50                  55                  60

Pro Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
            115                 120

<210> SEQ ID NO 120
<211> LENGTH: 123
<212> TYPE: PRT
<213> ORGANISM: Homo sapiens

<400> SEQUENCE: 120

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Asn Ile Glu His Lys Tyr Thr Ser Tyr Thr Thr Tyr Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
            115                 120

<210> SEQ ID NO 121
<211> LENGTH: 123
<212> TYPE: PRT
<213> ORGANISM: Homo sapiens

<400> SEQUENCE: 121

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe

```
            20                  25                  30
Gly Met Ser Trp Val Arg Gln Ala Pro Gly Lys Gly Leu Glu Trp Val
            35                  40                  45

Ser Asn Ile Glu His Lys Tyr Leu Asn Tyr Ala Thr Tyr Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
            115                 120

<210> SEQ ID NO 122
<211> LENGTH: 123
<212> TYPE: PRT
<213> ORGANISM: Homo sapiens

<400> SEQUENCE: 122

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Asn Ile Glu His Lys Tyr Leu Gly Tyr Ala Thr Val Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
            115                 120

<210> SEQ ID NO 123
<211> LENGTH: 123
<212> TYPE: PRT
<213> ORGANISM: Homo sapiens

<400> SEQUENCE: 123

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Glu His Lys Tyr Leu Ser Tyr Ala Thr Tyr Tyr Ala Ala
    50                  55                  60

Gly Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
```

100            105            110

Trp Gly Gln Gly Thr Leu Val Thr Val Ser Ser
        115                 120

<210> SEQ ID NO 124
<211> LENGTH: 123
<212> TYPE: PRT
<213> ORGANISM: Homo sapiens

<400> SEQUENCE: 124

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Glu His Lys Tyr Leu Ser Tyr Thr Thr Phe Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
        115                 120

<210> SEQ ID NO 125
<211> LENGTH: 123
<212> TYPE: PRT
<213> ORGANISM: Homo sapiens

<400> SEQUENCE: 125

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Gly Ile Glu His Lys Tyr Leu Ser Tyr Thr Thr His Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
        115                 120

<210> SEQ ID NO 126
<211> LENGTH: 123
<212> TYPE: PRT
<213> ORGANISM: Homo sapiens

<400> SEQUENCE: 126

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
                35                  40                  45

Ser Gln Ile Glu His Lys Tyr Leu Ser Tyr Thr Thr Leu Tyr Ala Ala
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
            115                 120

<210> SEQ ID NO 127
<211> LENGTH: 123
<212> TYPE: PRT
<213> ORGANISM: Homo sapiens

<400> SEQUENCE: 127

Gln Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
                35                  40                  45

Ser Gly Ile Glu His Lys Tyr Leu Ser Tyr Ala Thr Leu Tyr Ala Ala
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
            115                 120

<210> SEQ ID NO 128
<211> LENGTH: 111
<212> TYPE: PRT
<213> ORGANISM: Homo sapiens

<400> SEQUENCE: 128

Asp Ile Ala Leu Thr Gln Pro Ala Ser Val Ser Gly Ser Pro Gly Gln
 1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
                35                  40                  45

Met Ile Tyr Ser Val Ser Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Thr Asn
                85                  90                  95

```
Lys Pro Leu Val Val Phe Gly Gly Gly Thr Lys Leu Thr Val Leu
            100                 105                 110
```

<210> SEQ ID NO 129
<211> LENGTH: 111
<212> TYPE: PRT
<213> ORGANISM: Homo sapiens

<400> SEQUENCE: 129

```
Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Ser Val Ser Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Tyr Phe Tyr
                85                  90                  95

Leu Gln Arg Ile Val Phe Gly Gly Gly Thr Lys Leu Thr Val Leu
            100                 105                 110
```

<210> SEQ ID NO 130
<211> LENGTH: 111
<212> TYPE: PRT
<213> ORGANISM: Homo sapiens

<400> SEQUENCE: 130

```
Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Ser Val Ser Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Thr Tyr Tyr Phe Ser
                85                  90                  95

Tyr Ser Gly Pro Val Phe Gly Gly Gly Thr Lys Leu Thr Val Leu
            100                 105                 110
```

<210> SEQ ID NO 131
<211> LENGTH: 111
<212> TYPE: PRT
<213> ORGANISM: Homo sapiens

<400> SEQUENCE: 131

```
Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45
```

```
Met Ile Tyr Ser Val Ser Ser Arg Pro Ser Gly Val Ser Asn Arg Phe
            50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Ser Tyr Asp Val Tyr
                 85                  90                  95

Gly Arg Phe Tyr Val Phe Gly Gly Gly Thr Lys Leu Thr Val Leu
            100                 105                 110

<210> SEQ ID NO 132
<211> LENGTH: 111
<212> TYPE: PRT
<213> ORGANISM: Homo sapiens

<400> SEQUENCE: 132

Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Ala Pro Lys Leu
             35                  40                  45

Met Ile Tyr Ser Val Ser Ser Arg Pro Ser Gly Val Ser Asn Arg Phe
            50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Ser Trp Asp Pro Ile
                 85                  90                  95

Phe Ser Tyr Glu Val Phe Gly Gly Gly Thr Lys Leu Thr Val Leu
            100                 105                 110

<210> SEQ ID NO 133
<211> LENGTH: 381
<212> TYPE: DNA
<213> ORGANISM: Homo sapiens

<400> SEQUENCE: 133
caggtgcagc tggtgcagtc tggggctgag gtgaagaagc ctgggtcctc ggtgaaggtc        60
tcctgcaagg cttctggagg caccttcagc agcaactaca tcagctgggt gcgacaggcc       120
cctggacaag gcttgagtg gatggggatc agccctggca ccggtatcaa cgcatactac        180
gcacagaagt tccagggcag agtcacgatt accgcggacg aatccacgag cacagcctac       240
atggagctga gcagcctgag atctgaggac acggccgtgt attactgtgc gagaagcaag       300
aagggcatgt acgcggcctg gacctacccc ctgatgatgt tcgacctgtg gggccagggc       360
accctggtga ccgtgagcag c                                                 381

<210> SEQ ID NO 134
<211> LENGTH: 381
<212> TYPE: DNA
<213> ORGANISM: Homo sapiens

<400> SEQUENCE: 134
caggtgcagc tggtgcagag cggcgccgag gtgaagaagc ccggcagcag cgtgaaggtg        60
agctgcaagg ccagcggcgg caccttcagc agcaactaca tcagctgggt gcgccaggcc       120
cccggccagg gcctggagtg gatgggcatc agccccggca ccggcatcaa cgcctactac       180
gcccagaagt tccagggccg cgtgaccatc accgccgacg agagcaccag caccgcctac       240
```

```
atggagctga gcagcctgcg cagcgaggac accgccgtgt actactgcgc ccgcagcaag    300
aagggcatgt acggcggctg gacctacccc ctgatgatgt cgacctgtg gggccagggc    360 accctggtga ccgtgagcag c                                              381
```

<210> SEQ ID NO 135
<211> LENGTH: 381
<212> TYPE: DNA
<213> ORGANISM: Homo sapiens

<400> SEQUENCE: 135

```
caggtgcaat tggttcagtc tggcgcggaa gtgaaaaaac cgggcagcag cgtgaaagtg     60
agctgcaaag cctccggagg cacttttttct tctaattata tttcttgggt gcgccaagcc   120
cctgggcagg gtctcgagtg gatgggcatt tctcctggta ctggtattaa tgcttattat   180
gctcagaagt ttcagggtcg ggtgaccatt accgcggatg aaagcaccag caccgcgtat   240
atggaactga gcagcctgcg tagcgaagat acggccgtgt attattgcgc gcgttctaag   300
aagggtatgt atggtggttg gacttatcct cttatgatgt ttgatctttg gggccaaggc    360
accctggtga cggttagctc a                                              381
```

<210> SEQ ID NO 136
<211> LENGTH: 324
<212> TYPE: DNA
<213> ORGANISM: Homo sapiens

<400> SEQUENCE: 136

```
gagatcgtgc tgacccagag ccccgccacc ctgagcctga gccccggcga gcgcgccacc     60
ctgagctgcc gcgccagcca gagcgtgagc agcaactacc tggcctggta ccagcagaag   120
cccggccagg ccccccgcct gctgatctac tacgccagcc gcgcgccac cggcgtgccc    180 gcccgcttca gcggcagcgg cagcggcacc gacttcaccc tgaccatcag cagcctggag   240
cccgaggact tcgccgtgta ctactgccag cagaccagca caccccctt caccttcggc    300 cagggcacca aggtggagat caag                                           324
```

<210> SEQ ID NO 137
<211> LENGTH: 324
<212> TYPE: DNA
<213> ORGANISM: Homo sapiens

<400> SEQUENCE: 137

```
gaaattgtgt tgacacagtc tccagccacc ctgtctttgt ctccagggga aagagccacc     60
ctctcctgca gggccagtca gagtgttagc agcaactact tagcctggta ccaacagaaa   120
cctggccagg ctcccaggct cctcatctat tacgcatccc gcagggccac tggcgtgcca   180
gccaggttca gtggcagtgg gtctgggaca gacttcactc tcaccatcag cagcctagag   240
cctgaagatt ttgcagttta ttactgtcag cagacttcta atactccttt tacctttggc   300
cagggtacga aagttgaaat taaa                                           324
```

<210> SEQ ID NO 138
<211> LENGTH: 324
<212> TYPE: DNA
<213> ORGANISM: Homo sapiens

<400> SEQUENCE: 138

```
gagatcgtgc tgacccagag cccggcgacc ctgagcctgt ctccgggcga acgtgcgacc     60
ctgagctgca gagcgagcca gtctgtttct tctaattatc tggcttggta ccagcagaaa   120
```

```
ccaggtcaag caccgcgtct attaatttat tatgcttctc gtcgtgcaac tggggtcccg      180
gcgcgtttta gcggctctgg atccggcacg gattttaccc tgaccattag cagcctggaa      240
cctgaagact ttgcggtgta ttattgccag cagacttcta atactccttt tacctttggc      300
cagggtacga aagttgaaat taaa                                              324
```

<210> SEQ ID NO 139
<211> LENGTH: 351
<212> TYPE: DNA
<213> ORGANISM: Homo sapiens

<400> SEQUENCE: 139

```
gaggtgcagc tggtgcagtc tggagcagag gtgaaaaagc ccggggagtc tctgaagatc      60
tcctgtaagg gttctggata cagctttagc aactactgga tcggctgggt gcgccagatg     120
cccgggaaag gcctggagtg gatggggatc atcgacccta gcaactctta caccagatac     180
agcccgtcct tccaaggcca ggtcaccatc tcagccgaca gtccatcag caccgcctac      240 ctgcagtgga gcagcctgaa ggcctcggac accgccatgt attactgtgc gagatggtac      300 tacaagcccct tcgacgtgtg gggccagggc accctggtga ccgtgagcag c              351
```

<210> SEQ ID NO 140
<211> LENGTH: 351
<212> TYPE: DNA
<213> ORGANISM: Homo sapiens

<400> SEQUENCE: 140

```
gaggtgcagc tggtgcagag cggcgccgag gtgaagaagc ccggcgagag cctgaagatc      60
agctgcaagg gcagcggcta cagcttcagc aactactgga tcggctgggt gcgccagatg     120
cccggcaagg gcctggagtg gatgggcatc atcgaccccca gcaacagcta cacccgctac     180
agccccagct ccaggcca ggtgaccatc agcgccgaca gagcatcag caccgcctac         240 ctgcagtgga gcagcctgaa ggccagcgac accgccatgt actactgcgc ccgctggtac      300 tacaagcccct tcgacgtgtg gggccagggc accctggtga ccgtgagcag c              351
```

<210> SEQ ID NO 141
<211> LENGTH: 351
<212> TYPE: DNA
<213> ORGANISM: Homo sapiens

<400> SEQUENCE: 141

```
gaggtgcaat tggttcagag cggcgcggaa gtgaaaaaac cgggcgaaag cctgaaaatt      60
agctgcaaag gttccggata ttccttttct aattattgga ttggttgggt gcgccagatg     120
cctgggaagg gtctcgagtg gatgggcatt atcgatccgt ctaatagcta cccgctat       180 tctccgagct ttcagggcca ggtgaccatt agcgcggata aaagcattag caccgcgtat      240
cttcaatgga gcagcctgaa agcgagcgat acggccatgt attattgcgc gcgttggtat      300 tataagccctt ttgatgtttg gggccaaggc accctggtga cggttagctc a              351
```

<210> SEQ ID NO 142
<211> LENGTH: 336
<212> TYPE: DNA
<213> ORGANISM: Homo sapiens

<400> SEQUENCE: 142

```
cagtctgtgc tgacgcagcc gccctcagtg tctggggccc cagggcagag ggtcaccatc      60
```

```
tcctgcactg ggagcagctc caacatcggg agcggttatg atgtacactg gtaccagcag      120
cttccaggaa cagcccccaa actcctcatc tatggtaaca gcaagcggcc ctcagggggtc     180 cctgaccgat tctctggctc caagtctggc acctcagcct ccctggccat cactgggctc      240
cagagcgagg atgaggctga ttattactgc gccagctgga ccgacggcct gagcctggtg      300
gtgttcggcg gcggcaccaa gctgaccgtg ctgggc                                336

<210> SEQ ID NO 143
<211> LENGTH: 336
<212> TYPE: DNA
<213> ORGANISM: Homo sapiens

<400> SEQUENCE: 143
cagagcgtgc tgacccagcc ccccagcgtg agcggcgccc ccggccagcg cgtgaccatc       60
agctgcaccg gcagcagcag caacatcggg agcggctacg acgtgcactg gtaccagcag      120
ctgcccggca ccgcccccaa gctgctgatc tacggcaaca gcaagcgccc cagcggcgtg      180
cccgaccgct tcagcggcag caagagcggc accagcgcca gcctggccat caccggcctc      240
cagagcgagg acgaggccga ctactactgt gccagctgga ccgacggcct gagcctggtg      300
gtgttcggcg gcggcaccaa gctgaccgtg ctgggc                                336

<210> SEQ ID NO 144
<211> LENGTH: 336
<212> TYPE: DNA
<213> ORGANISM: Homo sapiens

<400> SEQUENCE: 144
cagagcgtgc tgacccagcc gccttcagtg agtggcgcac aggtcagcg tgtgaccatc        60 tcgtgtacgg gcagcagcag caacattggt tctggttatg atgtgcattg gtaccagcag      120
ttgcccggga cggcgccgaa acttctgatt tatggtaatt ctaagcgtcc ctcaggcgtg      180
ccggatcgtt ttagcggatc caaaagcggc accagcgcga gccttgcgat tacgggcctg      240
caaagcgaag acgaagcgga ttattattgc gcttcttgga ctgatggtct ttctcttgtt      300
gtgtttggcg gcggcacgaa gttaaccgtt cttggc                                336

<210> SEQ ID NO 145
<211> LENGTH: 189
<212> TYPE: PRT
<213> ORGANISM: Homo sapiens

<400> SEQUENCE: 145

Met Leu Gly Ser Arg Ala Val Met Leu Leu Leu Leu Pro Trp Thr
 1               5                  10                  15

Ala Gln Gly Arg Ala Val Pro Gly Gly Ser Ser Pro Ala Trp Thr Gln
             20                  25                  30

Cys Gln Gln Leu Ser Gln Lys Leu Cys Thr Leu Ala Trp Ser Ala His
         35                  40                  45

Pro Leu Val Gly His Met Asp Leu Arg Glu Glu Gly Asp Glu Glu Thr
     50                  55                  60

Thr Asn Asp Val Pro His Ile Gln Cys Gly Asp Gly Cys Asp Pro Gln
 65                  70                  75                  80

Gly Leu Arg Asp Asn Ser Gln Phe Cys Leu Gln Arg Ile His Gln Gly
                 85                  90                  95

Leu Ile Phe Tyr Glu Lys Leu Leu Gly Ser Asp Ile Phe Thr Gly Glu
            100                 105                 110
```

```
Pro Ser Leu Leu Pro Asp Ser Pro Val Ala Gln Leu His Ala Ser Leu
            115                 120                 125

Leu Gly Leu Ser Gln Leu Leu Gln Pro Glu Gly His His Trp Glu Thr
        130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185

<210> SEQ ID NO 146
<211> LENGTH: 19
<212> TYPE: PRT
<213> ORGANISM: Homo sapiens

<400> SEQUENCE: 146

Asn Ile Glu His Lys Tyr Leu Gly Tyr Ala Thr Ser Tyr Ala Ala Ser
1               5                   10                  15

Val Lys Gly

<210> SEQ ID NO 147
<211> LENGTH: 123
<212> TYPE: PRT
<213> ORGANISM: Homo sapiens

<400> SEQUENCE: 147

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Asn Ile Glu His Lys Tyr Leu Gly Tyr Ala Thr Ser Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
            115                 120

<210> SEQ ID NO 148
<211> LENGTH: 12
<212> TYPE: PRT
<213> ORGANISM: Homo sapiens

<400> SEQUENCE: 148

His Gln Gly Leu Ile Phe Tyr Glu Lys Leu Leu Gly
1               5                   10
```